US010738336B2

(12) United States Patent
Beauprez et al.

(10) Patent No.: US 10,738,336 B2
(45) Date of Patent: *Aug. 11, 2020

(54) MUTANT MICROORGANISMS TO SYNTHESIZE COLANIC ACID, MANNOSYLATED AND/OR FUCOSYLATED OLIGOSACCHARIDES

(71) Applicant: Inbiose N.V., Zwijnaarde (BE)

(72) Inventors: Joeri Beauprez, Bredene (BE); Gaspard Lequeux, Ghent (BE); Jo Maertens, Ghent (BE)

(73) Assignee: Inbiose N.V., Zwijnaarde (BE)

( * ) Notice: Subject to any disclaimer, the term of this patent is extended or adjusted under 35 U.S.C. 154(b) by 3 days.

This patent is subject to a terminal disclaimer.

(21) Appl. No.: 15/839,264

(22) Filed: Dec. 12, 2017

(65) Prior Publication Data

US 2018/0216147 A1 Aug. 2, 2018

Related U.S. Application Data

(62) Division of application No. 15/619,377, filed on Jun. 9, 2017, now Pat. No. 9,951,362, which is a division of application No. 14/365,063, filed as application No. PCT/EP2012/075639 on Dec. 14, 2012, now Pat. No. 9,719,119.

(30) Foreign Application Priority Data

Dec. 16, 2011 (EP) .................................... 11194103

(51) Int. Cl.

| | |
|---|---|
| ***C12P 19/04*** | (2006.01) |
| ***C12P 19/32*** | (2006.01) |
| ***C12N 15/52*** | (2006.01) |
| ***C07K 14/245*** | (2006.01) |
| ***C12P 7/40*** | (2006.01) |
| ***C12P 19/12*** | (2006.01) |

(52) U.S. Cl.

CPC ............ *C12P 19/04* (2013.01); *C07K 14/245* (2013.01); *C12N 15/52* (2013.01); *C12P 7/40* (2013.01); *C12P 19/12* (2013.01); *C12P 19/32* (2013.01)

(58) Field of Classification Search

CPC ... C07K 14/245; C07K 16/1232; C12P 19/04; A61K 39/0258

See application file for complete search history.

(56) References Cited

U.S. PATENT DOCUMENTS 5,858,752 A 1/1999 Seed et al.
5,939,279 A 8/1999 Smith et al.

FOREIGN PATENT DOCUMENTS

WO WO 2004003175 1/2004
WO 2006034156 A2 3/2006
WO 2010108909 A1 9/2010
WO 2011083059 A1 7/2011

OTHER PUBLICATIONS

Aerts, D et al., "A constitutive expression system for high throughput screening," 2011, Eng. Life Sci., 11:10-19.
Alper, H. et al., "Tuning genetic control through promoter engineering," 2005, PNAS, 102:12678-12683.
Aristidou, A. et al., "Metabolic engineering of *Escherichia coli* to enhance recombinant protein production through acetate reduction", 1995, Biotechnol. Prog., 11: 475-478.
Beauprez, J. "Metabolic modelling and engineering of *Escherichia coli* for succinate production," 2010, PhD thesis, Ghent University. Ghent, Belgium. (301 pages).
Bode, L. "Recent Advances on Structure, Metabolism, and Function of Human Milk Oligosaccharides" 2006, J. Nutr., 136:2127-2130.
Canton, B. et al., "Refinement and standardization of synthetic biological parts and devices," 2008, Nat Biotech 26:787-793.
Cavallaro, G. et al., Glycosilated Macromolecular Conjugates of Antiviral Drugs with a Polyaspartamide, 2004, Journal of Drug Targeting 12:593-605.
Coppa, G. V. et al., "Prebiotics in human milk: a review" 2006, Digestive and Liver Disease 38:S291-S294.
Datsenko, K. A. et al., "One-step inactivation of chromosomal genes in *Escherichia coli* K-12 using PCR products," 2000, PNAS, 97:6640-6645.
De Mey, M. et al., "Comparison of different strategies to reduce acetate formation in *Escherichia coli*," 2007, Biotechnol. Prog., 23:1053-1063.

(Continued)

*Primary Examiner* — Kagnew H Gebreyesus
(74) *Attorney, Agent, or Firm* — McDonnell Boehnen Hulbert & Berghoff LLP

(57) ABSTRACT

The present invention relates to mutated and/or transformed microorganisms for the synthesis of various compounds. More specifically, the present invention discloses microorganisms mutated in the genes encoding for the regulators ArcA and IclR. The latter mutations result in a significant upregulation of the genes that are part of the colanic acid operon. Hence, said microorganisms are useful for the synthesis of any compound being part of the colanic acid pathway such as GDP-fucose, GDP-mannose and colanic acid, and/or, can be further used—starting form GDP-fucose as a precursor—to synthesize fucosylated oligosaccharides or—starting from GDP-mannose as a precursor—to synthesize mannosylated oligosaccharides. In addition, mutations in the genes coding for the transcriptional regulators ArcA and IclR lead to an acid resistance phenotype in the exponential growth phase allowing the synthesis of pH sensitive molecules or organic acids.

21 Claims, 15 Drawing Sheets

Specification includes a Sequence Listing.

(56) References Cited

OTHER PUBLICATIONS

De Mey, M. et al., "Construction and model-based analysis of a promoter library for *E. coli*: an indispensable tool for metabolic engineering," 2007, BMC Biotechnology, 7:34-48.
Deng, M.-D. et al., "Metabolic engineering of *Escherichia coli* for industrial production of glucosamine and N-acetylglucosamine," 2005, Metabolic Engineering, 7:201-214.
Dumon, C. et al., "In vivo fucosylation of lacto-N-neotetraose and lacto-N-neohexaose by heterologous expression of Helicobacter pylori alpha-1,3 fucosyltransferase in engineered *Escherichia coli*", Glycoconjugate Journal, 18:465-474.
Ebel, W. et al., "*Escherichia coli* RcsA, a Positive Activator of Colanic Acid Capsular Polysaccharide Synthesis, Functions to Activate Its Own Expression," 1999, Journal of Bacteriology 181:577-584.
Foster, J. W., "*Escherichia coli* acid resistance: Tales of an amateur acidophile," 2004, Nature Reviews Microbiology 2:898-907.
Stevenson, G. et al., Organization of the *Escherichia coli* K-12 gene cluster responsible for production of the extracellular polysaccharide colanic acid, 1996, Journal of Bacteriology, 178(16):4885-4893.
Hammer, K et al., "Synthetic promoter libraries-tuning of gene expression," 2006, TRENDS in Biotechnology 24(2):53-55.
Hanahan, D. et al., "Plasmid transformation of *Escherichia coli* and other bacteria," 1991, Methods in Enzymology 204:63-113.
Hommais, F. et al., "GadE (YhiE): a novel activator involved in the response to acid environment in *Escherichia coli*," 2004, Microbiology 150:61-72.
Jigami, Y. "Yeast Glycobiology and Its Application," 2008, Bioscience, Biotechnology, and Biochemistry 72:637-648.
Keasling, J. D., "Gene-expression tools for the metabolic engineering of bacteria," 1999, Trends in Biotechnology 17:452-460.
Lee W. H. et al., "Modulation of guanosine 5'-diphosphate-d-mannose metabolism in recombinant *Escherichiacoli* for production of guanosine 5'-diphosphate-l-fucose," 2006, Bioresource Technology, 100:6143-6148.
Lequeux, G., Metabolic modelling and analysis for the optimisation of *Escherichia coli* as a production host. Ph.D. thesis, 2008, Ghent University, Ghent, Belgium (178 pages).
Lequeux, G. et al., "Metabolic flux analysis of C- and P-limited shikimic acid producing *E. coli*," 2005, Journal of 118:S121-S121.
Masuda, N. et al., "Regulatory network of acid resistance genes in *Escherichia coli.*," 2003, Molecular Microbiology 48:699-712.
Pattyn, F. et al., "RTPrimerDB: The Real-Time PCR primer and probe database," 2006, Nucleic Acids Research 34:D684-D688.
Perrenoud, A. et al., "Impact of global transcriptional regulation by AreA, ArcB, Cra, Crp, Cya, Fnr, and Mlc on glucose catabolism in *Escherichia coli.*," 2005, Journal of Bacteriology 187:3171-3179.
Ringenberg M. et al., "Redirection of sialic acid metabolism in genetically engineered *Escherichia coli*," 2001, Glycobiology, 11:533-539.
Ritz, C. et. al., "qpcR: an R package for sigmoidal model selection in quantitative real-time polymerase chain reaction analysis," 2008, Bioinformatics 24:1549-1551.
The International Search Report of the International Searching Authority for International Application No. PCT/EP2012/075639; dated Apr. 18, 2013, pp. 1-7.
Salis, H.M. et al., "Automated design of synthetic ribosome binding sites to control protein expression," 2009, Nat. Biotech, 27:946-950.
Sanchez A.M. et al., "Novel pathway engineering design of the anaerobic central metabolic pathway in *Escherichia coli* to increase succinate yield and productivity," 2005, Metabolic Engineering, 7:229-239.
Shalei-Levanon, S. et al., "Effect of AreA and FNR on the expression of genes related to the oxygen regulation and glycolysis pathway in *Escherichia coli* under growth conditions," 2005, Biotechnology and Bioengineering, 92:147-159.
Shalei-Levanon, S. et al., "Effect of oxygen on teh *Escherichia coli* AreA and FNR regulation systems and metabolic responses," 2005, Biotechnology and Bioengineering , 89:556-564.
Smyth, G.K., "Limma: Linear models for microarray data," 2005, In: Bioinformatics and Computational iology Solutions using R and Bioconductor, R. Gentleman, V. Carey, S. Dudoit, R. Irizarry, W. Huber (eds.) Springer, New York, pp. 397-420.
Smyth, G.K., "Linear Models and Empirical Bayes Methods for Assessing Differential Expression in Microarray Experiments," 2004, Statistical Applications in Genetics and Molecular Biology 3:1-26.
Smyth, G.K. et al., "Normalization of eDNA microarray data," 2003, Methods 31:265-273.
Spiess, A.N. et al., "Highly accurate sigmoidal fitting of real-time PCR data by inroducing a parameter for asymmetry," 2008, BMC Bioinformatics 9:221.
Stevenson, G. et al., "Organization of the *Escherichia coli* K-12 gene cluster responsible for production of the extracellular polysaccharide colanic acid," 1996, Journal of Bacteriology, 178:4885-4893.
Stout, V. et al., "RcsA, an unstable positive regulator of capsular polysaccharide synthesis," 1991, Journal of Bacteriology 173:1738-1747.
Sunnarborg, A et al., "Regulation of the glyoxylate bypass operon: cloning and characterization of IciR.," 1990, Journal of Bacteriology 172:2642-2649.
Waegeman, H.J. et al., "Effect of icIR and arcA knockouts on biomass formation and metabolic fluxes in *Escherichia coli* K12 and its implications on understanding the metabolism of *Escherichia coli* BL21 (DE3)," 2011, BMC Microbiology 11:(70) 1-17.
Waegeman H. et al., "Effect of icIR and arcA deletions on pysiology and metabolic fluxes in *Escherichia coli* BL 21 (DE3)," 2012, Biotechnol Lett., 34:329-337.
Waegeman H. et al., "Increasing recombinant protein production in *Escherichia coli* through metabolic and genetic engineering," 2011, J Ind Microbiol Biotechnol, 38:1891-1910.
Waegeman H. et al., "Increasing recombinant protein production in *Escherichia coli* K12 through metabolic engineering," 2013, New Biotechnology, 30:255-61.
Warnecke, T., et al., "Organic acid toxicity, tolerance, and production in *Escherichia coli* biorefining applications," 2005, Microbial Cell Factories 4:25.
Waegeman. et al., (Effect of icIR and arcA knockouts on biomass formation and metabolic fluxes in *Escherichia coli* K12 and its implications on understanding the metabolism of *Escherichia coli* BL21 (DE3) BMC Microbiol. Apr. 11, 2011.
Waegeman. et al., (Effect of icIR and arcA deletions on physiology and metabolic fluxes in *Escherichia coli* BL21 (DE3), Biotechnology Letters vol. vol. 34, No. 2, Oct. 19, 2011, p. 329-337.
Yao et al., "Catabolic regulation analysis of *Escherichia coli* and its crp, mlc, mgsA, pgi and ptsG mutants", Microbial cell Factories, 10(67):1-11 (Aug. 2011).
Castanie-Cornet et al., "Control of Acid Resistance in *Escherichia coli*" Journal of Bacteriology 181(11):3525-35 (Jun. 1999).
Cottaz & Samain, "Genetic engineering of *Escherichia coli* for the production of NI,NII-diacetylchitobiose (chitinbiose) and its utilization as a primer for the synthesis of complex carbohydrates." Metab. Eng. 7(4):311-17 (Jul. 2005).
Deng et al., "Metabolic engineering of *Escherichia coli* for industrial production of glucosamine and N-acetylglucosamine," Metab. Eng. 7:201-04 (Mar. 2005).
Drouillard et al., "Efficient synthesis of 6'-sialyllactose, 6,6'-disialyllactose, and 6'-KDO-lactose by metabolically engineered *E. coli* expressing a multifunctional sialyltransferase from the *Photobacterium* sp. JT-ISH-224." Carbohydr. Res. 345(10):1394-99 (Jul. 2010).
Zanfardino et al., "Isolation of an *Escherichia coli* K4 kfoC mutant over-producing capsular chondroitin." Microb. Cell Fact. 9:34 (May 2010). 8 pages.

Figure 15:

UTR sequence part (SEQ ID N° 3)

TGTTTATTTATCACTTTGGCAGAGTAATTATCCTGTGCACTATTAATAGCAATGTCGCCA
TGCACATTTACCTTGCAGTTAATTGAATAAAAATTTAACTGGCATCAGTCCTAAAAAAAT
TGATTTCATCCGCAGGCTATTGACAGAATAATTCAGACTGGTCTTTCAGGCATCCAGACA
CGCTACCGCCCCTGGCTTTTTAGCTACCAATACACTGATTTAGTTTAATTTTTCACACCC
TCTCAGCATGCAGTCGTTGATGAGAAAGGGTTATTACGGAAATTAACTTCCGAATATAAG
GTGACATTATGGTAATTGAATATTGGCTTTCCAATAATGC

Artificial promoter sequence part (SEQ ID N° 4)

CGAGGTCGACGGATCCCAAGCTTCTTCTAGAGCGGCCGCCATGGAAATTTCCCTATTATA
CCATATGCCGGCCAAGATGTCAAGAAACTTATAGAATGAAG

Regulon sequence part SEQ ID N° 5)

TAAGTGTCATTCAATATGGTTTTTAGGAGTTTCTTTAGGTTGAC

Complete promoter sequence (SEQ ID N° 6):

TGTTTATTTATCACTTTGGCAGAGTAATTATCCTGTGCACTATTAATAGCAATGTCGCCAT
GCACATTTACCTTGCAGTTAATTGAATAAAAATTTAACTGGCATCAGTCCTAAAAAAATTG
ATTTCATCCGCAGGCTATTGACAGAATAATTCAGACTGGTCTTTCAGGCATCCAGACACGC
TACCGCCCCTGGCTTTTTAGCTACCAATACACTGATTTAGTTTAATTTTTCACACCCTCTC
AGCATGCAGTCGTTGATGAGAAAGGGTTATTACGGAAATTAACTTCCGAATATAAGGTGAC
ATTATGGTAATTGAATATTGGCTTTCCAATAATGCCGAGGTCGACGGATCCCAAGCTTCTT
CTAGAGCGGCCGCCATGGAAATTTCCCTATTATACCATATGCCGGCCAAGATGTCAAGAAA
CTTATAGAATGAAGTAAGTGTCATTCAATATGGTTTTTAGGAGTTTCTTTAGGTTGAC

MUTANT MICROORGANISMS TO SYNTHESIZE COLANIC ACID, MANNOSYLATED AND/OR FUCOSYLATED OLIGOSACCHARIDES

INCORPORATION BY CROSS-REFERENCE

This application is a divisional of U.S. application Ser. No. 15/619,377, filed on Jun. 9, 2017, which is a divisional of U.S. application Ser. No. 14/365,063, filed on Jun. 12, 2014, which is the U.S. national phase of International Application No. PCT/EP2012/075639, filed on Dec. 14, 2012, which claims the benefit of European patent application 11194103.5, filed on Dec. 16, 2011, the disclosures of which are incorporated herein by reference in their entirety.

FIELD OF THE INVENTION

The present invention relates to mutated and/or transformed microorganisms for the synthesis of various compounds. More specifically, the present invention discloses microorganisms mutated in the genes encoding for the regulators ArcA and IclR. The latter mutations result in a significant upregulation of the genes that are part of the colanic acid operon. Hence, said microorganisms are useful for the synthesis of any compound being part of the colanic acid pathway such as GDP-fucose, GDP-mannose and colanic acid, and/or, can be further used—starting from GDP-fucose as a precursor—to synthesize fucosylated oligosaccharides or—starting from GDP-mannose as a precursor—to synthesize mannosylated oligosaccharides. In addition, mutations in the genes coding for the transcriptional regulators ArcA and IclR lead to an acid resistance phenotype in the exponential growth phase allowing the synthesis of pH sensitive molecules and organic acids.

BACKGROUND OF THE INVENTION

The genes arcA encoding for the aerobic respiration control protein and iclR encoding the isocitrate lyase regulator are known to regulate the central carbon metabolism. ArcA is a global transcriptional regulator that regulates a wide variety of genes, while IclR is a local transcriptional regulator that regulates the glyoxylate pathway. ArcA is known to regulate the central carbon metabolism in response to oxygen deprivation and has no connection with IclR other than that it also regulates the glyoxylate pathway (24, 28, 29, 37, 38). In an earlier study the combined effect of ΔiclRΔarcΔ mutant strains on the central carbon metabolism has been observed. Increased fluxes were shown in the tricarboxylic acid (TCA) cycle and glyoxylate pathway and an interesting and surprising phenotype appeared when both genes where knocked out, namely the double mutant strain formed biomass with a yield that approached the maximal theoretical yield (4, 39).

Some compounds, such as GDP-fucose, are in high demand. The latter compound is indeed a precursor of fucosylated oligosaccharides such as fucosyllactose, fucosyllactoNbiose and lewis X oligosaccharides, or, of fucosylated proteins. These sugars are components of human mother milk in which they have anti-inflammatory and prebiotic effects and/or have applications in therapeutics as nutraceutical, anti-inflammatory agent or prebiotic, in addition, fucosylated proteins find applications in the pharmaceutics (5, 8, 27). However, an efficient method to produce the latter high-value compounds is still needed.

In addition GDP-mannose is also an intermediate of the pathway towards GDP-fucose. Interrupting the pathway prematurely leads to the accumulation of this compound, which is a precursor of mannosylated oligosacharides. These oligosaccharides find for example applications in the treatment of gram-negative bacterial infections, in addition, GDP-mannose is important for the humanization of protein glycosylations, which is essential for the production of certain therapeutic proteins (18, 30). Mannosylated oligosaccharides and mannosylated glycoconjugates are also used for drug targeting, for instance mannosylated antivirals can specifically target the liver and kidneys (7).

The present invention provides microorganisms which are genetically changed in such a manner that they can efficiently produce the latter compounds.

Moreover, the synthesis of pH sensitive molecules, such as—but not limited to—glucosamine, and organic acids, such as—but not limited to—pyruvic acid, succinic acid, adipic, sialic acid, sialylated oligosaccharides . . . are preferably produced at low pH, either to stabilize the product or for downstream processing reasons (4, 12, 40). Therefore, strains that can grow at low pH are beneficial for these production processes. *E. coli* is an organism that can adapt easily to various conditions, for instance it can easily adapt to the harsh pH conditions in the stomach, which is about pH 2 (14). Nonetheless, *E. coli* does not seem to grow at these conditions, but induces its acid resistance mechanisms in the stationary phase (40). During this phase the cell does not multiply anymore and therefore hampers productivity. Up to now, no solution was found to this problem. However, in the present invention, a genetically engineered microorganism is provided that can induce acid resistance mechanisms in the exponential growth phase, which is the phase that is mostly used for production of organic acids and pH instable products.

| Gene: | Function: |
|---|---|
| wza | Component of capsular polysaccharide export apparatus |
| wzb | Tyrosine phosphatase |
| wzc | Tyrosine kinase |
| wcaA | Glycosyltransferase |
| wcaB | Acyltransferase |
| wcaC | Glycosyltransferase |
| wcaD | Colanic acid polymerase |
| wcaE | Glycosyltransferase |
| wcaF | Acyltransferase |
| gmd | GDP-mannose-4,6-dehydratase |
| fcl | GDP-fucose synthase |
| gmm | GDP-mannose hydrolase |
| wcaI | Glycosyltransferase |
| cpsB | Mannose-1-phosphate guanylyltransferase |
| cpsG | Phosphomannomutase |
| wcaJ | UDP-glucose lipid carrier transferase |

-continued

| Gene: | Function: |
|---|---|
| wzxC | Putative transporter |
| wcaK | Pyruvyltransferase |
| wcaL | Glycosyltransferase |
| wcaM | Predicted protein in colanic acid biosynthesis |

Figure 4:
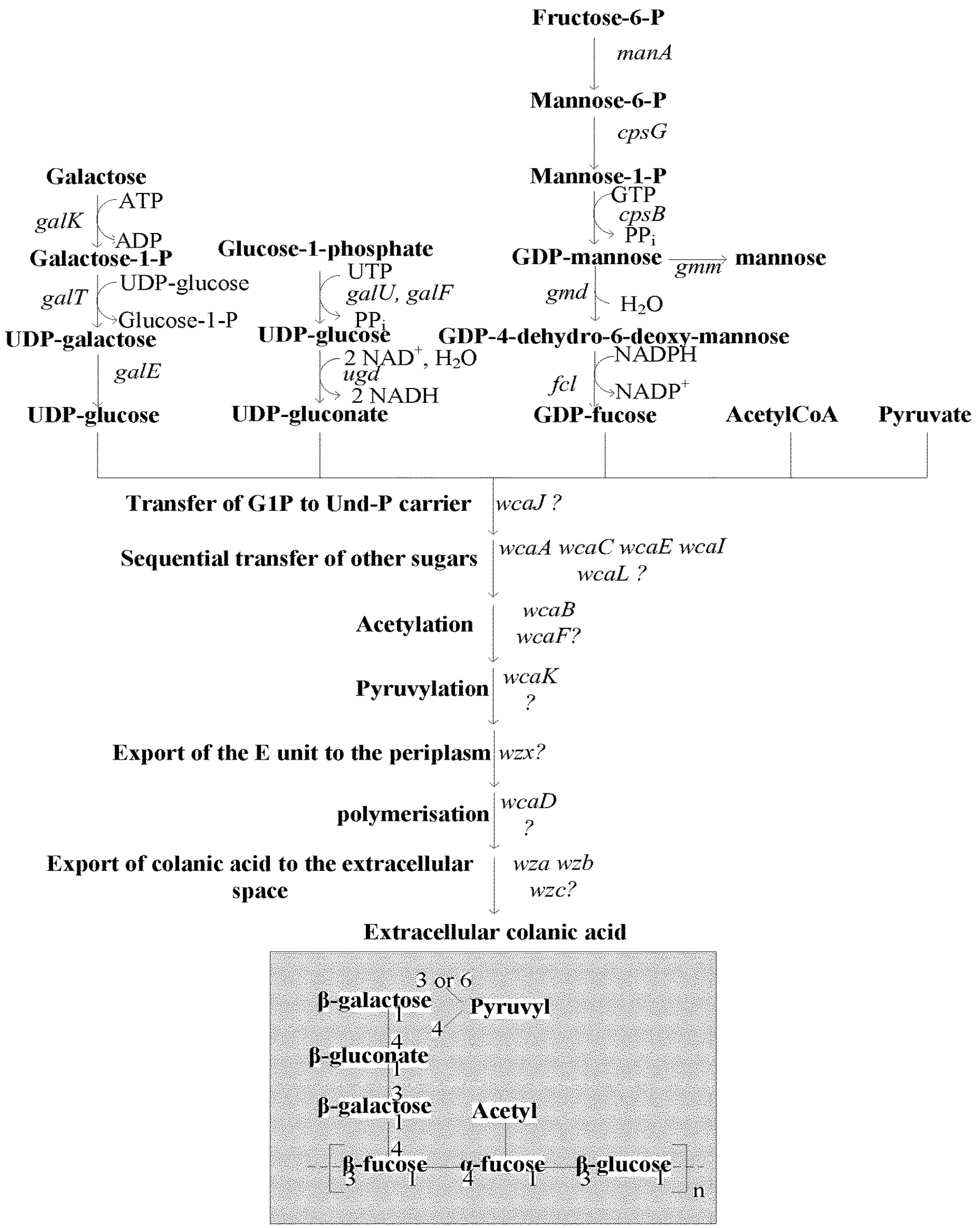

FIG. 4: The colanic acid biosynthesis pathway.

Figure 5:
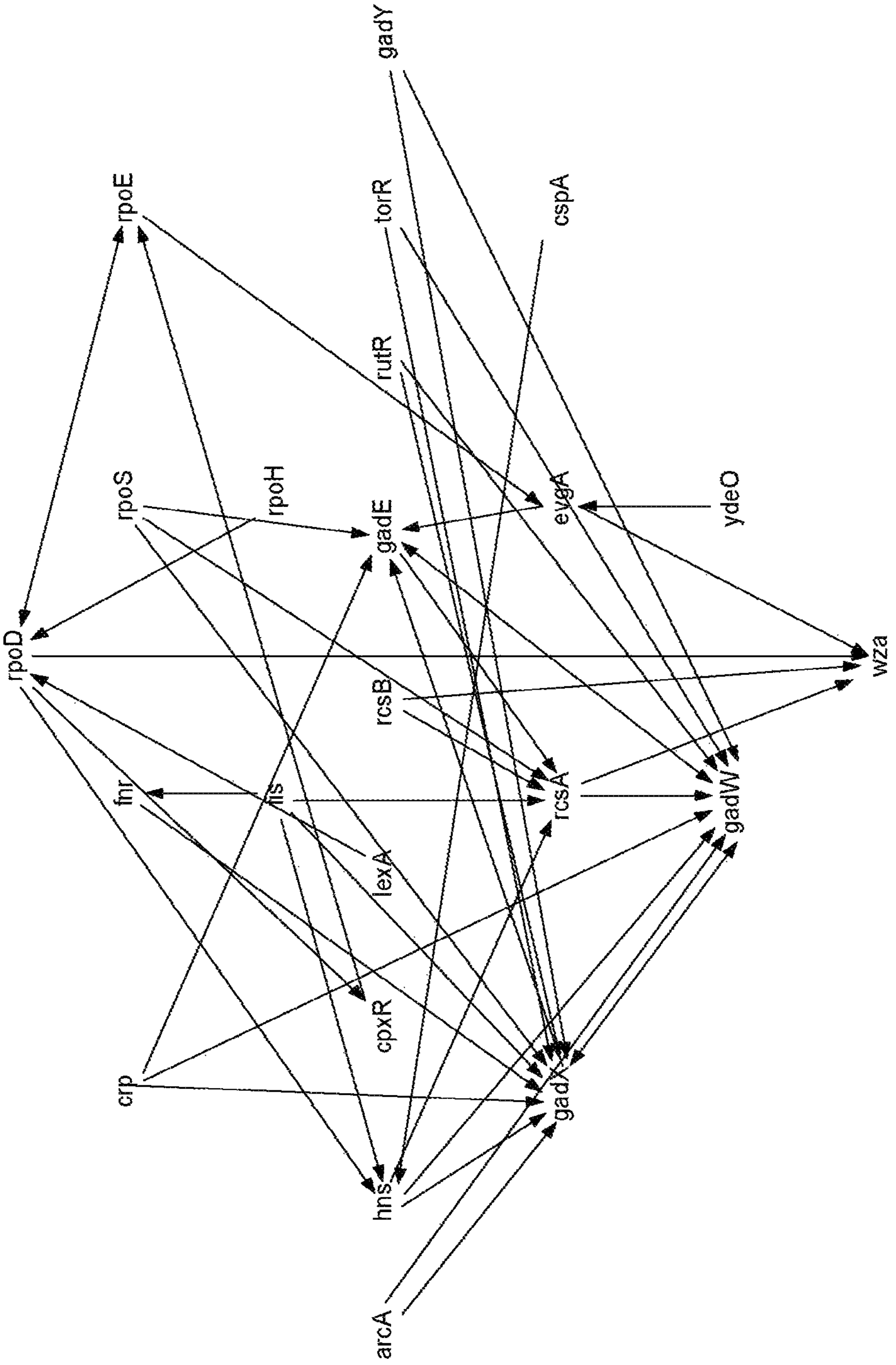

FIG. 5: Regulatory network of the colanic acid operon. This network was constructed with Pathway tools v 13.0.

Figure 6:
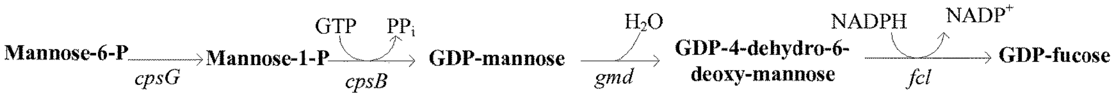
Figure 6:
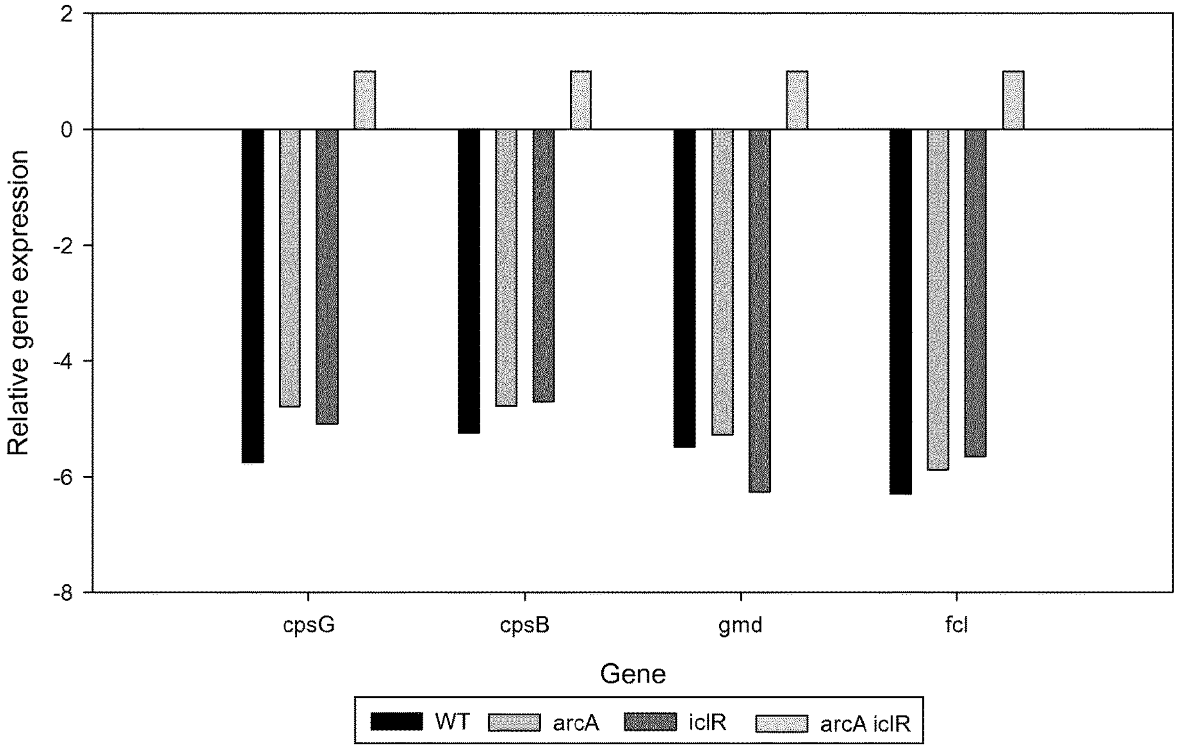

FIG. 6: Effect of the ΔarcAΔiclR mutations on the GDP-fucose biosynthesis route.

Figure 7:
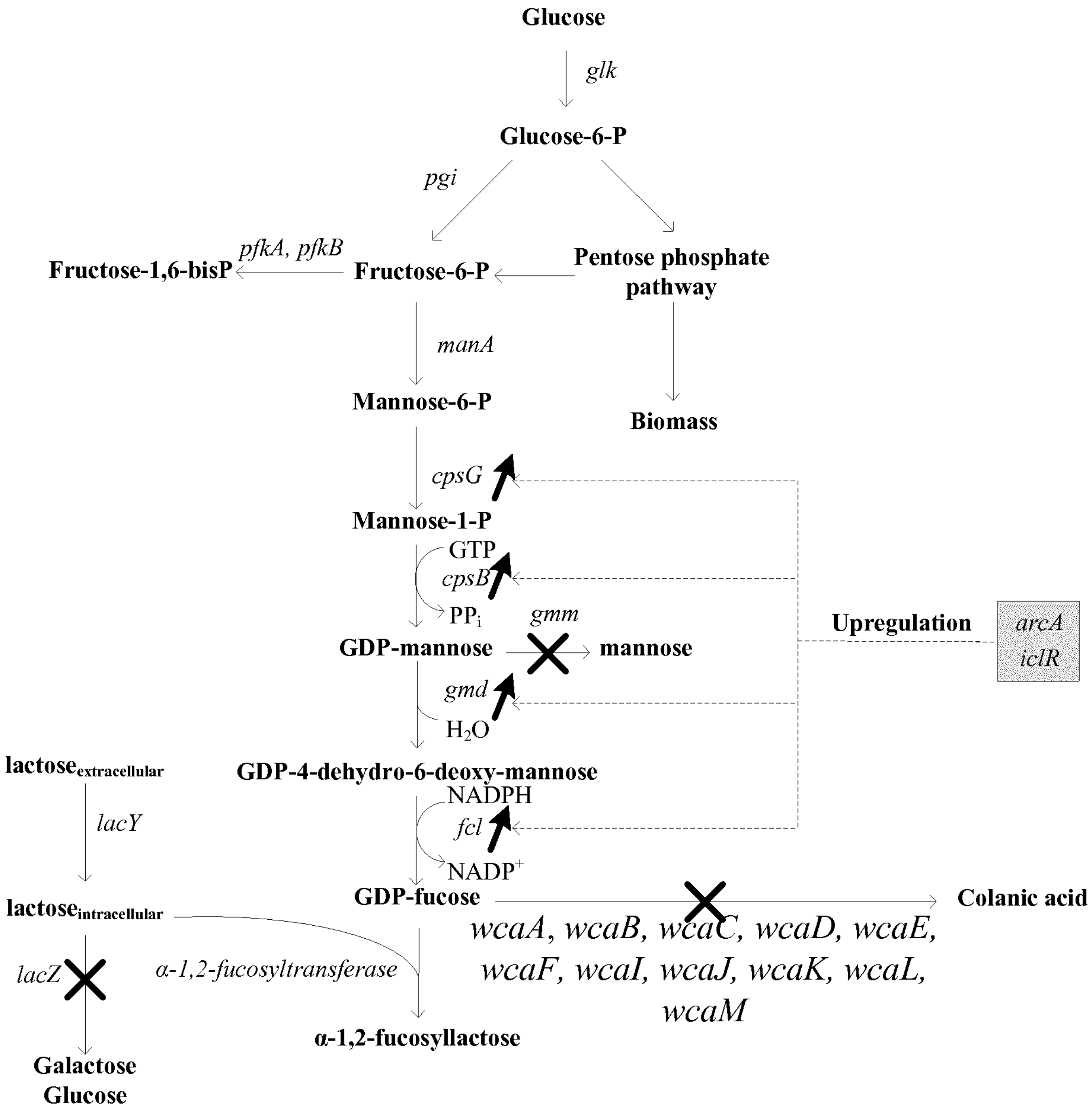

FIG. 7: Overview of the genetic modifications needed to enhance fucosyllactose and fucosylated oligosaccharides production starting from glucose as a substrate.

Figure 8:
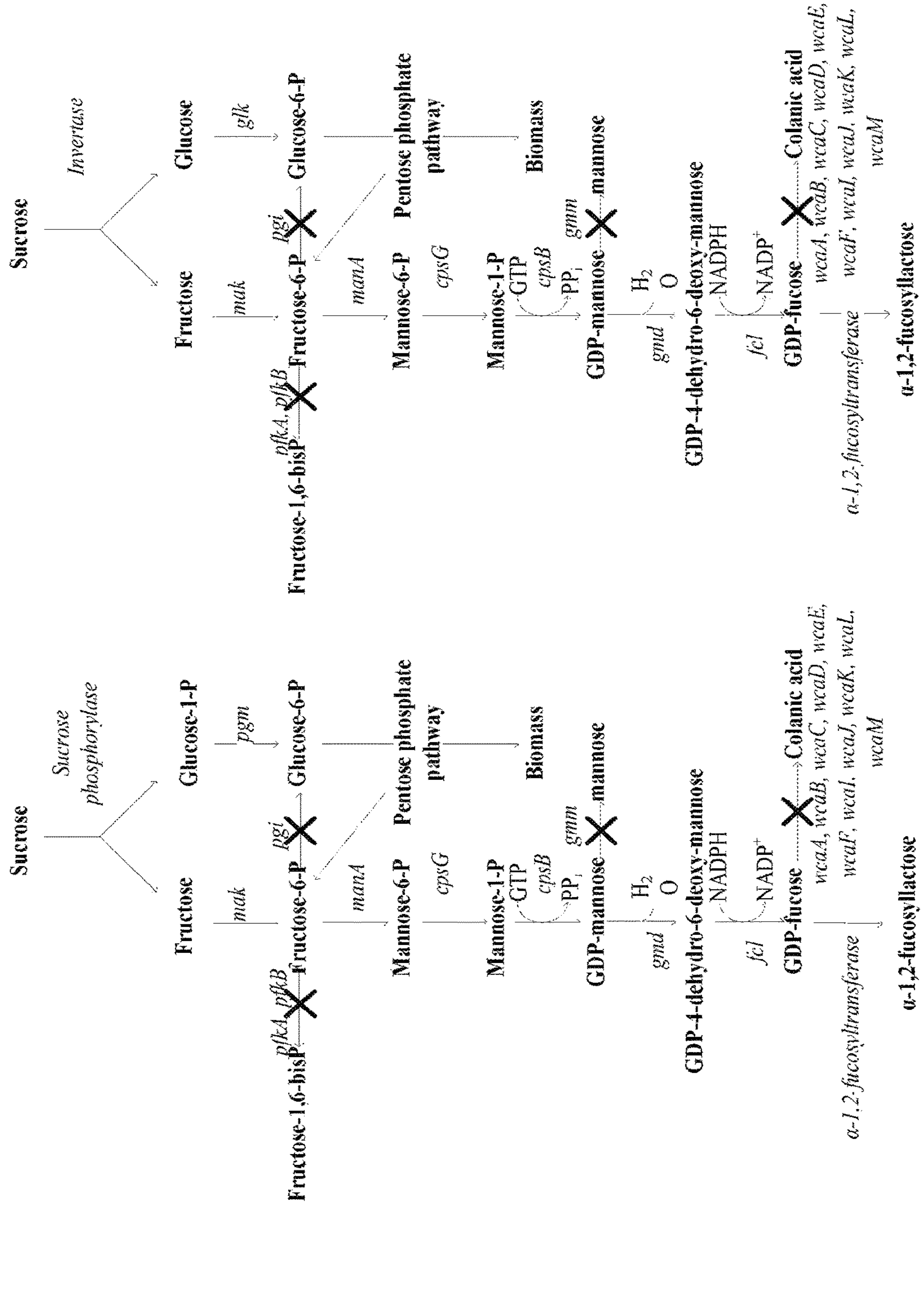

FIG. 8: Starting from sucrose, fucosylated sugar derivates such as fucosyllactose and more specifically 1,2-fucosyllactose are produced. The strain is modified to force the cell to produce frucose-6-phosphate which is an intermediate in the synthesis of GDP-fucose. Glucose or glucose-1-phosphate (if the starting enzyme is either a sucrase or a sucrose phosphorylase) is then fed to the central carbon metabolism via the pentose phosphate pathway.

Figure 9:
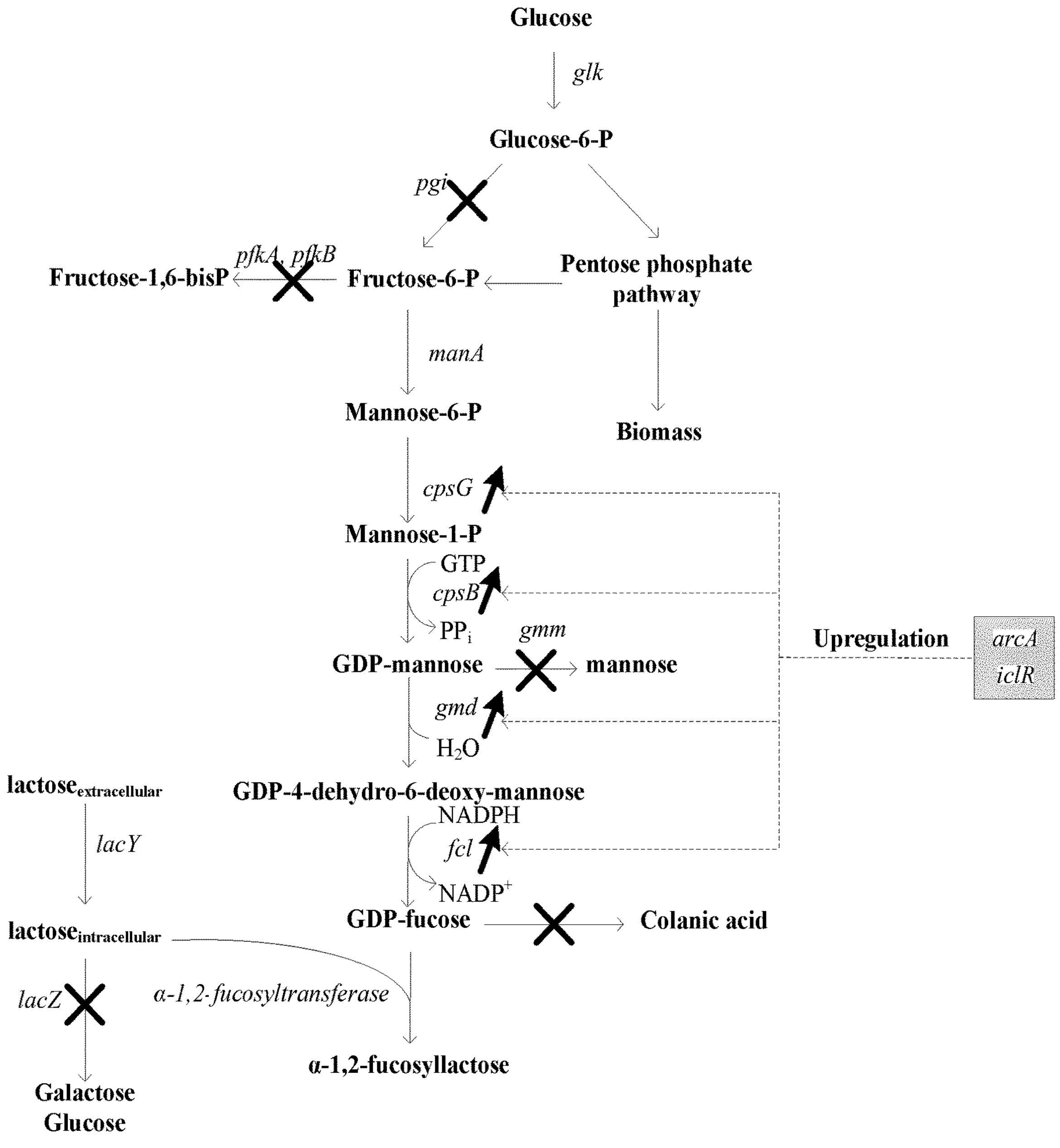

FIG. 9: Overview of the genetic modifications needed to enhance fucosyllactose and fucosylated oligosaccharides production starting from glucose as a substrate in a split metabolism.

Figure 10:
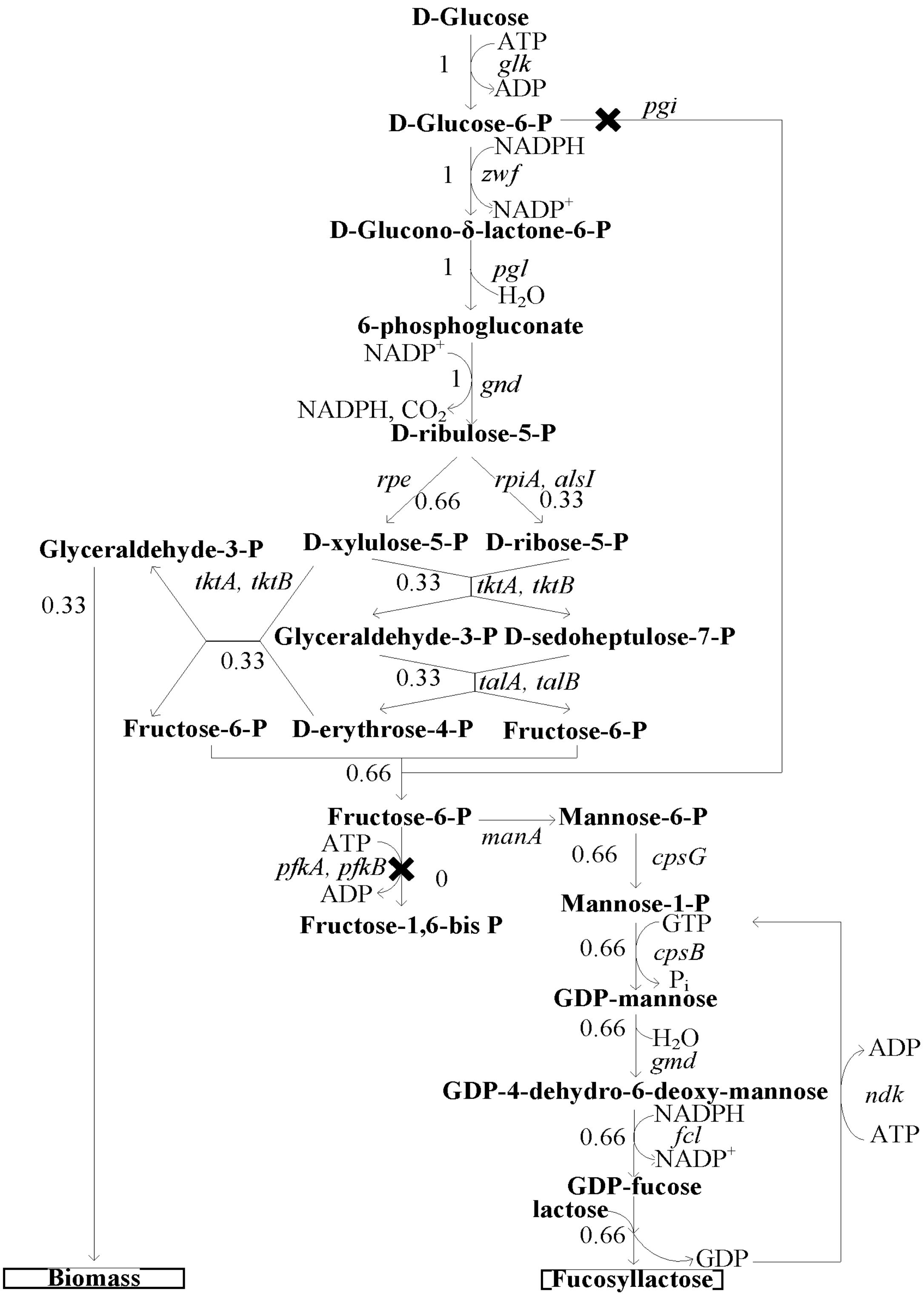

FIG. 10: Detail of the pentose phosphate pathway flux in a strain in which the genes coding for phosphoglucose isomerase and phosphofructokinase are knocked out.

Figure 11:
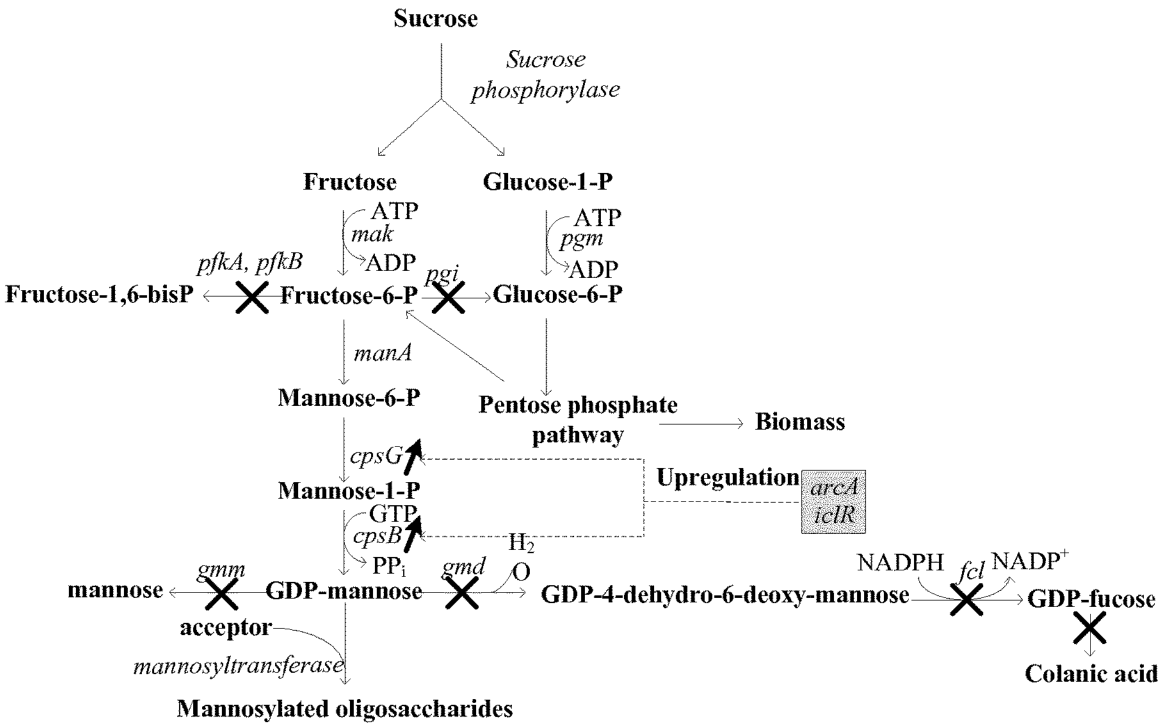
Figure 11:
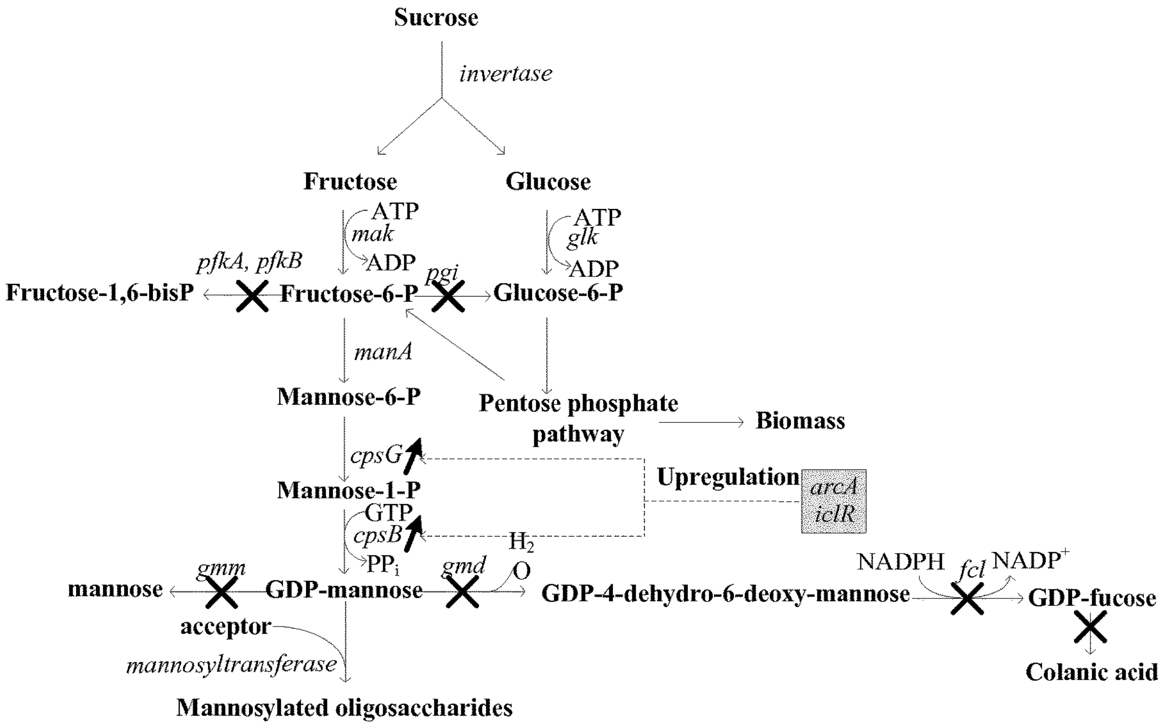

FIG. 11: Starting from sucrose, mannosylated sugar derivates are produced. The strain is modified to force the cell to produce frucose-6-phosphate which is an intermediate in the synthesis of GDP-fucose. Glucose or glucose-1-phosphate (if the starting enzyme is either a sucrase or a sucrose phosphorylase) is then fed to the central carbon metabolism via the pentose phosphate pathway.

Figure 12:
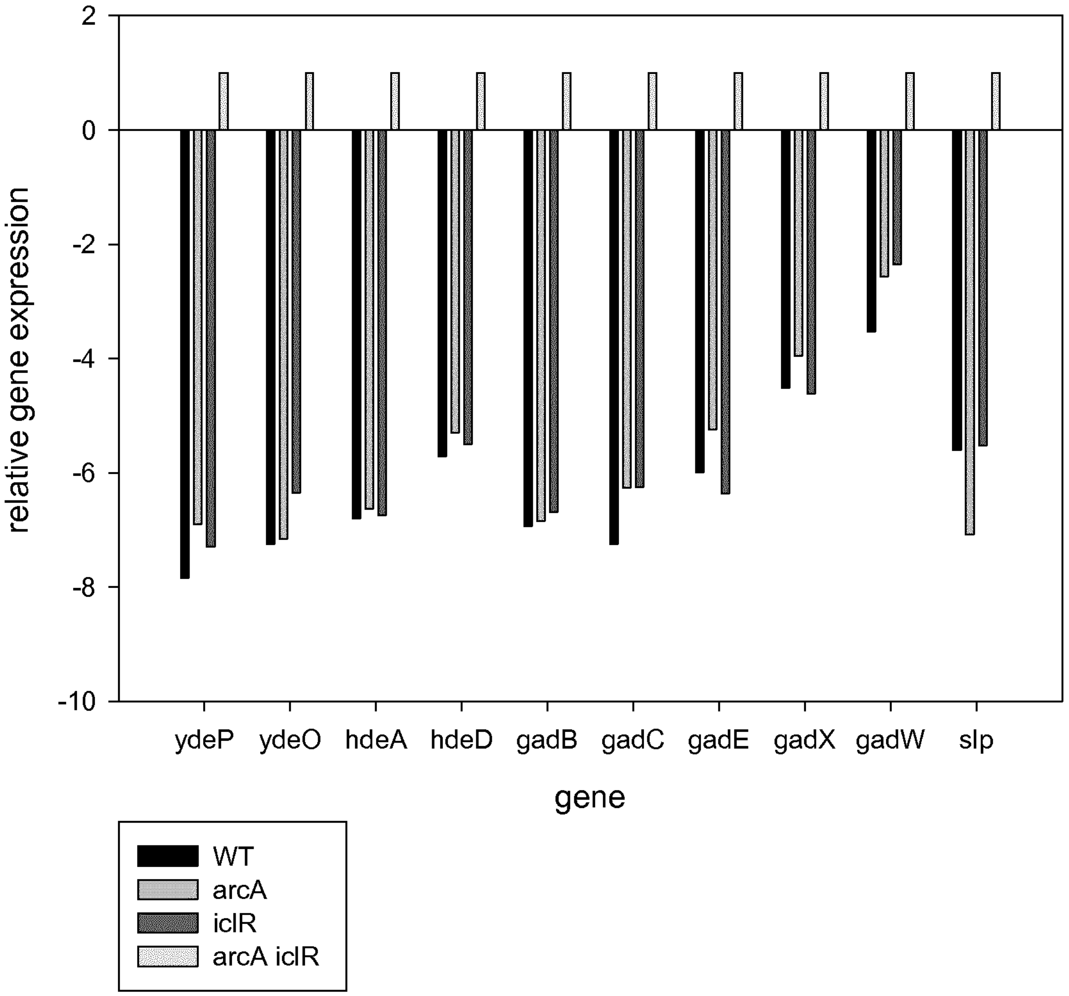

FIG. 12: Gene expression pattern acid resistance related genes of the wild type, the ΔiclR and ΔarcA mutant strain in batch culturing conditions relative to the ΔarcAΔiclR mutant strain.

Figure 13:
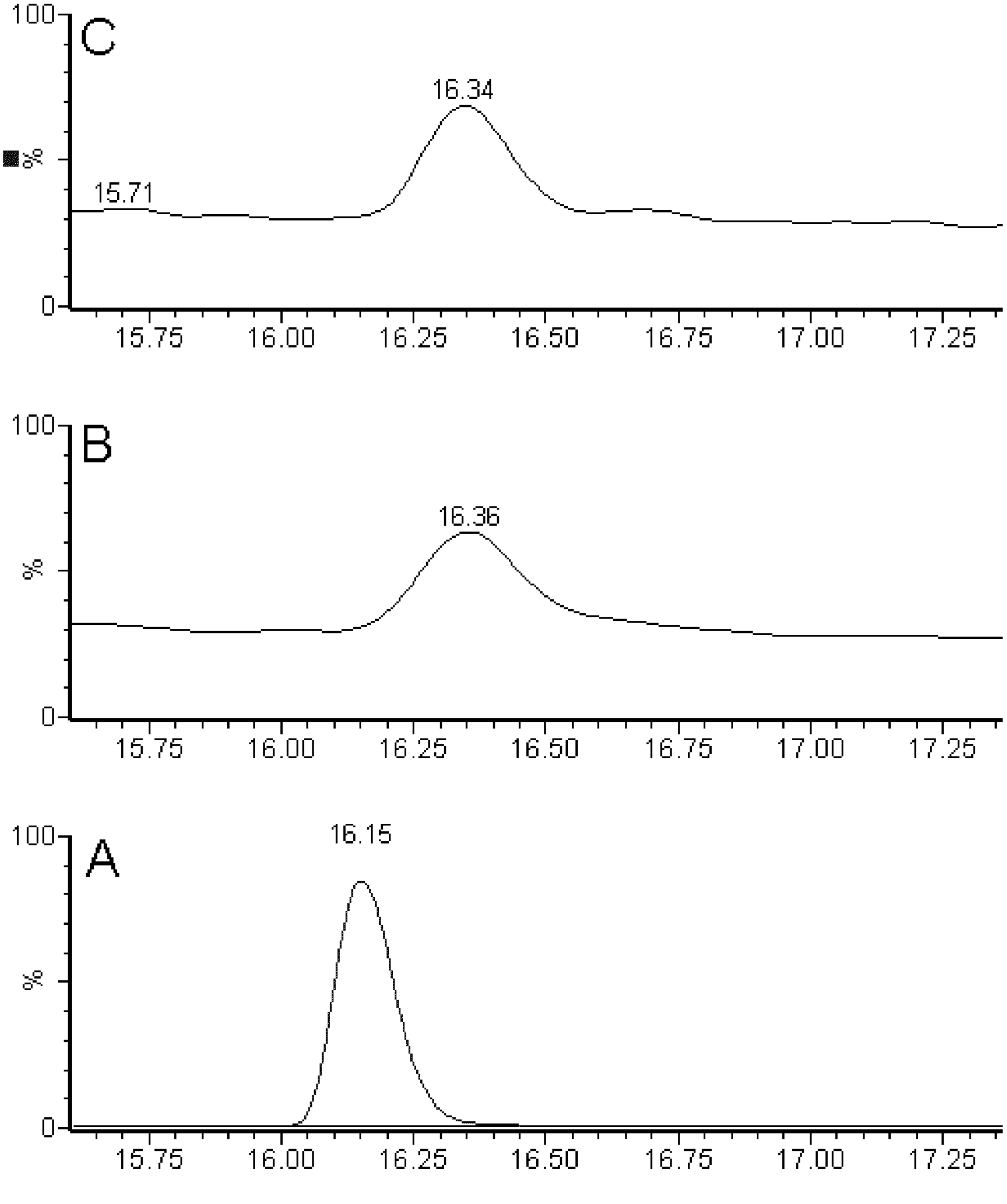

FIG. 13: LC MSMS analysis chromatograms of culture broth and a 2-fucosyllactose standard. A. LC MSMS analysis of the standard, B. LC MSMS analysis of a sample of the culture broth of a mutant strain expressing a *H. pylori* fucosyltransferase, C. LC MSMS analysis of a sample of the culture broth of a mutant strain expressing a *H. pylori* fucosyltransferase.

Figure 14:
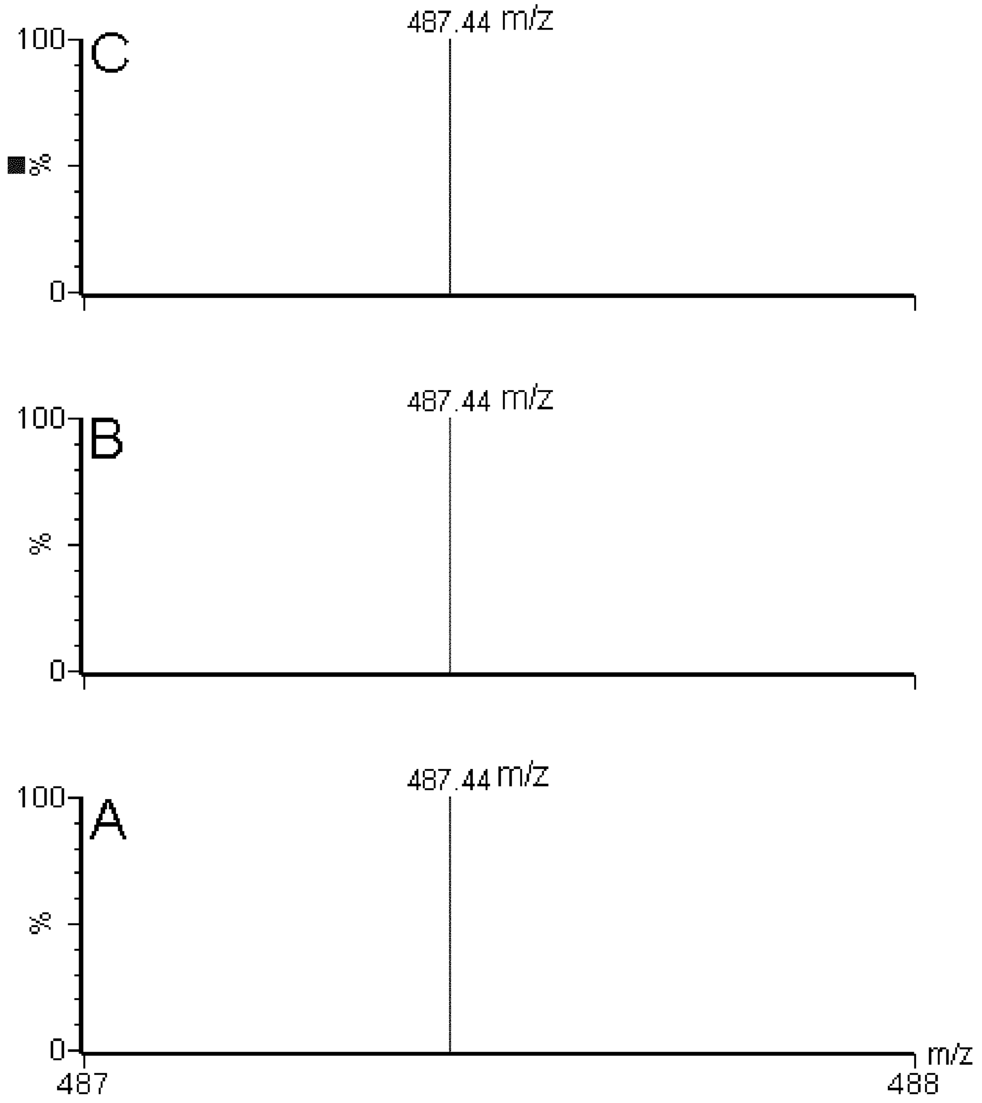

FIG. 14: LC MSMS analysis mass spectrum from the chromatograms shown in FIG. 13 of culture broth and a 2-fucosyllactose standard. A. Mass (m/z) of the standard, B. Mass (m/z) of the sample of the culturing broth of a mutant strain expressing a *H. pylori* fucosyltransferase, C. Mass (m/z) of the sample of the culturing broth of a mutant strain expressing a *H. pylori* fucosyltransferase.

FIG. 15: The sequence of the artificial hybrid promoter as given by SEQ ID No 6 (the combination of the native and an artificial promoter) that was cloned in front of the colanic acid operon.

DESCRIPTION OF INVENTION

The present invention provides microorganisms such as Enterobacteriaceae which are genetically changed in such a manner that they can efficiently produce compounds which are part of the colanic acid pathway. A particular compound of interest is GDP-fucose which is used as a precursor to synthesize fucosylated oligosaccharides. The latter have health-promoting effects as indicated above but there is no efficient production method available to produce said compounds.

The present invention thus provides for the usage of a mutated and/or transformed microorganism comprising a genetic change leading to a modified expression and/or activity of the transcriptional regulators the aerobic respiration control protein ArcA and the isocitrate lyase regulator IclR to upregulate at least one of the genes of the colanic acid operon, wherein said operon comprises the genes cpsG, cpsB, gmd and fcl that code for a phosphomannomutase, a mannose-1-phosphate guanylyltransferase, GDP-mannose 4,6-dehydratase and GDP-fucose synthase, respectively. The latter operon may also comprise the genes cpsG, cpsB, gmd, fcl and wza. In addition the expression of the gene rcsA is increased. This gene is a transcriptional regulator of the colanic acid operon. Enhanced expression of this gene increases transcription of the colanic acid operon (13, 36).

Hence the present invention relates to the usage of a mutated and/or transformed microorganism comprising a genetic change leading to a modified expression and/or activity of the transcriptional regulator, the aerobic respiration control protein, ArcA and the isocitrate lyase regulator IclR to upregulate the transcriptional regulator of the colanic acid operon, rcsA, which in turn upregulates at least one of the genes of the colanic acid operon.

Hence, the present invention relates to a mutated and/or transformed microorganism such as—but not limited to Enterobacteriaceae such as an *Escherichia coli* (*E. coli*) strain comprising a genetic change leading to a modified expression of the transcriptional regulators: the aerobic respiration control protein ArcA and the isocitrate lyase regulator IclR.

A mutated and/or transformed microorganism such as *E. coli* as used here can be obtained by any method known to the person skilled in the art, including but not limited to UV mutagenesis and chemical mutagenesis. A preferred manner to obtain the latter microorganism is by disrupting (knocking-out) the genes (arcA and iclR) encoding for the proteins ArcA and IclR, or, by replacing the endogenous promoters of said genes by artificial promoters or replacing the endogenous ribosome binding site by an artificial ribosome binding site. The term 'artificial promoters' relates to heterologous or non-natural or in silico designed promoters with known expression strength, these promoters can be derived from libraries as described by Alper et al. (2005), Hammer et al. (2006), or De Mey et al. (2007) (3, 11, 15). The term heterologous promoter refers to any promoter that does not naturally occur in front of the gene. The term 'artificial promoter' may also refer to promoters with DNA sequences that are combinations of the native (autologous) promoter sequence with parts of different (autologous or heterologous) promoter sequences as for example shown further in the examples. Sequences of such 'artificial promoters' can be found in databases such as for example partsregistry.org (6). The term 'artificial ribosome binding site' relates to heterologous or non-natural or in silico designed ribosome binding sites with known or measurable translation rates, these libraries can be derived from libraries or designed via algorithms as described by Salis et al (2009) (26). Hence, the present invention specifically relates to a mutated and/or transformed microorganism as indicated above wherein said genetic change is disrupting the genes encoding for ArcA and IclR, or, reducing or eliminating the function of ArcA and IclR via mutations in the coding sequence of the genes coding for ArcA and IclR, or, is replacing the endogenous promoters of the genes encoding for ArcA and IclR by artificial promoters; or, is replacing the endogenous ribosome binding site by an artificial ribosome binding site. It is further clear that the mutant and/or transformant according to the present invention may further comprise additional genetic changes in one or more other genes within its genome as is also described further. The term microorganism specifically relates to a bacterium, more specifically a bacterium belonging to the family of Enterobacteriaceae. The latter bacterium preferably relates to any strain belonging to the species *Escherichia coli* such as but not limited to *Escherichia coli* B, *Escherichia coli* C, *Escherichia coli* W, *Escherichia coli* K12, *Escherichia coli* Nissle. More specifically, the latter term relates to cultivated *Escherichia coli* strains—designated as *E. coli* K12 strains—which are well-adapted to the laboratory environment, and, unlike wild type strains, have lost their ability to thrive in the intestine. Well-known examples of the *E. coli* K12 strains are K12 Wild type, W3110, MG1655, M182, MC1000, MC1060, MC1061, MC4100, JM101, NZN111 and AA200. Hence, the present invention specifically relates to a mutated and/or transformed *Escherichia coli* strain as indicated above wherein said *E. coli* strain is a K12 strain. More specifically, the present invention relates to a mutated and/or transformed *Escherichia coli* strain as indicated above wherein said K12 strain is *E. coli* MG1655.

The terms 'leading to a modified expression or activity' indicates that the above described mutations/transformations affects the transcription and/or translation and/or post-translational modification of said genes (arcA and iclR) into the transcriptional regulator proteins of the present invention (ArcA and IclR) in such a way that the latter transcription has significantly decreased or has even been completely abolished compared to a wild type strain, which has not been mutated or transformed with regard to both particular genes of the present invention. Hence, the present invention relates to a mutated and/or transformed microorganism such as an *Escherichia coli* strain as indicated above wherein said modified expression is a decreased expression, and, to a mutated and/or transformed microorganism such as an *Escherichia coli* strain as indicated above wherein said decreased expression is an abolished expression.

Figure 2:
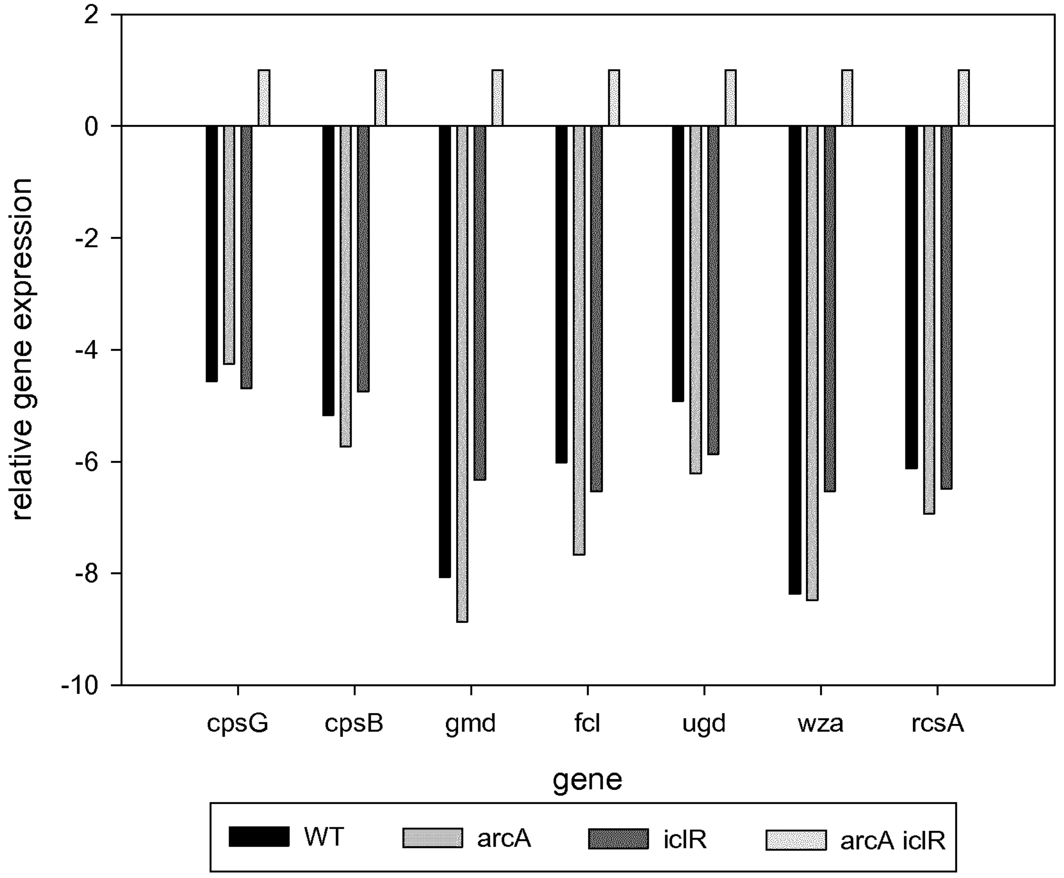
FIG. 2: Gene expression pattern of the colanic acid operon of the wild type, the ΔiclR and ΔarcA mutant strain in chemostat fermentation conditions relative to the ΔarcAΔiclR mutant strain.
Figure 3:
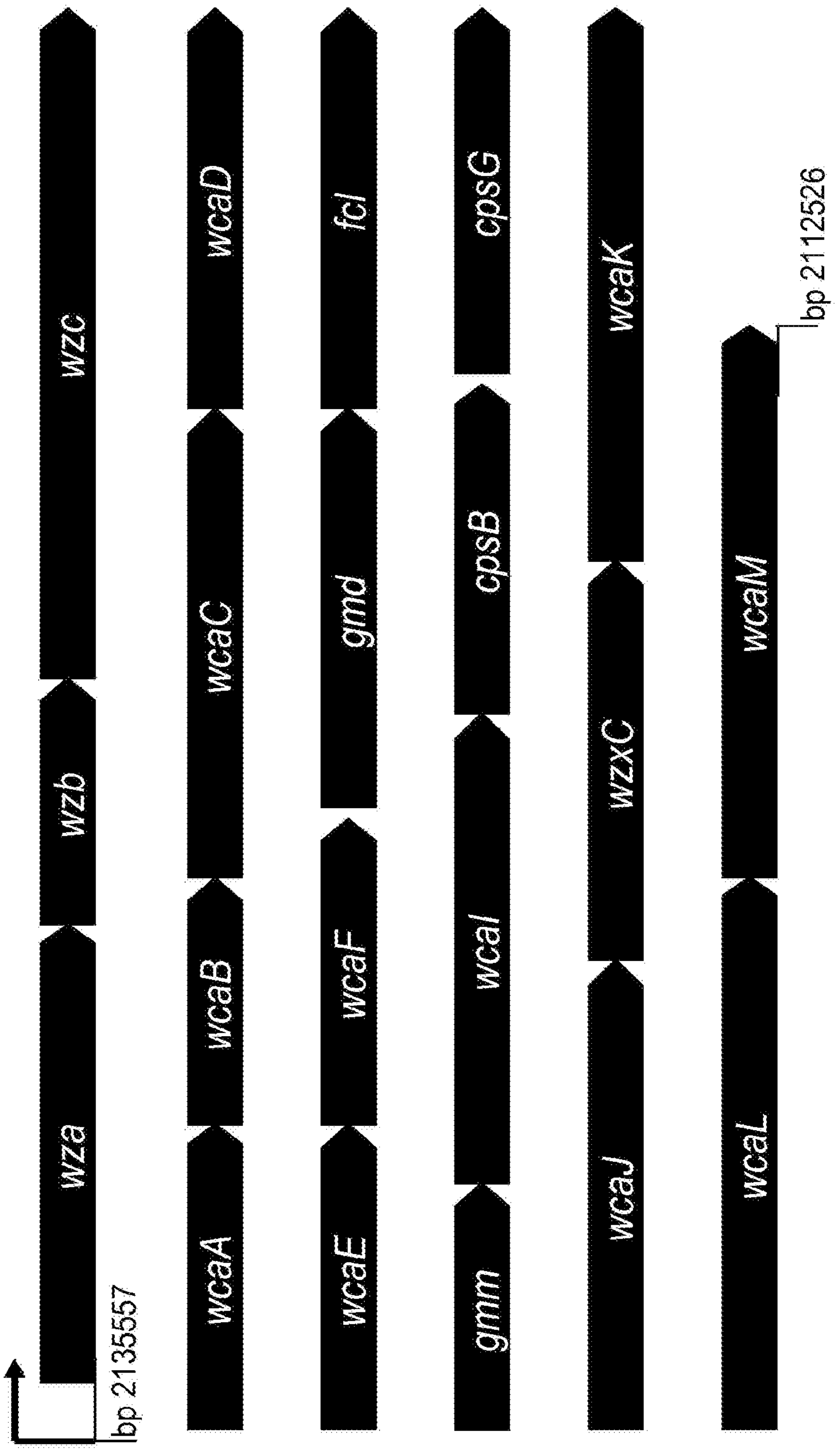
FIG. 3: The gene organisation of the colanic acid operon and an overview of the function of these genes.

The terms 'upregulating at least one of the genes of the colanic acid operon' indicates that the expression of at least 1, 2, 3, 4, . . . , or all of the genes belonging to the colanic acid operon are significantly (=P>0.05) upregulated when compared to the expression of said genes within a corresponding wild type microorganism which is cultivated under the same conditions as the mutated and/or transformed microorganism. The genes which belong to the colanic acid operon are wza, wzb, wzc, wcaA, wcaB, wcaC, wcaD, wcaE, wcaF, gmd, fcl, gmm, wcal, cpsB, cpsG, wcaJ, wzxC, wcaK, wcaL and wcaM as indicated in FIG. 3 and/or as described in (35). Furthermore, the gene rcsA, coding for the transcriptional regulator of the colanic acid operon is upregulated (13, 36). More specifically the terms 'upregulating at least one of the genes of the colanic acid operon' or the transcriptional regulator of the colanic acid operon indicates that at least one of the genes of the colanic acid operon is 6 to 8 times upregulated in comparison to the expression of the genes of the colanic acid operon in the corresponding wild type microorganism. In addition the present invention relates to upregulating genes of the colanic acid operon as described above by replacing the native promoter by an 'artificial promoter'. More specifically, the present invention relates to a combination of the sequence of the native promoter with sequences of other artificial promoter sequences. The combination of the sequence of the native promoter with the sequence of other artificial promoter sequences is more specifically the replacement of the sigma factor binding site of the native promoter with a stronger sigma factor binding site. Sigma factors, such as but not limited to sigma70, sigmaS, sigma24, . . . , are described (41), subunits of RNA polymerase that determine the affinity for promoter sequences and the transcription rate of genes. The present invention provides microorganisms which are genetically changed in such a manner that they can efficiently produce compounds which are part of the colanic acid pathway. The terms 'compounds which are part of the colanic acid pathway' refer to all compounds as indicated on FIG. 4 starting from fructose-6-P and resulting in extracellular colanic acid. More specifically the latter terms refer to the compounds mannose-6-P, mannose-1-P, GDP-mannose, GDP-4-dehydro-6deoxy-mannose, GDP-fucose and colanic acid. Hence the present invention specifically relates to the usage as indicated for the synthesis of colanic acid and/or for the synthesis of GDP-fucose. As GDP-fucose is a precursor for fucosylated oligosaccharides such as fucosyllactose, fucosyllactoNbiose and lewis X oligosaccharide or fucosylated proteins, and as these sugars have therapeutical, nutraceutical, anti-inflammatory and prebiotic effects, the present invention specifically relates to the usage as described above for the synthesis of fucosylated oligosaccharides. In other words, the present invention relates to a process for the synthesis of colanic acid and/or GDP-fucose and/or fucosylated oligosaccharides comprising genetically changing the transcriptional regulators the aerobic respiration control protein ArcA and the isocitrate lyase regulator IclR to upregulate at least one of the genes of the colanic acid operon, wherein said operon comprises the genes cpsG, cpsB, gmd and fcl or genes cpsG, cpsB, gmd, fcl and wza. More specifically, the present invention relates to a process as described wherein the mutations for ArcA and IclR are applied in combination with at least one mutation that enhances the production of fucosylated compounds. In order to efficiently produce fucosylated oligosaccharides (see FIGS. 1, 2 and 5-10), the above described mutations in arcA and iclR can be applied in combination with other mutations which further enhance the production of fucosylated compounds. Some of these—non-limiting—other mutations are: a) the deletion of wcaJ from the colanic operon, stopping the initiation of the colanic acid biosynthesis and thus allowing the accumulation of GDP-fucose; b) the introduction of a fucosyltransferase to link fucose with different acceptor molecules such as lactose; c) for the accumulation of the precursor of the GDP-fucose biosynthetic pathway and additional to the deletion of wcaJ, at least one of the following colanic acid operon genes that do not code for GDP-fucose biosynthesis is knocked out: gmm, wcaA, wcaB, wcaC, wcaD, wcaE, wcaF, wcal, wcaJ, wcaK, wcaL, wzx, wza, wzb, wzc, and/or, wcaM; d) for the production of fucosyllactose, lacZ coding for β-galactosidase, is knocked out to avoid lactose degradation; e) to accumulate the precursor fructose and fructose-6-phosphate, a sucrose phosphorylase or invertase is introduced; f) because fructose-6-phosphate is easily degraded in the glycolysis, the glycolysis has to be interrupted in order to steer all fructose-6-phosphate in the direction of GDP-fucose and the genes pgi, pfkA and pfkB (coding for glucose-6-phosphate isomerase and phosphofructokinase A and B) are thus knocked out; g) reducing protein degradation by knocking out a protease coded by a gene such as lon; h) By constitutively expressing a lactose permease, subpopulations are avoided in the production process which are common for lactose induced gene expression systems (19). In other words, the present invention relates to a process as described above for the synthesis of fucosylated oligosaccharides wherein said at least one mutation that enhance the production of fucosylated compounds is: the deletion of the wcaJ gene, and/or, knocking-out the colanic acid operon genes gmm, wcaA, wcaB, wcaC, wcaD, wcaE, wcaF, wcal, wcaJ, wcaK, wcaL, wzx, wza, wzb, wzc, and/or, wcaM, and/or, knocking-out lacZ, and/or, introducing a sucrose phosporylase or invertase, and/or, knocking out the genes pgi, pfkA and pfkB, and/or, knocking out the gene Ion, and/or introducing a fucosyltransferase, and/or a lactose permease. The term 'introducing a fucosyltransferase' relates to upregulating or heterologous expression of fucosyltransferases which are within, but not limited to the enzymes in enzyme classes classes EC2.4.1.65, 2.4.1.68, 2.4.1.69, 2.4.1.152, 2.4.1.214, and/or 2.4.1.221 and/or the glycosyltransferase families GT1, GT2, GT10 GT11, GT23, GT37, GT65, GT68, and/or GT74 and/or originating from but not limited to *Helicobacter pylori, Campylobacter jejuni, Dictyostellium discoideum, Mus musculus, Homo sapiens*, . . . and these fucosyltransferases catalyse the formation of α(1,2), α(1,3), α(1,4), or α(1,6) bonds on other sugars such as but not limited to galactose, lactose, lactoNbiose, lactoNtetraose, lactosamine, lactoNtetraose, sialyllactoses, disialyllactoses, or fucosylated proteins, or fucosylated fatty acids, or fucosylated aglycons such as, but not limited to, antivirals, antibiotics, . . . .

The present invention provides for the usage of a mutated and/or transformed microorganism comprising a genetic change leading to a modified expression and/or activity of the transcriptional regulators the aerobic respiration control protein ArcA and the isocitrate lyase regulator IclR to upregulate at least one of the genes of the colanic acid operon, wherein said operon comprises the genes cpsG and cpsB, coding for phosphomannomutase and mannose-1-phosphate guanylyltransferase, which are needed for the biosynthesis of GDP-mannose. As GDP-mannose is a precursor for mannosyllated oligosaccharides and mannosylated glycoconjugates. These oligosaccharides and glycoconjugates find for example applications in the treatment of gram-negative bacterial infections, in addition, GDP-mannose is important for the humanization of protein glycosylations, which is essential for the production of certain therapeutic proteins (18, 30). Mannosylated oligosaccharides and mannosylated glycoconjugates are also used for drug targeting, for instance mannosylated antivirals can specifically target the liver and kidneys (7). In order to efficiently produce mannosylated oligosaccharides (see FIGS. 1, 2, 5, 6 and 11), the above described mutations in arcA and iclR can be applied in combination with other mutations which further enhance the production of mannosylated compounds. Some of these—non-limiting—other mutations are: a) the gene gmd of the colanic acid operon is deleted, and/or, b) wherein the gene gmm coding for GDP-mannose hydrolase is deleted, and/or, c) wherein the colanic acid operon genes that do not code for GDP-mannose biosynthesis reactions, the genes gmm, wcaA, wcaB, wcaC, wcaD, wcaE, wcaF, wcal, wcaJ, wcaK, wcaL, fcl, gmd, wzx, wza, wzb and/or, wcaM, are deleted, and/or, d) wherein a gene encoding for a sucrose phosphorylase or an invertase is introduced, and/or, e) wherein the genes pgi, pfkA and pfkB, coding for phosphoglucose isomerase, phosphofructokinase A and phosphofructokinase B respectively, are deleted, and/or, f) knocking out the gene Ion encoding for a protease, and/or f) wherein a gene encoding for a mannosyltransferase is introduced. In other words, the present invention relates to a process as described above for the synthesis of colanic acid and/or GDP-fucose and/or fucosylated oligosaccharides for the synthesis of GDP-mannose and/or for the synthesis of mannosylated oligosaccharides. The present invention further relates to said process wherein the genes cpsG and cpsB of the colanic acid operon are upregulated and wherein: a) the gene gmd of the colanic acid operon is deleted, and/or, b) wherein the gene gmm is deleted, and/or c) wherein the colanic acid operon genes fcl, gmd, gmm, wcaA, wcaB, wcaC, wcaD, wcaE, wcaF, wcal, wcaJ, wcaK, wcaL, wzx, wza, wzb, wzc, and/or, wcaM are knocked out and/or, d) wherein a gene encoding for a sucrose phosphorylase or an invertase is introduced, and/or, e) wherein the genes pgi, pfkA and pfkB are deleted, and/or, f) knocking out the gene Ion, and/or g) wherein a gene encoding for a mannosyltransferase is introduced. The term 'introducing a mannosyltransferase' relates to upregulating or heterologous expression of mannosyltransferases which are within, but not limited to the enzymes in enzyme classes EC 2.4.1.32, 2.4.1.627, 2.4.1.644, 2.4.1.48, 2.4.1.54, 2.4.1.57, 2.4.1.83, 2.4.1.109, 2.4.1.110, 2.4.1.119, 2.4.1.130, 2.4.1.131, 2.4.1.132, 2.4.1.142, 2.4.1.199, 2.4.1.217, 2.4.1.232, 2.4.1.246, 2.4.1.251, 2.4.1.252, 2.4.1.257, 2.4.1.258, 2.4.1.259, 2.4.1.260, 2.4.1.265, and/or 2.4.1.270 and/or the glycosyltransferase families GT1, GT2, GT4, GT15, GT22, GT32, GT33, GT39, GT50 and/or GT58 and/or originating from but not limited to *Helicobacter pylori, Campylobacter jejuni, Dictyostellium discoideum, Mus musculus, Homo sapiens*, . . . and these mannosyltransferases catalyse the formation of α(1,2), α(1,3), α(1,4), or α(1,6) bonds on other sugars such as but not limited to galactose, N-acetylglucosamine, Rhamnose, lactose, lactoNbiose, lactoNtetraose, lactosamine, lactoNtetraose, sialyllactoses, disialyllactoses, or mannosylated proteins, or mannosylated fatty acids, or mannosylated aglycons such as, but not limited to, antivirals, antibiotics, . . . .

The term 'heterologous expression' relates to the expression of genes that are not naturally present in the production host, genes which can be synthesized chemically or be picked up from their natural host via PCR, genes which can be codon optimized for the production host or in which point mutation can be added to enhance enzyme activity or expression. Expressing heterologous and/or native genes can either be done on the chromosome, artificial chromosomes or plasmids and transcription can be controlled via inducible, constitutive, native or artificial promoters and translation can be controlled via native or artificial ribosome binding sites.

Consequently, the present invention further relates to mutated and/or transformed organisms in which the regulators ArcA and IclR as describe above, in combination with the genes encoding for the enzymes phosphoglucose isomerase and phosphofructokinase, are knocked out or are rendered less functional. More specifically, the present invention relates to the latter organisms wherein the enzyme phosphoglucose isomerase is encoded by the gene pgi and wherein the enzyme phosphofructokinase is encoded by the gene(s) pfkA and/or pfkB.

The terms 'genes which are rendered less-functional or non-functional' refer to the well-known technologies for a skilled person such as the usage of siRNA, RNAi, miRNA, asRNA, mutating genes, knocking-out genes, transposon mutagenesis, etc. . . . which are used to change the genes in such a way that they are less able (i.e. statistically significantly 'less able' compared to a functional wild-type gene) or completely unable (such as knocked-out genes) to produce functional final products. The term '(gene) knock out' thus refers to a gene which is rendered non-functional. The term 'deleted gene' or 'gene deletion' also refers to a gene which is rendered non-functional.

The present invention further relates to a mutated and/or transformed organism as described in the latter paragraph wherein said organism is further transformed with a gene encoding for a sucrose phosphorylase.

The present invention also relates to a mutated and/or transformed organism as described above wherein, in addition, the activity and/or expression of the gene encoding for a lactose permease is made constitutive and/or increased. Said activity can be increased by over-expressing said gene and/or by transforming said organisms with a gene encoding for a lactose permease.

The present invention further relates to any mutated and/or transformed organism as described above wherein at least one of the following genes is knocked out or is rendered less functional:

a gene encoding for a beta-galactosidase, a gene encoding for a glucose-1-phosphate adenylyltransferase, a gene encoding for a glucose-1-phosphatase, a gene encoding for phosphogluconate dehydratase, a gene encoding for 2-keto-3-deoxygluconate-6-phosphate aldolase, a gene encoding for a glucose-1-phosphate uridyltransferase, a gene encoding for an UDP-glucose-4-epimerase, a gene encoding for an UDP-glucose:galactose-1-phosphate uridyltransferase, a gene encoding for an UDP-galactopyranose mutase, a gene encoding for an UDP-galactose:(glucosyl)lipopolysaccharide-1,6-galactosyltransferase, a gene encoding for an UDP-galactosyltransferase, a gene encoding for an UDP-glucosyltransferase, a gene encoding for an UDP-glucuronate transferase, a gene encoding for an UDP-glucose lipid carrier transferase, a gene encoding for a GDP-mannose hydrolase, a gene encoding for an UDP-sugar hydrolase, a gene encoding for a mannose-6-phosphate isomerase, a gene encoding for an UDP-N-acetylglucosamine enoylpyruvoyl transferase, a gene encoding for an UDP-N-acetylglucosamine acetyltransferase, a gene encoding for an UDP-Nacetylglucosamine-2-epimerase, a gene encoding for an undecaprenyl-phosphate alfa-N-acetylglucosaminyl transferase, a gene encoding for a glucose-6-phosphate-1-dehydrogenase, and/or, a gene encoding for a L-glutamine:D-fructose-6-phosphate aminotransferase, a gene encoding for a mannose-6-phosphate isomerase, a gene encoding for a sorbitol-6-phosphate dehydrogenase, a gene encoding for a mannitol-1-phosphate 5-dehydrogenase, a gene encoding for a allulose-6-phosphate 3-epimerase, a gene encoding for an invertase, a gene encoding for a maltase, a gene encoding for a trehalase, a gene encoding for a sugar transporting phosphotransferase, a gene encoding for a protease, or a gene encoding for a hexokinase. The term 'at least one' indicated that at least 1, but also 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32 or all 33 genes is (are) knocked out or is (are) rendered less functional.

The present invention further relates also to the usage of a mutated and/or transformed microorganism such as an *Escherichia coli* strain comprising a genetic change leading to a modified expression of the transcriptional regulators the aerobic respiration control protein ArcA and the isocitrate lyase regulator IclR to upregulate at least one of the following acid resistance related genes: ydeP, ydeO, hdeA, hdeD, gadB, gadC, gadE, gadX, gadW and/or slp (17, 22). These genes are normally expressed in stationary phase conditions; however, the present mutated and/or transformed microorganism is able to enhance the expression of these acid resistance related genes in the exponential growth phase. Hence, the present invention relates to the usage as described above for the synthesis of acids or pH sensitive molecules such as but not limited to glucosamine which is pH sensitive and should be produced at low pH (12). Organic acids, such as but not limited to pyruvic acid, succinic acid, adipic, sialic acid, sialylated oligosaccharides (e.g. sialyllactose, sialyl Lewis X sugars, . . . ), acetylated oligosaccharides (chitins, chitosans, . . . ), sulfonated oligosaccharides (heparans and heparosans) . . . are preferably produced at low pH for downstream processing purposes (4). In other words, the present invention relates to a process for the synthesis of acids, sialic acid, sialylated oligosaccharides or glucosamine comprising genetically changing the transcriptional regulators the aerobic respiration control protein ArcA and the isocitrate lyase regulator IclR to upregulate at least one of the following acid resistance related genes: ydeP, ydeO, hdeA, hdeD, gadB, gadC, gadE, gadX, gadW and/or slp.

The present invention will now be illustrated by the following non-limiting examples.

EXAMPLES

A high throughput RT-qPCR screening of the microorganisms of the present invention has been setup with Biotrove OpenArray® technology. In this experiment the transcription of 1800 genes were measured in 4 strains (wild type, ΔarcA, ΔiclR, ΔarcA ΔiclR) in two conditions (chemostat and batch). The data was processed using a curve fitting toolbox in R (25, 34) and Quantile Normalization, the error on the data was calculated using Bayesian statistics (20, 21, 31).

Material and Methods

Strains and Plasmids

*Escherichia coli* MG1655 [$^-$, F$^-$, rph-1] was obtained from the Netherlands Culture Collection of Bacteria (NCCB). *Escherichia coli* BL21(DE3) was obtained from Novagen. *Escherichia coli* MG1655 ackA-pta, poxB, pppc ppc-p37 (10), the single knock-outs *E. coli* MG1655 arcA and *E. coli* MG1655 iclR and the double knock-out *E. coli* MG1655 arcA, iclR were constructed in the Laboratory of Genetics and Microbiology (MICR) using the method of Datsenko & Wanner (9).

Media

The Luria Broth (LB) medium consisted of 1% tryptone peptone (Difco, Erembodegem, Belgium), 0.5% yeast extract (Difco) and 0.5% sodium chloride (VWR, Leuven, Belgium). Shake flask medium contained 2 g/l $NH_4Cl$, 5 g/l $(NH_4)_2SO_4$, 2.993 g/l $KH_2PO_4$, 7.315 g/l $K_2HPO_4$, 8.372 g/l MOPS, 0.5 g/l NaCl, 0.5 g/l $MgSO_4.7H_2O$, 16.5 g/l glucose-$H_2O$, 1 ml/l vitamin solution, 100 μl/l molybdate solution, and 1 ml/l selenium solution. The medium was set to a pH of 7 with 1M KOH.

Vitamin solution consisted of 3.6 g/l $FeCl_2.4H_2O$, 5 g/l $CaCl_2.2H_2O$, 1.3 g/l $MnCl_2$. $2H_2O$, 0.38 g/l $CuCl_2.2H_2O$, 0.5 g/l $CoCl_2.6H_2O$, 0.94 g/l $ZnCl_2$, 0.0311 g/l $H_3BO_4$, 0.4 g/l $Na_2EDTA.2H_2O$ and 1.01 g/l thiamine.HCl. The molybdate solution contained 0.967 g/l $Na_2MoO_4.2H_2O$. The selenium solution contained 42 g/l $SeO_2$.

The minimal medium for fermentations contained 6.75 g/l $NH_4Cl$, 1.25 g/l $(NH_4)_2SO_4$, 1.15 g/l $KH_2PO_4$, 0.5 g/l NaCl, 0.5 g/l $MgSO_4.7H_2O$, 16.5 g/l glucose-$H_2O$, 1 ml/l vitamin solution, 100 μl/l molybdate solution, and 1 ml/l selenium solution with the same composition as described above.

Cultivation Conditions

A preculture, from a single colony on a LB-plate, in 5 ml LB medium was incubated during 8 hours at 37° C. on an orbital shaker at 200 rpm. From this culture, 2 ml was transferred to 100 ml minimal medium in a 500 ml shake flask and incubated for 16 hours at 37° C. on an orbital shaker at 200 rpm. 4% inoculum was used in a 2 l Biostat B Plus culture vessel with 1.5 I working volume (Sartorius Stedim Biotech, Melsungen, Germany). The culture conditions were: 37° C., stirring at 800 rpm, and a gas flow rate of 1.5 l/min. Aerobic conditions were maintained by sparging with air, anaerobic conditions were obtained by flushing the culture with a mixture of 3% $CO_2$ and 97% of $N_2$. The pH was maintained at 7 with 0.5 M $H_2SO4$ and 4 M KOH. The exhaust gas was cooled down to 4° C. by an exhaust cooler (Frigomix 1000, Sartorius Stedim Biotech, Melsungen, Germany). 10% solution of silicone antifoaming agent (BDH 331512K, VWR Int Ltd., Poole, England) was added when foaming raised during the fermentation (approximately 10 μl). The off-gas was measured with an EL3020 off-gas analyser (ABB Automation GmbH, 60488 Frankfurt am Main, Germany).

All data was logged with the Sartorius MFCS/win v3.0 system (Sartorius Stedim Biotech, Melsungen, Germany).

All strains were cultivated at least twice and the given standard deviations on yields and rates are based on at least 10 data points taken during the repeated experiments.

Sampling Methodology

The bioreactor contains in its interior a harvest pipe (BD Spinal Needle, 1.2×152 mm (BDMedical Systems, Franklin Lakes, N.J.—USA) connected to a reactor port, linked outside to a Masterflex-14 tubing (Cole-Parmer, Antwerpen, Belgium) followed by a harvest port with a septum for sampling. The other side of this harvest port is connected back to the reactor vessel with a Masterflex-16 tubing. This system is referred to as rapid sampling loop. During sampling, reactor broth is pumped around in the sampling loop. It has been estimated that, at a flow rate of 150 ml/min, the reactor broth needs 0.04 s to reach the harvest port and 3.2 s to re-enter the reactor. At a pO2 level of 50%, there is around 3 mg/l of oxygen in the liquid at 37° C. The pO2 level should never drop below 20% to avoid micro-aerobic conditions. Thus 1.8 mg/l of oxygen may be consumed during transit through the harvesting loop. Assuming an oxygen uptake rate of 0.4 g oxygen/g biomass/h (the maximal oxygen uptake rate found at $\mu_{max}$), this gives for 5 g/l biomass, an oxygen uptake rate of 2 g/l/h or 0.56 mg/l/s, which multiplied by 3.2 s (residence time in the loop) gives 1.8 mg/l oxygen consumption.

In order to quench the metabolism of cells during the sampling, reactor broth was sucked through the harvest port in a syringe filled with 62 g stainless steel beads pre-cooled at −20° C., to cool down 5 ml broth immediately to 4° C. Sampling was immediately followed by cold centrifugation (15000 g, 5 min, 4° C.). During the batch experiments, a sample for $OD_{600nm}$ and RT-qPCR measurements was taken using the rapid sampling loop and the cold stainless bead sampling method.

RT-qPCR mRNA was extracted with the RNeasy kit (Qiagen, Venlo, The Netherlands). RNA quality and quantity was checked with a nanodrop ND-1000 spectrophotometer (Nanodrop technologies, Wilmington, USA). The ratios 260:280 (nm) and 260:230 (nm) were between 1.8 and 2 and at least 100 ng/μl was needed for further analysis. cDNA was synthesised with random primers with the RevertAid™ H minus first strand cDNA synthesis kit (Fermentas, St. Leon-Rot, Germany). Finally, the gene expression of 1800 genes was measured with the Biotrove OpenArray Real time PCR platform. The primers for the RT-PCR assay were designed with Primer design tools from the Primer database (23).

The reaction mixture was composed as described in the Biotrove OpenArray™ Real-Time qPCR system users' manual. In short, a mastermix was made with 26.4 μl LightCycler® DNA Master SYBR® Green I (Roche applied Science), 1.1 μl SYBR GREEN I (100× stock solution, Sigma S9430), 8.8 μl glycerol (Sigma G5150), 5.3 μl Pluronic® F68 (10% stock, Invitrogen), 2.64 μl BSA (Sigma A7906), 26.4 μl magnesium chloride (25 mM stock solution, supplied in the LightCycler® kit of Roche applied Science), 21.1 μl HiDi™ formamide (Applied biosystems), and 94.66 μl RNase free sterile water resulting in a 186.4 μl mastermix, which is enough to load 1 OpenArray™. For 1 SubArray (each OpenArray is subdivided in 48 SubArrays on which 1 sample can be loaded) 1.5 μl sample (with a concentration of 100 ng/μl) was mixed with 3.5 μl of mastermind, as a no template control, water was used as blanc. The sample-mastermix mixture was loaded in a Loader plate (MatriPlate™ 384-well black low volume polypropylene plate, Biotrove) in a RNase free hood. A full loader plate was loaded with an AutoLoader (Biotrove) and loader tips onto the OpenArrays. These OpenArrays were then submerged in OpenArray™ immersion fluid in an OpenArray™ Real-Time qPCR case. The case was sealed with Case sealing glue and incubated in the Case Sealing station, which polymerizes the glue with UV light.

Analytical Methods

Cell density of the culture was frequently monitored by measuring optical density at 600 nm (Uvikom 922 spectrophotometer, BRS, Brussel, Belgium). Cell dry weight was obtained by centrifugation (15 min, 5000 g, GSA rotor, Sorvall RC-5B, Goffin Meyvis, Kapellen, Belgium) of 20 g reactor broth in pre-dried and weighted falcons. The pellets were subsequently washed once with 20 ml physiological solution (9 g/l NaCl) and dried at 70° C. to a constant weight. To be able to convert $OD_{600\ nm}$ measurements to biomass concentrations, a correlation curve of the $OD_{600\ nm}$ to the biomass concentration was made. The concentrations of glucose and organic acids were determined on a Varian Prostar HPLC system (Varian, Sint-Katelijne-Waver, Belgium), using an Aminex HPX-87H column (Bio-Rad, Eke, Belgium) heated at 65° C., equipped with a 1 cm precolumn, using 5 mM H2SO4 (0.6 ml/min) as mobile phase. A dual-wave UV-VIS (210 nm and 265 nm) detector (Varian Prostar 325) and a differential refractive index detector (Merck LaChrom L-7490, Merck, Leuven, Belgium) was used for peak detection. By dividing the absorptions of the peaks in both 265 and 210 nm, the peaks could be identified. The division results in a constant value, typical for a certain compound (formula of Beer-Lambert).

Glucose, fructose, sucrose, fucosyllactose and glucose-1-phosphate were measured by HPLC with a Hypercarb column and were detected with an MSMS detector (Antonio et al., 2007; Nielsen et al., 2006).

Genetic Methods

All mutant strains were constructed via the methods described below.

Plasmids were maintained in the host *E. coli* DH5α ($F^-$, φ80dlacZΔM15, Δ(lacZYA-argF)U169, deoR, recA1, endA1, hsdR17($rk^-$, $mk^+$), phoA, supE44, $\lambda^-$, thi-1, gyrA96, relA1).

Plasmids.

pKD46 (Red helper plasmid, Ampicillin resistance), pKD3 (contains an FRT-flanked chloramphenicol resistance (cat) gene), pKD4 (contains an FRT-flanked kanamycin resistance (kan) gene), and pCP20 (expresses FLP recombinase activity) plasmids were used for the mutant construction. The plasmid pBluescript (Fermentas, St. Leon-Rot, Germany) was used to construct the derivates of pKD3 and pKD4 with a promoter library, or with alleles carrying a point mutation.

Mutations.

The mutations consisted in gene disruption (knock-out, KO). They were introduced using the concept of Datsenko and Wanner (9). The primers for the mutation strategies are described in Table 1.

Transformants carrying a Red helper plasmid were grown in 10 ml LB media with ampicillin (100 mg/l) and L-arabinose (10 mM) at 30° C. to an $OD_{600nm}$ of 0.6. The cells were made electrocompetent by washing them with 50 ml of ice-cold water, a first time, and with 1 ml ice-cold water, a second time. Then, the cells were resuspended in 50 µl of ice-cold water. Electroporation was done with 50 µl of cells and 10-100 ng of linear double-stranded-DNA product by using a Gene Pulser™ (BioRad) (600 Ω, 25 µFD, and 250 volts).

After electroporation, cells were added to 1 ml LB media incubated 1 h at 37° C., and finally spread onto LB-agar containing 25 mg/l of chloramphenicol or 50 mg/l of kanamycin to select antibiotic resistant transformants. The selected mutants were verified by PCR with primers upstream and downstream of the modified region and were grown in LB-agar at 42° C. for the loss of the helper plasmid. The mutants were tested for ampicillin sensitivity.

Linear Double-Stranded-DNA.

The linear ds-DNA amplicons were obtained by PCR using pKD3, pKD4 and their derivates as template. The primers used had a part of the sequence complementary to the template and another part complementary to the side on the chromosomal DNA where the recombination has to take place (Table 1). For the KO, the region of homology was designed 50-nt upstream and 50-nt downstream of the start and stop codon of the gene of interest. For the KI, the transcriptional starting point (+1) had to be respected. PCR products were PCR-purified, digested with DpnI, repurified from an agarose gel, and suspended in elution buffer (5 mM Tris, pH 8.0).

Elimination of the Antibiotic Resistance Gene.

The selected mutants (chloramphenicol or kanamycin resistant) were transformed with pCP20 plasmid, which is an ampicillin and chloramphenicol resistant plasmid that shows temperature-sensitive replication and thermal induction of FLP synthesis. The ampicillin-resistant transformants were selected at 30° C., after which a few were colony purified in LB at 42° C. and then tested for loss of all antibiotic resistance and of the FLP helper plasmid. The gene knock outs and knock ins are checked with control primers (Fw/Rv-gene-out). These primers are given in Table 1.

TABLE 1

Primers used to create *E. coli* MG1655 arcA, *E. coli* MG1655 iclR and the double knock-out *E. coli* MG1655 arcA, iclR and all other genetic knock outs and knock ins

| Primer name | Sequence |
|---|---|
| lacZ | |
| FW_LacZ_P1 | CATAATGGATTTCCTTACGCGAAATACGGGCAGACATGGCCTGCCCGGTTATTAgtgtaggctggagctgcttc (SEQ ID No 7) |
| RV_LacZ_P2 | GTATGTTGTGTGGAATTGTGAGCGGATAACAATTTCACACAGGAAACAGCTcatatgaatatcctccttag (SEQ ID No 8) |
| FW_LacZ_out | GCGGTTGGAATAATAGCG (SEQ ID No 9) |
| RV_LacZ_out | CAGGTTTCCCGACTGGAAAG (SEQ ID No 10) |
| glgC | |
| FW-glgC-P1 | Agaccgccggttttaagcagcgggaacatctctgaacatacatgtaaaacctgcagtgtaggctggagctgcttc (SEQ ID No 11) |
| RV-glgC-P2 | Gtctggcagggacctgcacacggattgtgtgtgttccagagatgataaaaaaggagttagtccatatgaatatcctccttag (SEQ ID No 12) |
| FW-glgC-out | Gcgaatatcgggaaatgcagg (SEQ ID No 13) |
| RV-glgC-out | Cagagattgttttacctgctgg (SEQ ID No 14) |
| agp | |
| FW_agp_P1 | CATATTTCTGTCACACTCTTTAGTGATTGATAACAAAAGAGGTGCCAGGAgtgtaggctggagctgcttc (SEQ ID No 15) |
| RV_agp_P2 | TAAAAACGTTTAACCAGCGACTCCCCCGCTTCTCGCGGGGGAGTTTTCTGcatatgaatatcctccttag (SEQ ID No 16) |
| FW_agp_out | GCCACAGGTGCAATTATC (SEQ ID No 17) |
| RV_agp_out | CATTTTCGAAGTCGCCGGGTACG (SEQ ID No 18) |
| Pgi | |
| Fw-pgi-P1 | GGCGCTACAATCTTCCAAAGTCACAATTCTCAAAATCAGAAGAGTATTGCgtgtaggctggagctgcttc (SEQ ID No 19) |
| Rv-pgi-P2 | GGTTGCCGGATGCGGCGTGAACGCCTTATCCGGCCTACATATCGACGATGcatatgaatatcctccttag (SEQ ID No 20) |
| Fw_pgi_out (2) | GGCTCCTCCAACACCGTTAC (SEQ ID No 21) |
| Rv_pgi_out (2) | TACATATCGGCATCGACCTG (SEQ ID No 22) |

TABLE 1-continued

Primers used to create *E. coli* MG1655 arcA, *E. coli* MG1655 iclR and the double knock-out *E. coli* MG1655 arcA, iclR and all other genetic knock outs and knock ins

| Primer name | Sequence |
|---|---|
| pfkA | |
| Fw-pfkA-out | TACCGCCATTTGGCCTGAC (SEQ ID No 23) |
| Rv-pfkA-out | AAAGTGCGCTTTGTCCATGC (SEQ ID No 24) |
| Fw-pfkA-P1 | GACTTCCGGCAACAGATTTCATTTTGCATTCCAAAGTTCAGAGGTAGTCgtgtaggctg gagctgcttc (SEQ ID No 25) |
| Rv-pfkA-P2 | GCTTCTGTCATCGGTTTCAGGGTAAAGGAATCTGCCTTTTTCCGAAATCcatatgaata tcctccttag (SEQ ID No 26) |
| pfkB | |
| Fw-pfkB-out | TAGCGTCCCTGGAAAGGTAAC (SEQ ID No 27) |
| Rv-pfkB-out | TCCCTCATCATCCGTCATAG (SEQ ID No 28) |
| Fw-pfkB-P1 | CACTTTCCGCTGATTCGGTGCCAGACTGAAATCAGCCTATAGGAGGAAATGgtgtaggc tggagctgcttc (SEQ ID No 29) |
| Rv-pfkB-P2 | GTTGCCGACAGGTTGGTGATGATTCCCCCAATGCTGGGGGAATGTTTTTGcatatgaat atcctccttag (SEQ ID No 30) |
| arcA | |
| FW-arcA-P1 | Ggttgaaaaataaaaacggcgctaaaaagcgccgttttttttgacggtggtaaagccga gtgtaggctggagctgcttc (SEQ ID No 31) |
| RV-arcA-P2 | Ggtcagggacttttgtacttcctgtttcgatttagttggcaatttaggtagcaaaccat atgaatatcctccttag (SEQ ID No 32) |
| FW-arcA-out | Ctgccgaaaatgaaagccagta (SEQ ID No 33) |
| RV-arcA-out | Ggaaagtgcatcaagaacgcaa (SEQ ID No 34) |
| iclR | |
| FW-iclR-P1 | Ttgccactcaggtatgatgggcagaatattgcctctgcccgccagaaaaaggtgtaggc tggagctgcttc (SEQ ID No 35) |
| RV-iclR-P2 | Gttcaacattaactcatcggatcagttcagtaactattgcattagctaacaataaaaca tatgaatatcctccttag (SEQ ID No 36) |
| FW-iclR-out | Cggtggaatgagatcttgcga (SEQ ID No 37) |
| RV-iclR-out | Acttgctcccgacacgctca (SEQ ID No 38) |
| FW_iclR_P8 | TTGCCACTCAGGTATGATGGGCAGAATATTGCCTCTGCCCGCCAGAAAAAGccgcttac agacaagctgtg (SEQ ID No 39) |
| RV_iclR_P9 | GTTCAACATTAACTCATCGGATCAGTTCAGTAACTATTGCATTAGCTAACAATAAAAag ccatgacccgggaattac (SEQ ID No 40) |
| Rv-iclR-scarless KO stap 2 | CTATTGCATTAGCTAACAATAAAACTTTTTCTGGCGGGCAGAGG (SEQ ID No 41) |
| Fw-iclR-scarless KO stap 2 | CCTCTGCCCGCCAGAAAAAGTTTTATTGTTAGCTAATGCAATAGTTAC (SEQ ID No 42) |
| wcaJ | |
| Fw_wcaJ_out | GCCAGCGCGATAATCACCAG (SEQ ID No 43) |
| Rv_wcaJ_out | TGCGCCTGAATGTGGAATC (SEQ ID No 44) |
| Fw-wcaJ_2-P1 | TTTTGATATCGAACCAGACGCTCCATTCGCGGATGTACTCAAGGTCGAACgtgtaggct ggagctgcttc (SEQ ID No 45) |
| Rv-wcaJ_2-P2 | TCTATGGTGCAACGCTTTTCAGATATCACCATCATGTTTGCCGGACTATGcatatgaat atcctccttag (SEQ ID No 46) |
| fw_wcaJ_H1' | TCAATATGCCGCTTTGTTAACGAAACCTTTGAACACCGTCAGGAAAACGATTTTGATAT CGAACCAGACG (SEQ ID No 47) |
| Rv_wcaJ_H2' | TGACAAATCTAAAAAAGCGCGAGCGAGCGAAAACCAATGCATCGTTAATCTCTATGGTG CAACGCTTTTC (SEQ ID No 48) |
| Fw_wcaJ_H1'_2 | CGCTTTGTTAACGAAACCTTTGAACACCGTCAGGAAAACGATTTTGATATCGAACCAGA CGCTCCATTCG (SEQ ID No 49) |
| Ion | |
| FW-lon-P1 | CAGTCGTGTCATCTGATTACCTGGCGGAAATTAAACTAAGAGAGAGCTCTgtgtaggct ggagctgcttc (SEQ ID No 50) |
| oMEMO100_RV-lon-P2 | CGAATTAGCCTGCCAGCCCTGTTTTTATTAGTGCATTTTGCGCGAGGTCAcatatgaat atcctccttag (SEQ ID No 51) |
| oMEMO101_FW-lon-out | AGCGCAACAGGCATCTGGTG (SEQ ID No 52) |
| oMEMO102_RV-lon-out | TATATCAGGCCAGCCATCCC (SEQ ID No 53) |

TABLE 1-continued

Primers used to create *E. coli* MG1655 arcA, *E. coli* MG1655 iclR and the double knock-out *E. coli* MG1655 arcA, iclR and all other genetic knock outs and knock ins

| Primer name | Sequence |
|---|---|
| lacZYA:P22-lacY | |
| Fw_lacZYA__chl | GCTGAACTTGTAGGCCTGATAAGCGCAGCGTATCAGGCAATTTTTATAATCTTCATTTAAATGGCGCGC (SEQ ID No 54) |
| rv_lacZYA_chl | GCGCAACGCAATTAATGTGAGTTAGCTCACTCATTAGGCACCCCAGGCTTCGCCTACCTGTGACGGAAG (SEQ ID No 55) |
| fw_P22lacY-KI_P1 | GCGCAACGCAATTAATGTGAGTTAGCTCACTCATTAGGCACCCCAGGCTTGTGTAGGCTGGAGCTGCTTC (SEQ ID No 56) |
| rv_P22lacY-KI | GCTGAACTTGTAGGCCTGATAAGCGCAGCGTATCAGGCAATTTTTATAATCTTAAGCGACTTCATTCACC (SEQ ID No 57) |
| fw_lacZYA_H1' | CGACGCTTGTTCCTGCGCTTTGTTCATGCCGGATGCGGCTAATGTAGATCGCTGAACTTGTAGGCCTG (SEQ ID No 58) |
| rv_lacZYA_H2' | CATTAATGCAGCTGGCACGACAGGTTTCCCGACTGGAAAGCGGGCAGTGAGCGCAACGCAATTAATGTG (SEQ ID No 59) |
| pfkA:P22-BaSP | |
| Fw-pfkA-P1 | GACTTCCGGCAACAGATTTCATTTTGCATTCCAAAGTTCAGAGGTAGTCgtgtaggctggagctgcttc (SEQ ID No 60) |
| Rv-pfkA-pCXP22_P2 | GCTTCTGTCATCGGTTTCAGGGTAAAGGAATCTGCCTTTTTCCGAAATCaagcttgcatgcctgcatcc (SEQ ID No 61) |
| FW_kan | AGAGGCTATTCGGCTATGAC (SEQ ID No 62) |
| Fw_baSP_seq | CGCCATGTTGGAATGGGAGG (SEQ ID No 63) |
| Fw_pfkA_H1-ext | TGATTGTTATACTATTTGCACATTCGTTGGATCACTTCGATGTGCAAGAAGACTTCCGGCAACAGATTTC (SEQ ID No 64) |
| Rv_pfkA_H2_ext | AATTGCAGAATTCATGTAGGCCTGATAAGCGAAGCGCATCAGGCATTTTTGCTTCTGTCATCGGTTTCAG (SEQ ID No 65) |
| Fw-pfkA-out | TACCGCCATTTGGCCTGAC (SEQ ID No 66) |
| Rv-pfkA-out | AAAGTGCGCTTTGTCCATGC (SEQ ID No 67) |
| adhE:P22-frk | |
| Fw-adhE-pCXP22-P1 | ATCGGCATTGCCCAGAAGGGGCCGTTTATGTTGCCAGACAGCGCTACTGAgtgtaggctggagctgcttc (SEQ ID No 68) |
| Rv-adhE-pCXP22-P2 | ATTCGAGCAGATGATTTACTAAAAAAGTTTAACATTATCAGGAGAGCATTaagcttgcatgcctgcatcc (SEQ ID No 69) |
| Fw-adhE-H1' | AAGCCGTTATAGTGCCTCAGTTTAAGGATCGGTCAACTAATCCTTAACTGATCGGCATTGCCCAGAAG (SEQ ID No 70) |
| Rv-adhE-H2' | TTGATTTTCATAGGTTAAGCAAATCATCACCGCACTGACTATACTCTCGTATTCGAGCAGATGATTTACTAAAAAAG (SEQ ID No 71) |
| FW_adhE_out | GCGTCAGGCAGTGTTGTATC (SEQ ID No 72) |
| RV_adhE_out | CTGGAAGTGACGCATTAGA (SEQ ID No 73) |
| ldhA:P14-FT_*H. pylori* | |
| FW_ldhA_out | tgtcattacttacacatcccgc (SEQ ID No 74) |
| RV_ldhA_out | gcattcaatacgggtattgtgg (SEQ ID No 75) |
| Fw-ldhA-pCXP22_P1 | CATTGGGGATTATCTGAATCAGCTCCCCTGGAATGCAGGGGAGCGGCAAGgtgtaggctggagctgcttc (SEQ ID No 76) |
| Rv-ldhA-pCXP22_P2 | TATTTTTAGTAGCTTAAATGTGATTCAACATCACTGGAGAAAGTCTTATGaagcttgcatgcctgcatcc (SEQ ID No 77) |
| Fw-ldhA-H1' | CAATTACAGTTTCTGACTCAGGACTATTTTAAGAATAGAGGATGAAAGGTCATTGGGGATTATCTGAATCAG (SEQ ID No 78) |
| Rv-ldhA-H2' | GAATTTTTCAATATCGCCATAGCTTTCAATTAAATTTGAAATTTTGTAAAATATTTTTAGTAGCTTAAATGTGATTCAAC (SEQ ID No 79) |
| Fw-ldhA-long homol | TTCACCGCTAAAGCGGTTAC (SEQ ID No 80) |
| Rv-ldhA-long homol | CGCGTAATGCGTGGGCTTTC (SEQ ID No 81) |

TABLE 1-continued

Primers used to create *E. coli* MG1655 arcA, *E. coli* MG1655 iclR and the double knock-out *E. coli* MG1655 arcA, iclR and all other genetic knock outs and knock ins

| Primer name | Sequence |
|---|---|
| promCA:P14 | |
| pCXP14_SP_Fw | CCGGCATATGGTATAATAGGG (SEQ ID No 82) |
| yegH_rc_pure_rv | ACGGCTTGCTGGCCATCA (SEQ ID No 83) |
| fw_P14-CA_KI_tetA | CGAATATAAGGTGACATTATGGTAATTGAATATTGGCTTTCCAATAATGCTACGGCCCCAAGGTCCAA (SEQ ID No 84) |
| rv_P14-CA_KI_tetA | AATATTGTCAACCTAAAGAAACTCCTAAAAACCATATTGAATGACACTTATTGGCTTCAGGGATGAGGCG (SEQ ID No 85) |
| fw_P14-CA_KI_overlapA | TCCCGACTACGTGGACCTTG (SEQ ID No 86) |
| rv_P14-CA_KI overlapA | CATATGGTATAATAGGGAAATTTCCATGGCGGCCGCTCTAGAAGAAGCTTGGGATCCGTCGACCTCGGCATTATTGGAAAGCCAATATTC (SEQ ID No 87) |
| fw_P14-CA_KI_overlapB | GCCGCCATGGAAATTTCCCTATTATACCATATGCCGGCCAAGATGTCAAGAAACTTATAGAATGAAGTAAGTGTCATTCAATATGG (SEQ ID No 88) |
| fw_P14-CA_KI_H1 | AATATTGTCAACCTAAAGAAACTCCTAAAAACCATATTGAATGACACTTACTTCATTCTATAAGTTTCTTGAC (SEQ ID No 89) |
| rv_P14-CA_KI_H2 | CGAATATAAGGTGACATTATGGTAATTGAATATTGGCTTTCCAATAATGCCGAGGTCGACGGATCCCAAGCTTC (SEQ ID No 90) |

Transformation.

Plasmids were transformed in $CaCl_2$ competent cells using the simplified procedure of Hanahan (16) or via electroporation as described above.

Calculation Methods

Introduction

Different experiments with different strains were performed. In total 8 different conditions were tested. There was variation in the genetic background (WT, iclR knock-out, arcA knock-out, and combined iclR-arcA knock-out) and the mode of fermentation (batch, and chemostat). Each experiment was repeated twice.

When running the samples through the BioTrove apparatus, a qPCR curve (fluorescences in function of cycle number) and a melt curve (fluorescences in function of the temperature) is obtained for each sample. Those data were exported from the BioTrove software and further analysed in R. The analysis was divided in two steps: first the qPCR curves were fitted and Ct values were calculated and in the second step the Ct values were converted to expression data.

Calculating the qPCR Curves

The raw qPCR curve data were extracted from the BioTrove software and imported in R (1). The curves were fitted to a 5 parameter sigmoidal model, with the R package qPCR (25, 34). The maximum of the second derivative of those curves was used as Ct value. No normalisation was applied to the data prior to the curve fitting. However, outliers were removed. The detection of the outliers was done using the following procedure:

Fit the model to the data.

Calculate the residuals (defined as the measured fluorescences minus the model-calculated ones).

Assuming the residuals are normally distributed, calculate the mean and standard deviation of the residuals.

Using this mean and standard deviation, the 95% interval is calculated.

All data-points for which the residuals fall out of this 95% interval are considered as outliers.

The curve is refitted without the outliers.

This is repeated until no outliers are detected anymore.

Using this procedure, the data do not have to be normalised prior to fitting, neither must the first data-points be removed.

Many curves have to be fitted (1800 genes for one experiment). Therefore, it is undoable to manually check each curve and automated methods have to be applied to reject bad curves. For this different parameters are extracted from the curves: the cycle number value at which the maximum of the first derivative occurs (D1), the cycle number value at which the maximum of the second derivative occurs (D2), the minimal fluorescence (Fmin), and the maximal fluorescence (Fmax). Combining the values of those parameters, the validity of the curve and the extent of expression is assessed. How this is done is explained in the next section.

Filtering the Data

For some gene-experiment combinations, no amplification is detected. This can be due to a variety of reasons:

Expression is too low and 32 cycles (the number of cycles for all BioTrove arrays was set to 32) is not enough to detect the expression. In this case, the real Ct cannot be determined and is somewhere between 32 and infinity.

No expression. In this case, the real Ct is infinite.

Technical failures: primers not suitable, wrong loading (it is very difficult to uniformly load the BioTrove arrays, especially the holes at the sides of the array are frequently empty), etc. In this case the real Ct can vary between 0 and infinity.

Some genes are genuinely not expressed and setting their Ct value to something else than infinity is not correct. For genes that are expressed, but for which the expression value, due to technical failures or limitations, are not known, setting the Ct value to infinity is not correct. Furthermore, using arbitrary values that are outside the range of expression complicates the calculation routines and visualisation routines. Therefore it was opted to remove the gene-experiment combinations for which no correct expression data was detected.

An obvious case of gene-experiment pairs for which no expression is detected, are those for which no curve could be fitted to the qPCR data. Less obvious cases are detailed below.

Typically for expressed genes, is that the fluorescence values cover a certain range. Data points for which this range was not high enough, were discarded, as they pointed to very poorly fitted curves and generally bad data. The minimal fluorescence range was set to 400 (thus Fmax−Fmin>400).

In a good amplification curve, the first (D1) and second (D2) derivative are quite close to each other (see the documentation of the SOD function in the qpcR package (25)). Therefore, all data-points for which the difference between D1 and D2 is larger than an arbitrary value (7 was used) were discarded.

For each primer-pair, a qPCR experiment was performed without adding DNA. Only water was added. Normally no expression should be observed in those samples. However, amplification is detected in water for some primer-pairs. Genes for which the Ct value (as mentioned before, D2 was used) is more than the Ct value of water minus 5, are discarded, as it cannot be excluded that the fluorescence comes from the amplification of the primers and not the added DNA.

Normalising and Calculating the Contrasts

Prior to calculating the expression differences, the Ct values have to be normalised. As so many genes were measured (1800), quantile normalisation could be used (33). The 1800 genes measured, were divided over 3 types of arrays, each containing 600 genes.

Quantile normalisation was done for each type of array separately. A table was constructed where the rows represent the different genes and the columns the different experiments (T1, see Equations 1). Each column was sorted independently (T2) and the original position of the elements was saved. The values in this new table were replaced with the mean value over the different rows (T3). And finally this table was transformed so that the positions of the values corresponded again to the original positions (T4).

$$T_1 = \begin{bmatrix} 2 & 4 \\ 6 & 8 \\ 4 & 12 \end{bmatrix}$$

$$T_2 = \begin{bmatrix} 2 & 4 \\ 6 & 8 \\ 4 & 12 \end{bmatrix}$$

$$T_3 = \begin{bmatrix} 3 & 3 \\ 6 & 6 \\ 9 & 9 \end{bmatrix}$$

$$T_3 = \begin{bmatrix} 3 & 3 \\ 6 & 6 \\ 9 & 9 \end{bmatrix}$$

Equations 1: Example of Quantile Normalisation

Differential expressions were calculated with the normalised data. This was done with the R package limma, which uses a Bayesian approach to calculate the statistical relevances of the differences (31, 32). Limma was adapted to be able to cope with missing data: the original limma package discards all expression values from a gene over the different experiments, when one value in one experiment is not available. This hampers the analysis when one has many different conditions, as for each gene for which one of the experimental conditions produces no expression values, a different contrast matrix has to be generated omitting that experimental condition. Therefore the function for fitting the contrasts was adapted to drop data-points with missing data.

Differential expressions were calculated between Ct values and the mean Ct value for a certain gene. Thus, the higher the value, the lower the expression. For each gene, plots were generated showing those differences. However, in those plots, the Ct values were inversed, so that the higher the value, the higher the expression.

Figure 1:
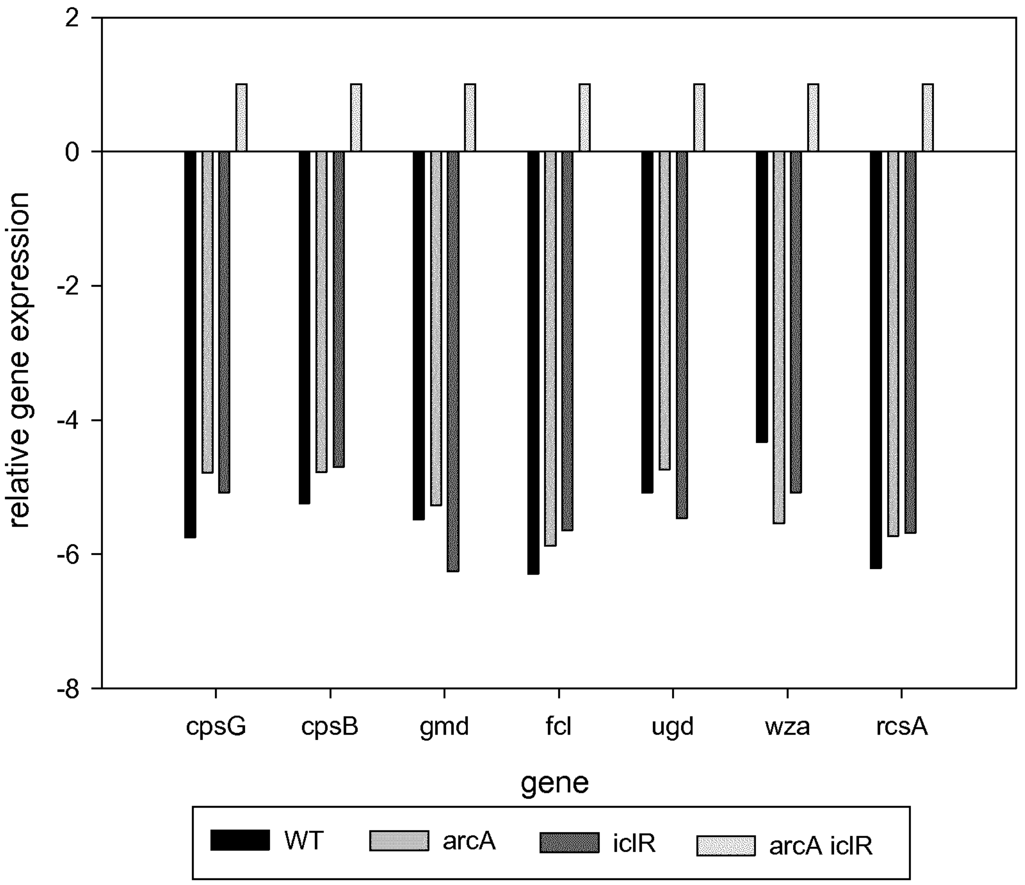
FIG. 1: Relative gene expression pattern of the wild type, the ΔiclR and ΔarcA mutant strain to the ΔarcAΔiclR mutant strain of genes involved in colanic acid biosynthesis in batch fermentation conditions. The genes involved in colanic acid biosynthesis are presented in FIGS. 3 and 4.

Example 1: Effect of arcA and iclR gene deletions on the gene expression of the colanic acid biosynthesis FIGS. 1 and 2 show the expression pattern of genes involved in colanic acid biosynthesis (35). Single arcA or iclR knock out mutations did not affect the expression of the operon in comparison of the wild type strain in batch and chemostat conditions. The double mutant strain, ΔarcAΔiclR, however upregulates the genes of the colanic acid operon 6 to 8 times in comparison to the wild type and the single mutant strains in both chemostat and batch conditions. Both regulators have thus a surprisingly cooperative effect on the expression of this operon which is independent from the culturing condition that is applied. Looking at the regulatory network of this operon, no direct link could be found between both ArcA and IclR and the transcription factor that controls the operon, RcsA (FIG. 5). Only ArcA is connected with RcsA via 3 other transcription factors, which are all upregulated as well. However the ΔarcA single gene deletion mutant strain did not affect the transcription of the operon.

Example 2: Effect of arcA and iclR Gene Deletions on the Gene Expression of the GDP-Fucose Biosynthesis Genes FIGS. 4 and 6 show the relationship of the colanic acid operon with GDP-fucose biosynthesis. In FIG. 6 the upregulation of GDP-fucose biosynthesis specific genes is shown. These mutations thus enhance the biosynthesis of GDP-fucose, which is a precursor for fucosylated oligosaccharides such as fucosyllactose, fucosyllactoNbiose and lewis X oligosaccharide or fucosylated proteins. These sugars and proteins, as already indicated above, have applications in therapeutics as nutraceutical, as components in human mother milk in which they have anti-inflammatory and prebiotic effects (5, 8, 27).

Example 3: Enhancement of GDP-Fucose and Fucosylated Oligosaccharide Biosynthesis The mutations ΔarcAΔiclR applied in combination with other mutations enhance the production of fucosylated compounds. A first, 'other' genetic modification that enhances said production is the deletion of wcaJ from the colanic operon, stopping the initiation of the colanic acid biosynthesis and thus the accumulation of GDP-fucose. Further, a fucosyltransferase has to be introduced to link fucose with different acceptor molecules such as lactose. The metabolism is then engineered further to accumulate the precursor of the GDP-fucose biosynthetic pathway. These modifications are shown in FIG. 7. Additional to wcaJ, the colanic acid operon genes that do not code for GDP-fucose biosynthesis reactions are knocked out, such as gmm, wcaA, wcaB, wcaC, wcaD, wcaE, wcaF, wcaI, wcaK, wcaL and/or, wcaM. For the production of fucosyllactose, lacZ coding for β-galactosidase, is knocked out to avoid lactose degradation and the expression of lacY, coding for a lactose permease, is enhanced by means of a strong constitutive promoter.

Example 4: Enhancement of GDP-Fucose and Fucosylated Oligosaccharide Production Via a Split Metabolism with Sucrose as a Substrate To accumulate the GDP-fucose precursor fructose and fructose-6-phosphate, a sucrose phosphorylase or invertase is introduced. Because fructose-6-phosphate is easily degraded in the glycolysis, the glycolysis is interrupted in order to steer all fructose-6-phosphate in the direction of GDP-fucose. The genes pgi, pfkA and pfkB are thus knocked out, coding for glucose-6-phosphate isomerase and phosphofructokinase A and B. Finally a fucosyltransferase is introduced to link fucose to an acceptor molecule.

The growth rate of the wild type strain is somewhat affected when grown on sucrose after introduction of a sucrose phosphorylase (BaSP) (plasmid with sequence SEQ ID No 2) (Table 2), however the introduction of pgi mutations and pfkA and pfkB double mutations led to significant reduction of growth rate, the latter was extremely low (0.02 $h^{-1}$). The combination of all mutations (Δpgi and ΔpfkA and ΔpfkB) led to the lowest growth rate, however, the growth rate on both sucrose and glucose was surprisingly similar to that of the pgi single mutant.

TABLE 2 specific growth rates of the glycolysis knock out strains on a minimal medium with glucose and sucrose

| Strain | Growth rate on glucose ($h^{-1}$) | Growth rate on sucrose ($h^{-1}$) (strains transformed with plasmid containing BaSP) |
|---|---|---|
| Wild type | 0.64 | 0.41 |
| Δpgi | 0.18 | 0.23 |
| ΔpfkAΔpfkB | 0.02 | n.d. |
| ΔpgiΔpfkAΔpfkB | 0.23 | 0.24 |

SEQ ID No 2: Plasmid Sequence with Sucrose Phosphorylase BaSP

AATTCGGAGGAAACAAAGATGGGGGGTTCTCATCATCATCATCATCATGG

TATGGCTAGCATGAAAAACAAGGTGCAGCTCATCACTTACGCCGACCGCC

TTGGCGACGGCACCATCAAGTCGATGACCGACATTCTGCGCACCCGCTTC

GACGGCGTGTACGACGGCGTTCACATCCTGCCGTTCTTCACCCCGTTCGA

CGGCGCCGACGCAGGCTTCGACCCGATCGACCACACCAAGGTCGACGAAC

GTCTCGGCAGCTGGGACGACGTCGCCGAACTCTCCAAGACCCACAACATC

ATGGTCGACGCCATCGTCAACCACATGAGTTGGGAATCCAAGCAGTTCCA

GGACGTGCTGGCCAAGGGCGAGGAGTCCGAATACTATCCGATGTTCCTCA

CCATGAGCTCCGTGTTCCCGAACGGCGCCACCGAAGAGGACCTGGCCGGC

ATCTACCGTCCGCGTCCGGGCCTGCCGTTCACCCACTACAAGTTCGCCGG

-continued

CAAGACCCGCCTCGTGTGGGTCAGCTTCACCCCGCAGCAGGTGGACATCG

ACACCGATTCCGACAAGGGTTGGGAATACCTCATGTCGATTTTCGACCAG

ATGGCCGCCTCTCACGTCAGCTACATCCGCCTCGACGCCGTCGGCTATGG

CGCCAAGGAAGCCGGCACCAGCTGCTTCATGACCCCGAAGACCTTCAAGC

TGATCTCCCGTCTGCGTGAGGAAGGCGTCAAGCGCGGTCTGGAAATCCTC

ATCGAAGTGCACTCCTACTACAAGAAGCAGGTCGAAATCGCATCCAAGGT

GGACCGCGTCTACGACTTCGCCCTGCCTCCGCTGCTGCTGCACGCGCTGA

GCACCGGCCACGTCGAGCCCGTCGCCCACTGGACCGACATACGCCCGAAC

AACGCCGTCACCGTGCTCGATACGCACGACGGCATCGGCGTGATCGACAT

CGGCTCCGACCAGCTCGACCGCTCGCTCAAGGGTCTCGTGCCGGATGAGG

ACGTGGACAACCTCGTCAACACCATCCACGCCAACACCCACGGCGAATCC

CAGGCAGCCACTGGCGCCGCCGCATCCAATCTCGACCTCTACCAGGTCAA

CAGCACCTACTATTCGGCGCTCGGGTGCAACGACCAGCACTACATCGCCG

CCCGCGCGGTGCAGTTCTTCCTGCCGGGCGTGCCGCAAGTCTACTACGTC

GGCGCGCTCGCCGGCAAGAACGACATGGAGCTGCTGCGTAAGACGAATAA

CGGCCGCGACATCAATCGCCATTACTACTCCACCGCGGAAATCGACGAGA

ACCTCAAGCGTCCGGTCGTCAAGGCCCTGAACGCGCTCGCCAAGTTCCGC

AACGAGCTCGACGCGTTCGACGGCACGTTCTCGTACACCACCGATGACGA

CACGTCCATCAGCTTCACCTGGCGCGGCGAAACCAGCCAGGCCACGCTGA

CGTTCGAGCCGAAGCGCGGTCTCGGTGTGGACAACGCTACGCCGGTCGCC

ATGTTGGAATGGGAGGATTCCGCGGGAGACCACCGTTCGGATGATCTGAT

CGCCAATCCGCCTGTCGTCGCCTGACTGCAGGTCGACCATATGGGAGAGC

TCCCAACGCGTTGGATGCAGGCATGCAAGCTTGGCTGTTTTGGCGGATGA

GAGAAGATTTTCAGCCTGATACAGATTAAATCAGAACGCAGAAGCGGTCT

GATAAAACAGAATTTGCCTGGCGGCAGTAGCGCGGTGGTCCCACCTGACC

CCATGCCGAACTCAGAAGTGAAACGCCGTAGCGCCGATGGTAGTGTGGGG

TCTCCCCATGCGAGAGTAGGGAACTGCCAGGCATCAAATAAAACGAAAGG

CTCAGTCGAAAGACTGGGCCTTTCGTTTTATCTGTTGTTTGTCGGTGAAC

GCTCTCCTGAGTAGGACAAATCCGCCGGGAGCGGATTTGAACGTTGCGAA

GCAACGGCCCGGAGGGTGGCGGGCAGGACGCCCGCCATAAACTGCCAGGC

ATCAAATTAAGCAGAAGGCCATCCTGACGGATGGCCTTTTTGCGTTTCTA

CAAACTCTTTTTGTTTATTTTTCTAAATACATTCAAATATGTATCCGCTC

ATGAGACAATAACCCTGATAAATGCTTCAATAATATTGAAAAAGGAAGAG

TATGAGTATTCAACATTTCCGTGTCGCCCTTATTCCCTTTTTTGCGGCAT

TTTGCCTTCCTGTTTTTGCTCACCCAGAAACGCTGGTGAAAGTAAAAGAT

GCTGAAGATCAGTTGGGTGCACGAGTGGGTTACATCGAACTGGATCTCAA

CAGCGGTAAGATCCTTGAGAGTTTTCGCCCCGAAGAACGTTTTCCAATGA

TGAGCACTTTTAAAGTTCTGCTATGTGGCGCGGTATTATCCCGTGTTGAC

GCCGGGCAAGAGCAACTCGGTCGCCGCATACACTATTCTCAGAATGACTT

GGTTGAGTACTCACCAGTCACAGAAAAGCATCTTACGGATGGCATGACAG

TAAGAGAATTATGCAGTGCTGCCATAACCATGAGTGATAACACTGCGGCC

-continued

```
AACTTACTTCTGACAACGATCGGAGGACCGAAGGAGCTAACCGCTTTTTT
GCACAACATGGGGGATCATGTAACTCGCCTTGATCGTTGGGAACCGGAGC
TGAATGAAGCCATACCAAACGACGAGCGTGACACCACGATGCCTACAGCA
ATGGCAACAACGTTGCGCAAACTATTAACTGGCGAACTACTTACTCTAGC
TTCCCGGCAACAATTAATAGACTGGATGGAGGCGGATAAAGTTGCAGGAC
CACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAA
CTATGGATGAACGAAATAGACAGATCGCTGAGATAGGTGCCTCACTGATT
AAGCATTGGTAACTGTCAGACCAAGTTTACTCATATATACTTTAGATTGA
TTTAAAACTTCATTTTTAATTTAAAAGGATCTAGGTGAAGATCCTTTTTG
ATAATCTCATGACCAAAATCCCTTAACGTGAGTTTTCGTTCCACTGAGCG
TCAGACCCCGTAGAAAAGATCAAAGGATCTTCTTGAGATCCTTTTTTTCT
GCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGC
TTCAGCAGAGCGCAGATACCAAATACTGTCCTTCTAGTGTAGCCGTAGTT
AGGCCACCACTTCAAGAACTCTGTAGCACCGCCTACATACCTCGCTCTGC
TAATCCTGTTACCAGTGGCTGCTGCCAGTGGCGATAAGTCGTGTCTTACC
GGGTTGGACTCAAGACGATAGTTACCGGATAAGGCGCAGCGGTCGGGCTG
AACGGGGGGTTCGTGCACACAGCCCAGCTTGGAGCGAACGACCTACACCG
AACTGAGATACCTACAGCGTGAGCTATGAGAAAGCGCCACGCTTCCCGAA
GGGAGAAAGGCGGACAGGTATCCGGTAAGCGGCAGGGTCGGAACAGGAGA
GCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTT
CCTGGCCTTTTGCTGGCCTTTTGCTCACATGTTCTTTCCTGCGTTATCCC
CTGATTCTGTGGATAACCGTATTACCGCCTTTGAGTGAGCTGATACCGCT
CGCCGCAGCCGAACGACCGAGCGCAGCGAGTCAGTGAGCGAGGAAGCGGA
AGAGCGCCTGATGCGGTATTTTCTCCTTACGCATCTGTGCGGTATTTCAC
ACCGCATATGGTGCACTCTCAGTACAATCTGCTCTGATGCCGCATAGTTA
AGCCAGTATACACTCCGCTATCGCTACGTGACTGGGTCATGGCTGCGCCC
CGACACCCGCCAACACCCGCTGACGCGCCCTGACGGGCTTGTCTGCTCCC
GGCATCCGCTTACAGACAAGCTGTGACCGTCTCCGGGAGAGCTCGATATC
CCGGGCGGCCGCTTCATTTATAAATTTCTTGACATTTTGGAATAGATGTG
ATATAATGTGTACATATCCATGGCGGCCGCTCTAGAAGAAGCTTGGGATC
CGTCGACCTCG
```

The flux redirections and mutations for GDP-fucose and fucosyllated oligosaccharide biosynthesis in a split metabolism are shown in FIG. 8, both for a strain expressing a heterologous invertase and sucrose phosphorylase. Additional to wcaJ, the colanic acid operon genes that do not code for GDP-fucose biosynthesis reactions are knocked out, such as gmm, wcaA, wcaB, wcaC, wcaD, wcaE, wcaF, wcal, wcaK, wcaL and/or, wcaM. For the production of fucosyllactose, lacZ, coding for β-galactosidase, is knocked out to avoid lactose degradation and the expression of lacY, coding for a lactose permease, is enhanced by means of a strong constitutive promoter.

Example 5: Enhancement of GDP-Fucose and Fucosylated Oligosaccharide Production Via a Split Metabolism with Glucose as Substrate When the genes pgi, pfkA, and pfkB are knocked out, carbon, taken up as glucose can only be metabolised via the pentose phosphate pathway. Due to the biochemical properties of this pathway, fructose-6-phosphate is formed (FIGS. 9 and 10). To form biomass glyceraldehyde-3-phosphate has to be formed, which is formed by the transketolase reactions coded by tktA and tktB in *E. coli*. This Glyceraldehyde-3-phosphate is formed together with fructose-6-phosphate from xylulose-5-phosphate and erythrose-5-phosphate. The latter is in turn formed together with fructose-6-phosphate from glyceraldehyde-3-phosphate and sedoheptulose-7-phosphate via transaldolase reactions coded by talA and talB. To balance all of these reactions together the flux has to be distributed between xylulose-5-phosphate and ribose-5-phosphate, as such that from 1 mole glucose, ⅔ mole of xylulose-5-phosphate and ⅓ mole ribose-5-phosphate is formed. To drive these equilibrium reactions, fructose-6-phosphate is pulled out of the pentose phosphate pathway by the GDP-fucose and fucosyllacted oligosaccharide biosynthesis pathway. Additional to wcaJ, the colanic acid operon genes that do not code for GDP-fucose biosynthesis reactions are knocked out, such as gmm, wcaA, wcaB, wcaC, wcaD, wcaE, wcaF, wcal, wcaK, wcaL and/or, wcaM. For the production of fucosyllactose, lacZ coding for β-galactosidase, is knocked out to avoid lactose degradation and the expression of lacY, coding for a lactose permease, is enhanced by means of a strong constitutive promoter.

Example 6: Fermentative 2-Fucosyllactose Production with a Fucosyltransferase Originating from *Helicobacter pylori*

The mutant strain in which the genes lacZ, glgC, agp, pfkA, pfkB, pgi, arcA, iclR, wcaJ are knocked out and lacY was expressed via constitutive expression to ensure expression under all culturing conditions, was transformed further with a fucosyltransferase originating from *Helicobacter pylori* and a sucrose phosphorylase originating from *Bifidobacterium adolescentis*, which were also constitutively expressed. The constitutive promoters originate from the promoter library described by De Mey et al. 2007. This strain was cultured in a medium as described in the materials and methods, however with 30 g/l of sucrose and 50 g/l of lactose. This resulted in the formation of 2-fucosyllactose as shown in FIGS. 13 and 14.

Example 7: Fermentative Fucosyllactose Production with a Fucosyltransferase Originating from *Dictyostellium discoideum*

The mutant strain in which the genes lacZ, glgC, agp, pfkA, pfkB, pgi, arcA, iclR, wcaJ are knocked out and lacY was expressed via constitutive expression to ensure expression under all culturing conditions, was transformed further with a fucosyltransferase originating from *Dictyostellium discoideum* and a sucrose phosphorylase originating from *Bifidobacterium adolescentis*, which were also expressed constitutively. The constitutive promoters originate from the promoter library described by De Mey et al. 2007. This strain was cultured in a medium as described in the materials and methods, however with 30 g/l of sucrose and 50 g/l of lactose. This resulted in the formation of 2-fucosyllactose as shown in FIGS. 13 and 14.

Example 8: Enhancement of GDP-Mannose and Mannosylated Oligosaccharide Production Via a Split Metabolism with Sucrose as Substrate To accumulate the GDP-mannose precursors fructose and fructose-6-phosphate, a sucrose phosphorylase or invertase is introduced. Because fructose-6-phosphate is easily degraded in the glycolysis, the glycolysis is interrupted in order to steer all fructose-6-phosphate in the direction of GDP-fucose. The genes pgi, pfkA and pfkB are thus knocked out, coding for glucose-6-phosphate isomerase and phosphofructokinase A and B. Finally a mannosyltransferase is introduced to link mannose to an acceptor molecule. To avoid GDP-mannose degradation the genes gmm and gmd have to be knocked out in the colanic acid operon. In addition, the genes that do not code for GDP-mannose biosynthesis reactions are knocked out, such as wcaA, wcaB, wcaC, wcaD, wcaE, wcaF, wcal, wcaJ, wcaK, wcaL and/or, wcaM.

Example 9: Upregulation of Acid Resistance Related Genes

Similar to the colanic acid operon upregulation, acid resistance related genes are also upregulated in a ΔarcAΔiclR double mutant strain in comparison to the wild type strain and the single mutant strains. These genes make a strain more resistant to low pH, which is beneficial for the production of acids (4) or the production of glucosamine (12) which is not stable at neutral and high pH. FIG. 12 presents the gene expression pattern of these acid resistance related genes and indicates up to 8 fold expression increase in the double mutant strain.

Example 10: Fed Batch Production of 2-Fucosyllactose

A mutant strain was constructed via the genetic engineering methodologies described above with the following genotype:

ΔlacZYA::P22-lacYΔglgCΔagpApgiΔpfkΔ-P22-baSPΔpfkBΔarcAΔiclR::slΔwcaJΔlonΔadhE-P14-frk+ pCXP14-FT_*H. pylori* (a vector with sequence SEQ ID No 1). The promoter P22 and P14 originate from the promoter library constructed by De Mey et al (11) and was cloned similar to the methodology described by Aerts et al (2). "::sl" marks a scarless gene deletion, thus without a FRT site that remains in the chromosome.

This strain was cultured in a bioreactor as described above in materials and methods, in the mineral medium with 30 g/l of sucrose and 50 g/l of lactose. After the batch phase the bioreactor was fed with 500 g/l of sucrose, 50 g/l lactose and 1 g/l of magnesium sulphate heptahydrate. This led to the accumulation of 27.5 g/l of fucosyllactose in the supernatant.

SEQID No 1: pCXP14-FT_*H. pylori*

```
CGCGTTGGATGCAGGCATGCAAGCTTGGCTGTTTTGGCGGATGAGAGAAG
ATTTTCAGCCTGATACAGATTAAATCAGAACGCAGAAGCGGTCTGATAAA
ACAGAATTTGCCTGGCGGCAGTAGCGCGGTGGTCCCACCTGACCCCATGC
CGAACTCAGAAGTGAAACGCCGTAGCGCCGATGGTAGTGTGGGGTCTCCC
CATGCGAGAGTAGGGAACTGCCAGGCATCAAATAAAACGAAAGGCTCAGT
CGAAAGACTGGGCCTTTCGTTTTATCTGTTGTTTGTCGGTGAACGCTCTC
CTGAGTAGGACAAATCCGCCGGGAGCGGATTTGAACGTTGCGAAGCAACG
GCCCGGAGGGTGGCGGGCAGGACGCCCGCCATAAACTGCCAGGCATCAAA
TTAAGCAGAAGGCCATCCTGACGGATGGCCTTTTTGCGTTTCTACAAACT
CTTTTTGTTTATTTTTCTAAATACATTCAAATATGTATCCGCTCATGAGA
CAATAACCCTGATAAATGCTTCAATAATATTGAAAAAGGAAGAGTATGAG
TATTCAACATTTCCGTGTCGCCCTTATTCCCTTTTTTGCGGCATTTTGCC
TTCCTGTTTTTGCTCACCCAGAAACGCTGGTGAAAGTAAAAGATGCTGAA
GATCAGTTGGGTGCACGAGTGGGTTACATCGAACTGGATCTCAACAGCGG
TAAGATCCTTGAGAGTTTTCGCCCCGAAGAACGTTTTCCAATGATGAGCA
CTTTTAAAGTTCTGCTATGTGGCGCGGTATTATCCCGTGTTGACGCCGGG
CAAGAGCAACTCGGTCGCCGCATACACTATTCTCAGAATGACTTGGTTGA
GTACTCACCAGTCACAGAAAAGCATCTTACGGATGGCATGACAGTAAGAG
AATTATGCAGTGCTGCCATAACCATGAGTGATAACACTGCGGCCAACTTA
CTTCTGACAACGATCGGAGGACCGAAGGAGCTAACCGCTTTTTTGCACAA
CATGGGGGATCATGTAACTCGCCTTGATCGTTGGGAACCGGAGCTGAATG
AAGCCATACCAAACGACGAGCGTGACACCACGATGCCTACAGCAATGGCA
ACAACGTTGCGCAAACTATTAACTGGCGAACTACTTACTCTAGCTTCCCG
GCAACAATTAATAGACTGGATGGAGGCGGATAAAGTTGCAGGACCACTTC
TGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAA
GCCCTCCCGTATCGTAGTTATCTACACGACGGGGAGTCAGGCAACTATGG
ATGAACGAAATAGACAGATCGCTGAGATAGGTGCCTCACTGATTAAGCAT
TGGTAACTGTCAGACCAAGTTTACTCATATATACTTTAGATTGATTTAAA
ACTTCATTTTTAATTTAAAAGGATCTAGGTGAAGATCCTTTTTGATAATC
TCATGACCAAAATCCCTTAACGTGAGTTTTCGTTCCACTGAGCGTCAGAC
CCCGTAGAAAAGATCAAAGGATCTTCTTGAGATCCTTTTTTTCTGCGCGT
AATCTGCTGCTTGCAAACAAAAAAACCACCGCTACCAGCGGTGGTTTGTT
TGCCGGATCAAGAGCTACCAACTCTTTTTCCGAAGGTAACTGGCTTCAGC
AGAGCGCAGATACCAAATACTGTCCTTCTAGTGTAGCCGTAGTTAGGCCA
CCACTTCAAGAACTCTGTAGCACCGCCTACATACCTCGCTCTGCTAATCC
TGTTACCAGTGGCTGCTGCCAGTGGCGATAAGTCGTGTCTTACCGGGTTG
GACTCAAGACGATAGTTACCGGATAAGGCGCAGCGGTCGGGCTGAACGGG
GGGTTCGTGCACACAGCCCAGCTTGGAGCGAACGACCTACACCGAACTGA
```

-continued

```
GATACCTACAGCGTGAGCTATGAGAAAGCGCCACGCTTCCCGAAGGGAGA

AAGGCGGACAGGTATCCGGTAAGCGGCAGGGTCGGAACAGGAGAGCGCAC

GAGGGAGCTTCCAGGGGGAAACGCCTGGTATCTTTATAGTCCTGTCGGGT

TTCGCCACCTCTGACTTGAGCGTCGATTTTTGTGATGCTCGTCAGGGGGG

CGGAGCCTATGGAAAAACGCCAGCAACGCGGCCTTTTTACGGTTCCTGGC

CTTTTGCTGGCCTTTTGCTCACATGTTCTTTCCTGCGTTATCCCCTGATT

CTGTGGATAACCGTATTACCGCCTTTGAGGAGCTGATACCGCTCGCCGCA

GCCGAACGACCGAGCGCAGCGAGTCAGTGAGCGAGGAAGCGGAAGAGCGC

CTGATGCGGTATTTTCTCCTTACGCATCTGTGCGGTATTTCACACCGCAT

ATGGTGCACTCTCAGTACAATCTGCTCTGATGCCGCATAGTTAAGCCAGT

ATACACTCCGCTATCGCTACGTGACTGGGTCATGGCTGCGCCCCGACACC

CGCCAACACCCGCTGACGCGCCCTGACGGGCTTGTCTGCTCCCGGCATCC

GCTTACAGACAAGCTGTGACCGTCTCCGGGAGAGCTCGATATCCCGGGCG

GCCGCCTTCATTCTATAAGTTTCTTGACATCTTGGCCGGCATATGGTATA

ATAGGGAAATTTCCATGGCGGCCGCTCTAGAAGAAGCTTGGGATCCGTCG

ACCTCGAATTCGGAGGAAACAAAGATGGCCTTTAAAGTTGTTCAGATTTG

TGGTGGTCTGGGCAATCAGATGTTTCAGTATGCATTTGCAAAAAGCCTGC

AGAAACATAGCAATACACCGGTTCTGCTGGATATTACCAGCTTTGATTGG

AGCAATCGTAAAATGCAGCTGGAACTGTTTCCGATTGATCTGCCGTATGC

AAGCGAAAAAGAAATTGCAATTGCCAAAATGCAGCATCTGCCGAAACTGG

TTCGTAATGTTCTGAAATGCATGGGTTTTGATCGTGTGAGCCAAGAAATC

GTGTTTGAATATGAACCGAAACTGCTGAAAACCAGCCGTCTGACCTATTT

TTATGGCTATTTTCAGGATCCGCGTTATTTTGATGCAATTAGTCCGCTGA

TCAAACAGACCTTTACCCTGCCTCCGCCTCCGGAAAATGGTAATAACAAA

AAAAAAGAAGAAGAGTATCATCGTAAACTGGCACTGATTCTGGCAGCAAA

AAATAGCGTGTTTGTGCATATTCGTCGCGGTGATTATGTTGGTATTGGTT

GTCAGCTGGGCATCGATTATCAGAAAAAAGCACTGGAATACATGGCAAAA

CGTGTTCCGAATATGGAACTGTTTGTGTTTTGCGAGGACCTGGAATTTAC

CCAGAATCTGGATCTGGGCTATCCGTTTATGGATATGACCACCCGTGATA

AAGAGGAAGAGGCATATTGGGATATGCTGCTGATGCAGAGCTGTAAACAT

GGTATTATTGCCAACAGCACCTATAGTTGGTGGGCAGCATATCTGATTAA

TAACCCGGAAAAAATCATTATTGGTCCGAAACATTGGCTGTTTGGCCATG

AAAACATCCTGTGTAAAGAATGGGTGAAAATCGAAAGCCACTTTGAAGTG

AAAAGCCAGAAATATAATGCCTAATAAGAGCTCCCAA
```

Example 11: Fed Batch Production of 2-Fucosyllactose with a Hybrid Colanic Acid Promoter A hybrid colanic acid promoter was constructed based on the genome information and the sequences from the promoter library described by De Mey et al (11).

ΔlacZYA::P22-lacYΔglgCΔagpApgiΔpfkA::P22-BaSPΔpfkB ΔarcAΔiclR:sl ΔwcaJ Δlon ΔadhE-P14-frk ΔldhA::P14-FT_*H. pylori* ΔpromCA:P14

This strain was cultured in a bioreactor as described above in materials and methods, in the mineral medium with 30 g/l of sucrose and 20 g/l of lactose. After the batch phase the bioreactor was fed with 500 g/l of sucrose, 20 g/l lactose and 1 g/l of magnesium sulphate heptahydrate. This led to the accumulation of 26 g/l of fucosyllactose in the supernatant with nearly stoichiometric conversion of lactose. Increasing the lactose feed concentrations leads further to increased final fucosyllactose titers and stoichiometric lactose conversion.

REFERENCES 1. 2006. R: A Language and Environment for Statistical Computing. R Foundation for Statistical Computing. R-Development Core Team, Vienna, Austria.
2. Aerts, D., T. Verhaeghe, M. De Mey, T. Desmet, and W. Soetaert. 2010. A constitutive expression system for high throughput screening. Engineering in Life Sciences 10:DOI: 10.1002/elsc.201000065.
3. Alper, H., C. Fischer, E. Nevoigt, and G. Stephanopoulos. 2005. Tuning genetic control through promoter engineering. Proceedings of the national academy of sciences of the United States of America 102:12678-12683.
4. Beauprez, J. 2010. Metabolic modelling and engineering of *Escherichia coli* for succinate production. PhD. Ghent University, Ghent.
5. Bode, L. 2006. Recent Advances on Structure, Metabolism, and Function of Human Milk Oligosaccharides. The Journal of Nutrition 136:2127-2130.
6. Canton, B., A. Labno, and D. Endy. 2008. Refinement and standardization of synthetic biological parts and devices. Nat Biotech 26:787-793.
7. Cavallaro, G., L. Maniscalco, P. Caliceti, S. Salmaso, A. Semenzato, and G. Giammona. 2004. Glycosilated Macromolecular Conjugates of Antiviral Drugs with a Polyaspartamide. Journal of Drug Targeting 12:593-605.
8. Coppa, G. V., L. Zampini, T. Galeazzi, and O. Gabrielli. 2006. Prebiotics in human milk: a review. Digestive and Liver Disease 38:S291-S294.
9. Datsenko, K. A., and B. L. Wanner. 2000. One-step inactivation of chromosomal genes in *Escherichia coli* K-12 using PCR products. Proceedings of the national academy of sciences of the United States of America 97:6640-6645.
10. De Mey, M., G. J. Lequeux, J. J. Beauprez, J. Maertens, E. Van Horen, W. K. Soetaert, P. A. Vanrolleghem, and E. J. Vandamme. 2007. Comparison of different strategies to reduce acetate formation in *Escherichia coli*. Biotechnology Progress.
11. De Mey, M., J. Maertens, G. J. Lequeux, W. K. Soetaert, and E. J. Vandamme. 2007. Construction and model-based analysis of a promoter library for *E. coli*: an indispensable tool for metabolic engineering. BMC Biotechnology 7:34-48.
12. Deng, M.-D., D. K. Severson, A. D. Grund, S. L. Wassink, R. P. Burlingame, A. Berry, J. A. Running, C. A. Kunesh, L. Song, T. A. Jerrell, and R. A. Rosson. 2005. Metabolic engineering of *Escherichia coli* for industrial production of glucosamine and N-acetylglucosamine. Metabolic Engineering 7:201-214.
13. Ebel, W., and J. E. Trempy. 1999. *Escherichia coli* RcsA, a Positive Activator of Colanic Acid Capsular Polysaccharide Synthesis, Functions To Activate Its Own Expression. Journal of bacteriology 181:577-584.

14. Foster, J. W. 2004. *Escherichia coli* acid resistance: Tales of an amateur acidophile. Nature Reviews Microbiology 2:898-907.
15. Hammer, K., I. Mijakovic, and P. R. Jensen. 2006. Synthetic promoter libraries—tuning of gene expression. TRENDS in Biotechnology 24:53-55.
16. Hanahan, D., J. Jessee, and F. R. Bloom. 1991. Plasmid transformation of *Escherichia coli* and other bacteria. Methods in Enzymology 204:63-113.
17. Hommais, F., E. Krin, J.-Y. Coppee, C. Lacroix, E. Yeramian, A. Danchin, and P. Bertin. 2004. GadE (YhiE): a novel activator involved in the response to acid environment in *Escherichia coli*. Microbiology 150:61-72.
18. Jigami, Y. 2008. Yeast Glycobiology and Its Application. Bioscience, Biotechnology, and Biochemistry 72:637-648.
19. Keasling, J. D. 1999. Gene-expression tools for the metabolic engineering of bacteria. Trends in Biotechnology 17:452-460.
20. Lequeux, G. 2008. Metabolic modelling and analysis for the optimization of *Escherichia coli* as a production host. Ghent University, Ghent.
21. Lequeux, G., L. Johansson, J. Maertens, P. Vanrolleghem, and G. Liden. 2005. Metabolic flux analysis of C- and P-limited shikimic acid producing *E. coli*. Journal of Biotechnology 118:S121-S121.
22. Masuda, N., and G. M. Church. 2003. Regulatory network of acid resistance genes in *Escherichia coli*. Molecular Microbiology 48:699-712.
23. Pattyn, F., F. Speleman, A. De Paepe, and J. Vandesompele. 2003. RTPrimerDB: The Real-Time PCR primer and probe database. Nucleic Acids Research 31:122-123.
24. Perrenoud, A., and U. Sauer. 2005. Impact of global transcriptional regulation by ArcA, ArcB, Cra, Crp, Cya, Fnr, and MIc on glucose catabolism in *Escherichia coli*. *Journal of Bacteriology* 187:3171-3179.
25. Ritz, C., and A.-N. Spiess. 2008. qpcR: an R package for sigmoidal model selection in quantitative real-time polymerase chain reaction analysis. Bioinformatics 24:1549-1551.
26. Salis, H. M., E. A. Mirsky, and C. A. Voigt. 2009. Automated design of synthetic ribosome binding sites to control protein expression. Nat Biotech 27:946-950.
27. Seed, B., and J. Holgersson. 1999. Fucosyltransferase genes and uses thereof U.S. Pat. No. 5,858,752.
28. Shalel-Levanon, S., K. Y. San, and G. N. Bennett. 2005. Effect of ArcA and FNR on the expression of genes related to the oxygen regulation and glycolysis pathway in *Escherichia coli* under growth conditions. Biotechnology and Bioengineering 92:147-159.
29. Shalel-Levanon, S., K. Y. San, and G. N. Bennett. 2005. Effect of oxygen on the *Escherichia coli* ArcA and FNR regulation systems and metabolic responses. Biotechnology and Bioengineering 89:556-564.
30. Smith, S., A. D. Elbein, and Y. T. Pan. 1999. Inhibition of Pathogenic Bacterial Binding by High Mannose Oligosaccharides U.S. Pat. No. 5,939,279.
31. Smyth, G. K. 2005. limma: Linear models for microarray data., p. 397-420. In R. Gentleman, V. Carey, W. Huber, R. A. Irizarry, and S. Dudoit (ed.), Bioinformatics and Computational Biology Solutions Using R and Bioconductor. Springer.
32. Smyth, G. K. 2004. Linear Models and Empirical Bayes Methods for Assessing Differential Expression in Microarray Experiments. Statistical Applications in Genetics and Molecular Biology 3:3.
33. Smyth, G. K., and T. Speed. 2003. Normalization of cDNA microarray data.
Methods 31:265-273.
34. Spiess, A.-N., C. Feig, and C. Ritz. 2008. Highly accurate sigmoidal fitting of real-time PCR data by introducing a parameter for asymmetry. BMC Bioinformatics 9:221.
35. Stevenson, G., K. Andrianopoulos, M. Hobbs, and P. R. Reeves. 1996. Organization of the *Escherichia coli* K-12 gene cluster responsible for production of the extracellular polysaccharide colanic acid. Journal of Bacteriology 178:4885-4893.
36. Stout, V., A. Torres-Cabassa, M. R. Maurizi, D. Gutnick, and S. Gottesman. 1991. RcsA, an unstable positive regulator of capsular polysaccharide synthesis. Journal of bacteriology 173:1738-1747.
37. Sunnarborg, A., D. Klumpp, T. Chung, and D. C. Laporte. 1990. Regulation of the glyoxylate bypass operon: cloning and characterization of IclR. Journal of Bacteriology 172:2642-2649.
38. Waegeman, H. J., J. Beauprez, H. Moens, J. Maertens, M. De Mey, M. R. Foulquie-Moreno, J. J. Heijnen, D. Charlier, and W. Soetaert. 2010. Effect of iclR and arcA knockouts on biomass formation and metabolic fluxes in *Escherichia coli* K12 and its implications on understanding the metabolism of *Escherichia coli* BL21 (DE3). BMC microbiology 11:1-17.
39. Waegeman, H. J., J. Beauprez, H. Moens, J. Maertens, M. De Mey, M. R. Foulquie-Moreno, J. J. Heijnen, D. Charlier, and W. Soetaert. 2011. Effect of iclR and arcA knockouts on biomass formation and metabolic fluxes in *Escherichia coli* K12 and its implications on understanding the metabolism of *Escherichia coli* BL21 (DE3). BMC microbiology 11:1-17.
40. Warnecke, T., and R. T. Gill. 2005. Organic acid toxicity, tolerance, and production in *Escherichia coli* biorefining applications. Microbial Cell Factories 4.

The invention claimed is:

1. A method for synthesizing sialylated oligosaccharides, acetylated oligosaccharides, sulfonated oligosaccharides, glucosamine, or acids, comprising growing a genetically modified microorganism on fermentation medium with acidic pH, wherein transcriptional regulators aerobic respiration control protein ArcA and isocitrate lyase regulator IclR have been genetically modified in said micro-organism, thereby upregulating at least one of the following acid resistance related genes: ydeP, ydeO, hdeA, hdeD, gadB, gadC, gadE, gadX, gadW and/or slp as compared to the expression of said genes within a corresponding wild type microorganism, and wherein at least one mutation that enhances the production of sialylated oligosaccharides, acetylated oligosaccharides, sulfonated oligosaccharides, glucosamine, or acids has been introduced in said micro-organism.

2. The method according to claim 1, wherein said micro-organism synthesizes sialylated oligosaccharides, acetylated oligosaccharides or sulfonated oligosaccharides.

3. The method according to claim 1, wherein said micro-organism synthesizes glucosamine.

4. The method according to claim 1, wherein said micro-organism is growing in a non-buffered fermentation medium.

5. The method according to claim 1, wherein said micro-organism synthesizes acid chosen from the list comprising pyruvic acid, succinic acid, adipic acid, and sialic acid.

6. The method according to claim 1, wherein said sialylated oligosaccharide is chosen from the list comprising sialyllactose and sialyl Lewis X sugars.

7. The method according to claim 1, wherein said acetylated oligosaccharide is chosen from the list comprising chitins and chitosans.

8. The method according to claim 1, wherein said sulfonated oligosaccharide is chosen from the list comprising heparans and heparosans.

9. The method according to claim 1, wherein said micro-organism has increased resistance to acidic pH as compared to a corresponding wild type microorganism.

10. A mutated and/or transformed microorganism wherein at least one of the following acid resistance related genes: ydeP, ydeO, hdeA, hdeD, gadB, gadC, gadE, gadX, gadW and/or slp are upregulated by genetically modified transcriptional regulators aerobic respiration control protein ArcA and isocitrate lyase regulator IclR, and wherein at least one mutation that enhances the production of sialylated oligosaccharides, acetylated oligosaccharides, sulfonated oligosaccharides, glucosamine, or acids has been introduced.

11. The microorganism according to claim 10, wherein said genetic modification comprises a genetic change leading to a decreased or an abolished expression of the genes encoding the transcriptional regulators aerobic respiration control protein ArcA and isocitrate lyase regulator IclR.

12. The microorganism according to claim 10, wherein said genetic modification comprises disrupted genes encoding ArcA and IclR, replaced endogenous promoters of genes encoding for ArcA and IclR by artificial promoters, or replaced endogenous ribosome binding site by an artificial ribosome binding site.

13. The microorganism according to claim 10, wherein said microorganism is a bacterium belonging to the family of Enterobacteriaceae.

14. The method according to claim 1, wherein said microorganism is an *Escherichia coli* strain.

15. The microorganism according to claim 10, wherein said microorganism is an *Escherichia coli* strain.

16. The microorganism according to claim 15, wherein said *E. coli* strain is a K12 strain.

17. The method according to claim 14, wherein said *E. coli* strain is a K12 strain.

18. The method according to claim 1, wherein said genetic modification comprises making a genetic change leading to a decreased or an abolished expression of the genes encoding the transcriptional regulators aerobic respiration control protein ArcA and isocitrate lyase regulator IclR.

19. The method according to claim 1, wherein said genetic modification comprises disrupting genes encoding ArcA and IclR, replacing endogenous promoters of genes encoding for ArcA and IclR by artificial promoters, or replacing endogenous ribosome binding site by an artificial ribosome binding site.

20. The method according to claim 1, wherein said microorganism is a bacterium belonging to the family of Enterobacteriaceae.

21. A method for synthesizing sialylated oligosaccharides, acetylated oligosaccharides, sulfonated oligosaccharides, glucosamine, or acids, comprising: genetically modifying transcriptional regulators aerobic respiration control protein ArcA and isocitrate lyase regulator IclR in a microorganism to upregulate at least one of the following acid resistance related genes: ydeP, ydeO, hdeA, hdeD, gadB, gadC, gadE, gadX, gadW and/or slp as compared to the expression of said genes within a corresponding wild type microorganism; and growing the genetically modified microorganism on fermentation medium with acidic pH to produce sialylated oligosaccharides, acetylated oligosaccharides, sulfonated oligosaccharides, glucosamine, or acids.

* * * * *

SEQUENCE LISTING

```
<160> NUMBER OF SEQ ID NOS: 90

<210> SEQ ID NO 1
<211> LENGTH: 3638
<212> TYPE: DNA
<213> ORGANISM: Artificial sequence
<220> FEATURE:
<223> OTHER INFORMATION: Vector

<400> SEQUENCE: 1

cgcgttggat gcaggcatgc aagcttggct gttttggcgg atgagagaag attttcagcc      60
```

-continued

```
tgatacagat taaatcagaa cgcagaagcg gtctgataaa acagaatttg cctggcggca    120
gtagcgcggt ggtcccacct gaccccatgc cgaactcaga agtgaaacgc cgtagcgccg    180
atggtagtgt ggggtctccc catgcgagag tagggaactg ccaggcatca aataaaacga    240
aaggctcagt cgaaagactg ggcctttcgt tttatctgtt gtttgtcggt gaacgctctc    300
ctgagtagga caaatccgcc gggagcggat ttgaacgttg cgaagcaacg gcccggaggg    360
tggcgggcag gacgcccgcc ataaactgcc aggcatcaaa ttaagcagaa ggccatcctg    420
acggatggcc tttttgcgtt tctacaaact ctttttgttt atttttctaa atacattcaa    480
atatgtatcc gctcatgaga caataaccct gataaatgct tcaataatat tgaaaaagga    540
agagtatgag tattcaacat ttccgtgtcg cccttattcc cttttttgcg gcattttgcc    600
ttcctgtttt tgctcaccca gaaacgctgg tgaaagtaaa agatgctgaa gatcagttgg    660
gtgcacgagt gggttacatc gaactggatc tcaacagcgg taagatcctt gagagttttc    720
gccccgaaga acgttttcca atgatgagca cttttaaagt tctgctatgt ggcgcggtat    780
tatcccgtgt tgacgccggg caagagcaac tcggtcgccg catacactat tctcagaatg    840
acttggttga gtactcacca gtcacagaaa agcatcttac ggatggcatg acagtaagag    900
aattatgcag tgctgccata accatgagtg ataacactgc ggccaactta cttctgacaa    960
cgatcggagg accgaaggag ctaaccgctt ttttgcacaa catgggggat catgtaactc   1020
gccttgatcg ttgggaaccg gagctgaatg aagccatacc aaacgacgag cgtgacacca   1080
cgatgcctac agcaatggca acaacgttgc gcaaactatt aactggcgaa ctacttactc   1140
tagcttcccg gcaacaatta atagactgga tggaggcgga taaagttgca ggaccacttc   1200
tgcgctcggc ccttccggct ggctggttta ttgctgataa atctggagcc ggtgagcgtg   1260
ggtctcgcgg tatcattgca gcactggggc cagatggtaa gccctcccgt atcgtagtta   1320
tctacacgac ggggagtcag gcaactatgg atgaacgaaa tagacagatc gctgagatag   1380
gtgcctcact gattaagcat tggtaactgt cagaccaagt ttactcatat atactttaga   1440
ttgatttaaa acttcatttt taatttaaaa ggatctaggt gaagatcctt tttgataatc   1500
tcatgaccaa aatcccttaa cgtgagtttt cgttccactg agcgtcagac cccgtagaaa   1560
agatcaaagg atcttcttga gatccttttt ttctgcgcgt aatctgctgc ttgcaaacaa   1620
aaaaaccacc gctaccagcg gtggtttgtt tgccggatca agagctacca actctttttc   1680
cgaaggtaac tggcttcagc agagcgcaga taccaaatac tgtccttcta gtgtagccgt   1740
agttaggcca ccacttcaag aactctgtag caccgcctac atacctcgct ctgctaatcc   1800
tgttaccagt ggctgctgcc agtggcgata agtcgtgtct taccgggttg gactcaagac   1860
gatagttacc ggataaggcg cagcggtcgg gctgaacggg gggttcgtgc acacagccca   1920
gcttggagcg aacgacctac accgaactga gatacctaca gcgtgagcta tgagaaagcg   1980
ccacgcttcc cgaagggaga aaggcggaca ggtatccggt aagcggcagg gtcggaacag   2040
gagagcgcac gagggagctt ccagggggaa acgcctggta tctttatagt cctgtcgggt   2100
ttcgccacct ctgacttgag cgtcgatttt tgtgatgctc gtcagggggg cggagcctat   2160
ggaaaaacgc cagcaacgcg gcctttttac ggttcctggc cttttgctgg ccttttgctc   2220
acatgttctt tcctgcgtta tcccctgatt ctgtggataa ccgtattacc gcctttgagt   2280
gagctgatac cgctcgccgc agccgaacga ccgagcgcag cgagtcagtg agcgaggaag   2340
cggaagagcg cctgatgcgg tattttctcc ttacgcatct gtgcggtatt tcacaccgca   2400
tatggtgcac tctcagtaca atctgctctg atgccgcata gttaagccag tatacactcc   2460
```

gctatcgcta cgtgactggg tcatggctgc gccccgacac ccgccaacac ccgctgacgc 2520
gccctgacgg gcttgtctgc tcccggcatc cgcttacaga caagctgtga ccgtctccgg 2580
gagagctcga tatcccgggc ggccgccttc attctataag tttcttgaca tcttggccgg 2640
catatggtat aatagggaaa tttccatggc ggccgctcta gaagaagctt gggatccgtc 2700
gacctcgaat tcggaggaaa caaagatggc ctttaaagtt gttcagattt gtggtggtct 2760
gggcaatcag atgtttcagt atgcatttgc aaaaagcctg cagaaacata gcaatacacc 2820
ggttctgctg gatattacca gctttgattg gagcaatcgt aaaatgcagc tggaactgtt 2880
tccgattgat ctgccgtatg caagcgaaaa agaaattgca attgccaaaa tgcagcatct 2940
gccgaaactg gttcgtaatg ttctgaaatg catgggtttt gatcgtgtga gccaagaaat 3000
cgtgtttgaa tatgaaccga aactgctgaa aaccagccgt ctgacctatt tttatggcta 3060
ttttcaggat ccgcgttatt ttgatgcaat tagtccgctg atcaaacaga cctttaccct 3120
gcctccgcct ccggaaaatg gtaataacaa aaaaaaagaa gaagagtatc atcgtaaact 3180
ggcactgatt ctggcagcaa aaaatagcgt gtttgtgcat attcgtcgcg gtgattatgt 3240
tggtattggt tgtcagctgg gcatcgatta tcagaaaaaa gcactggaat acatggcaaa 3300
acgtgttccg aatatggaac tgtttgtgtt ttgcgaggac ctggaattta cccagaatct 3360
ggatctgggc tatccgttta tggatatgac cacccgtgat aaagaggaag aggcatattg 3420
ggatatgctg ctgatgcaga gctgtaaaca tggtattatt gccaacagca cctatagttg 3480
gtgggcagca tatctgatta ataacccgga aaaaatcatt attggtccga aacattggct 3540
gtttggccat gaaaacatcc tgtgtaaaga atgggtgaaa atcgaaagcc actttgaagt 3600
gaaaagccag aaatataatg cctaataaga gctcccaa 3638

<210> SEQ ID NO 2
<211> LENGTH: 4311
<212> TYPE: DNA
<213> ORGANISM: Artificial sequence
<220> FEATURE:
<223> OTHER INFORMATION: Plasmid

<400> SEQUENCE: 2
aattcggagg aaacaaagat ggggggttct catcatcatc atcatcatgg tatggctagc 60
atgaaaaaca aggtgcagct catcacttac gccgaccgcc ttggcgacgg caccatcaag 120
tcgatgaccg acattctgcg cacccgcttc gacggcgtgt acgacggcgt tcacatcctg 180
ccgttcttca ccccgttcga cggcgccgac gcaggcttcg acccgatcga ccacaccaag 240
gtcgacgaac gtctcggcag ctgggacgac gtcgccgaac tctccaagac ccacaacatc 300
atggtcgacg ccatcgtcaa ccacatgagt tgggaatcca agcagttcca ggacgtgctg 360
gccaagggcg aggagtccga atactatccg atgttcctca ccatgagctc cgtgttcccg 420
aacggcgcca ccgaagagga cctggccggc atctaccgtc cgcgtccggg cctgccgttc 480
acccactaca agttcgccgg caagacccgc ctcgtgtggg tcagcttcac cccgcagcag 540
gtggacatcg acaccgattc cgacaagggt tgggaatacc tcatgtcgat tttcgaccag 600
atggccgcct ctcacgtcag ctacatccgc ctcgacgccg tcggctatgg cgccaaggaa 660
gccggcacca gctgcttcat gaccccgaag accttcaagc tgatctcccg tctgcgtgag 720
gaaggcgtca agcgcggtct ggaaatcctc atcgaagtgc actcctacta caagaagcag 780
gtcgaaatcg catccaaggt ggaccgcgtc tacgacttcg ccctgcctcc gctgctgctg 840

-continued

```
cacgcgctga gcaccggcca cgtcgagccc gtcgcccact ggaccgacat acgccgaac     900
aacgccgtca ccgtgctcga tacgcacgac ggcatcggcg tgatcgacat cggctccgac    960
cagctcgacc gctcgctcaa gggtctcgtg ccggatgagg acgtggacaa cctcgtcaac   1020
accatccacg ccaacaccca cggcgaatcc caggcagcca ctggcgccgc cgcatccaat   1080
ctcgacctct accaggtcaa cagcacctac tattcggcgc tcgggtgcaa cgaccagcac   1140
tacatcgccg cccgcgcggt gcagttcttc ctgccgggcg tgccgcaagt ctactacgtc   1200
ggcgcgctcg ccggcaagaa cgacatggag ctgctgcgta agacgaataa cggccgcgac   1260
atcaatcgcc attactactc caccgcggaa atcgacgaga acctcaagcg tccggtcgtc   1320
aaggccctga acgcgctcgc caagttccgc aacgagctcg acgcgttcga cggcacgttc   1380
tcgtacacca ccgatgacga cacgtccatc agcttcacct ggcgcggcga aaccagccag   1440
gccacgctga cgttcgagcc gaagcgcggt ctcggtgtgg acaacgctac gccggtcgcc   1500
atgttggaat gggaggattc cgcgggagac caccgttcgg atgatctgat cgccaatccg   1560
cctgtcgtcg cctgactgca ggtcgaccat atgggagagc tcccaacgcg ttggatgcag   1620
gcatgcaagc ttggctgttt tggcggatga gagaagattt tcagcctgat acagattaaa   1680
tcagaacgca gaagcggtct gataaaacag aatttgcctg gcggcagtag cgcggtggtc   1740
ccacctgacc ccatgccgaa ctcagaagtg aaacgccgta gcgccgatgg tagtgtgggg   1800
tctccccatg cgagagtagg gaactgccag gcatcaaata aaacgaaagg ctcagtcgaa   1860
agactgggcc tttcgtttta tctgttgttt gtcggtgaac gctctcctga gtaggacaaa   1920
tccgccggga gcggatttga acgttgcgaa gcaacggccc ggagggtggc gggcaggacg   1980
cccgccataa actgccaggc atcaaattaa gcagaaggcc atcctgacgg atggcctttt   2040
tgcgtttcta caaactcttt ttgtttattt ttctaaatac attcaaatat gtatccgctc   2100
atgagacaat aaccctgata aatgcttcaa taatattgaa aaaggaagag tatgagtatt   2160
caacatttcc gtgtcgccct tattcccttt tttgcggcat tttgccttcc tgtttttgct   2220
cacccagaaa cgctggtgaa agtaaaagat gctgaagatc agttgggtgc acgagtgggt   2280
tacatcgaac tggatctcaa cagcggtaag atccttgaga gttttcgccc cgaagaacgt   2340
tttccaatga tgagcacttt taaagttctg ctatgtggcg cggtattatc ccgtgttgac   2400
gccgggcaag agcaactcgg tcgccgcata cactattctc agaatgactt ggttgagtac   2460
tcaccagtca cagaaaagca tcttacggat ggcatgacag taagagaatt atgcagtgct   2520
gccataacca tgagtgataa cactgcggcc aacttacttc tgacaacgat cggaggaccg   2580
aaggagctaa ccgctttttt gcacaacatg ggggatcatg taactcgcct tgatcgttgg   2640
gaaccggagc tgaatgaagc cataccaaac gacgagcgtg acaccacgat gcctacagca   2700
atggcaacaa cgttgcgcaa actattaact ggcgaactac ttactctagc ttcccggcaa   2760
caattaatag actggatgga ggcggataaa gttgcaggac cacttctgcg ctcggccctt   2820
ccggctggct ggtttattgc tgataaatct ggagccggtg agcgtgggtc tcgcggtatc   2880
attgcagcac tggggccaga tggtaagccc tcccgtatcg tagttatcta cacgacgggg   2940
agtcaggcaa ctatggatga acgaaataga cagatcgctg agataggtgc ctcactgatt   3000
aagcattggt aactgtcaga ccaagtttac tcatatatac tttagattga tttaaaactt   3060
catttttaat ttaaaaggat ctaggtgaag atcctttttg ataatctcat gaccaaaatc   3120
ccttaacgtg agttttcgtt ccactgagcg tcagaccccg tagaaaagat caaaggatct   3180
tcttgagatc cttttttct gcgcgtaatc tgctgcttgc aaacaaaaaa accaccgcta    3240
```

-continued ccagcggtgg tttgtttgcc ggatcaagag ctaccaactc tttttccgaa ggtaactggc 3300
ttcagcagag cgcagatacc aaatactgtc cttctagtgt agccgtagtt aggccaccac 3360
ttcaagaact ctgtagcacc gcctacatac ctcgctctgc taatcctgtt accagtggct 3420
gctgccagtg gcgataagtc gtgtcttacc gggttggact caagacgata gttaccggat 3480
aaggcgcagc ggtcgggctg aacggggggt tcgtgcacac agcccagctt ggagcgaacg 3540
acctacaccg aactgagata cctacagcgt gagctatgag aaagcgccac gcttcccgaa 3600
gggagaaagg cggacaggta tccggtaagc ggcagggtcg gaacaggaga gcgcacgagg 3660
gagcttccag ggggaaacgc ctggtatctt tatagtcctg tcgggtttcg ccacctctga 3720
cttgagcgtc gatttttgtg atgctcgtca ggggggcgga gcctatggaa aaacgccagc 3780
aacgcggcct ttttacggtt cctggccttt tgctggcctt ttgctcacat gttctttcct 3840
gcgttatccc ctgattctgt ggataaccgt attaccgcct ttgagtgagc tgataccgct 3900
cgccgcagcc gaacgaccga gcgcagcgag tcagtgagcg aggaagcgga agagcgcctg 3960
atgcggtatt ttctccttac gcatctgtgc ggtatttcac accgcatatg gtgcactctc 4020
agtacaatct gctctgatgc cgcatagtta agccagtata cactccgcta tcgctacgtg 4080
actgggtcat ggctgcgccc cgacacccgc caacacccgc tgacgcgccc tgacgggctt 4140
gtctgctccc ggcatccgct tacagacaag ctgtgaccgt ctccgggaga gctcgatatc 4200
ccgggcggcc gcttcattta taaatttctt gacattttgg aatagatgtg atataatgtg 4260
tacatatcca tggcggccgc tctagaagaa gcttgggatc cgtcgacctc g 4311

<210> SEQ ID NO 3
<211> LENGTH: 340
<212> TYPE: DNA
<213> ORGANISM: Artificial sequence
<220> FEATURE:
<223> OTHER INFORMATION: Promotor

<400> SEQUENCE: 3
tgtttattta tcactttggc agagtaatta tcctgtgcac tattaatagc aatgtcgcca 60
tgcacattta ccttgcagtt aattgaataa aaatttaact ggcatcagtc ctaaaaaaat 120
tgatttcatc cgcaggctat tgacagaata attcagactg gtctttcagg catccagaca 180
cgctaccgcc cctggctttt tagctaccaa tacactgatt tagtttaatt tttcacaccc 240
tctcagcatg cagtcgttga tgagaaaggg ttattacgga aattaacttc cgaatataag 300
gtgacattat ggtaattgaa tattggcttt ccaataatgc 340

<210> SEQ ID NO 4
<211> LENGTH: 101
<212> TYPE: DNA
<213> ORGANISM: Artificial sequence
<220> FEATURE:
<223> OTHER INFORMATION: Promotor

<400> SEQUENCE: 4
cgaggtcgac ggatcccaag cttcttctag agcggccgcc atggaaattt ccctattata 60
ccatatgccg gccaagatgt caagaaactt atagaatgaa g 101

<210> SEQ ID NO 5
<211> LENGTH: 44
<212> TYPE: DNA
<213> ORGANISM: Artificial sequence
<220> FEATURE:

<223> OTHER INFORMATION: Promotor

<400> SEQUENCE: 5
taagtgtcat tcaatatggt ttttaggagt ttctttaggt tgac 44

<210> SEQ ID NO 6
<211> LENGTH: 485
<212> TYPE: DNA
<213> ORGANISM: Artificial sequence
<220> FEATURE:
<223> OTHER INFORMATION: Promotor

<400> SEQUENCE: 6
tgtttattta tcactttggc agagtaatta tcctgtgcac tattaatagc aatgtcgcca 60
tgcacattta ccttgcagtt aattgaataa aaatttaact ggcatcagtc ctaaaaaaat 120
tgatttcatc cgcaggctat tgacagaata attcagactg gtctttcagg catccagaca 180
cgctaccgcc cctggctttt tagctaccaa tacactgatt tagtttaatt tttcacaccc 240
tctcagcatg cagtcgttga tgagaaaggg ttattacgga aattaacttc cgaatataag 300
gtgacattat ggtaattgaa tattggcttt ccaataatgc cgaggtcgac ggatcccaag 360
cttcttctag agcggccgcc atggaaattt ccctattata ccatatgccg gccaagatgt 420
caagaaactt atagaatgaa gtaagtgtca ttcaatatgg tttttaggag tttctttagg 480
ttgac 485

<210> SEQ ID NO 7
<211> LENGTH: 74
<212> TYPE: DNA
<213> ORGANISM: Artificial sequence
<220> FEATURE:
<223> OTHER INFORMATION: Primer

<400> SEQUENCE: 7
cataatggat ttccttacgc gaaatacggg cagacatggc ctgcccggtt attagtgtag 60
gctggagctg cttc 74

<210> SEQ ID NO 8
<211> LENGTH: 71
<212> TYPE: DNA
<213> ORGANISM: Artificial sequence
<220> FEATURE:
<223> OTHER INFORMATION: Primer

<400> SEQUENCE: 8
gtatgttgtg tggaattgtg agcggataac aatttcacac aggaaacagc tcatatgaat 60
atcctcctta g 71

<210> SEQ ID NO 9
<211> LENGTH: 18
<212> TYPE: DNA
<213> ORGANISM: Artificial sequence
<220> FEATURE:
<223> OTHER INFORMATION: Primer

<400> SEQUENCE: 9
gcggttggaa taatagcg 18

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
caggtttccc gactggaaag 20

<210> SEQ ID NO 11
<211> LENGTH: 75
<212> TYPE: DNA
<213> ORGANISM: Artificial sequence
<220> FEATURE:
<223> OTHER INFORMATION: Primer

<400> SEQUENCE: 11
agaccgccgg ttttaagcag cgggaacatc tctgaacata catgtaaaac ctgcagtgta 60
ggctggagct gcttc 75

<210> SEQ ID NO 12
<211> LENGTH: 82
<212> TYPE: DNA
<213> ORGANISM: Artificial sequence
<220> FEATURE:
<223> OTHER INFORMATION: Primer

<400> SEQUENCE: 12
gtctggcagg gacctgcaca cggattgtgt gtgttccaga gatgataaaa aaggagttag 60
tccatatgaa tatcctcctt ag 82

<210> SEQ ID NO 13
<211> LENGTH: 21
<212> TYPE: DNA
<213> ORGANISM: Artificial sequence
<220> FEATURE:
<223> OTHER INFORMATION: Primer

<400> SEQUENCE: 13
gcgaatatcg ggaaatgcag g 21

<210> SEQ ID NO 14
<211> LENGTH: 22
<212> TYPE: DNA
<213> ORGANISM: Artificial sequence
<220> FEATURE:
<223> OTHER INFORMATION: Primer

<400> SEQUENCE: 14
cagagattgt tttacctgct gg 22

<210> SEQ ID NO 15
<211> LENGTH: 70
<212> TYPE: DNA
<213> ORGANISM: Artificial sequence
<220> FEATURE:
<223> OTHER INFORMATION: Primer

<400> SEQUENCE: 15
catatttctg tcacactctt tagtgattga taacaaaaga ggtgccagga gtgtaggctg 60
gagctgcttc 70

<210> SEQ ID NO 16
<211> LENGTH: 70
<212> TYPE: DNA
<213> ORGANISM: Artificial sequence
<220> FEATURE:

-continued

<223> OTHER INFORMATION: Primer

<400> SEQUENCE: 16
taaaaacgtt taaccagcga ctcccccgct tctcgcgggg gagttttctg catatgaata 60
tcctccttag 70

<210> SEQ ID NO 17
<211> LENGTH: 18
<212> TYPE: DNA
<213> ORGANISM: Artificial sequence
<220> FEATURE:
<223> OTHER INFORMATION: Primer

<400> SEQUENCE: 17
gccacaggtg caattatc 18

<210> SEQ ID NO 18
<211> LENGTH: 23
<212> TYPE: DNA
<213> ORGANISM: Artificial sequence
<220> FEATURE:
<223> OTHER INFORMATION: Primer

<400> SEQUENCE: 18
cattttcgaa gtcgccgggt acg 23

<210> SEQ ID NO 19
<211> LENGTH: 70
<212> TYPE: DNA
<213> ORGANISM: Artificial sequence
<220> FEATURE:
<223> OTHER INFORMATION: Primer

<400> SEQUENCE: 19
ggcgctacaa tcttccaaag tcacaattct caaaatcaga agagtattgc gtgtaggctg 60
gagctgcttc 70

<210> SEQ ID NO 20
<211> LENGTH: 70
<212> TYPE: DNA
<213> ORGANISM: Artificial sequence
<220> FEATURE:
<223> OTHER INFORMATION: Primer

<400> SEQUENCE: 20
ggttgccgga tgcggcgtga acgccttatc cggcctacat atcgacgatg catatgaata 60
tcctccttag 70

<210> SEQ ID NO 21
<211> LENGTH: 20
<212> TYPE: DNA
<213> ORGANISM: Artificial sequence
<220> FEATURE:
<223> OTHER INFORMATION: Primer

<400> SEQUENCE: 21
ggctcctcca acaccgttac 20

<210> SEQ ID NO 22
<211> LENGTH: 20
<212> TYPE: DNA
<213> ORGANISM: Artificial sequence
<220> FEATURE:
<223> OTHER INFORMATION: Primer -continued

<400> SEQUENCE: 22
tacatatcgg catcgacctg 20

<210> SEQ ID NO 23
<211> LENGTH: 19
<212> TYPE: DNA
<213> ORGANISM: Artificial sequence
<220> FEATURE:
<223> OTHER INFORMATION: Primer

<400> SEQUENCE: 23
taccgccatt tggcctgac 19

<210> SEQ ID NO 24
<211> LENGTH: 20
<212> TYPE: DNA
<213> ORGANISM: Artificial sequence
<220> FEATURE:
<223> OTHER INFORMATION: Primer

<400> SEQUENCE: 24
aaagtgcgct ttgtccatgc 20

<210> SEQ ID NO 25
<211> LENGTH: 69
<212> TYPE: DNA
<213> ORGANISM: Artificial sequence
<220> FEATURE:
<223> OTHER INFORMATION: Primer

<400> SEQUENCE: 25
gacttccggc aacagatttc attttgcatt ccaaagttca gaggtagtcg tgtaggctgg 60
agctgcttc 69

<210> SEQ ID NO 26
<211> LENGTH: 69
<212> TYPE: DNA
<213> ORGANISM: Artificial sequence
<220> FEATURE:
<223> OTHER INFORMATION: Primer

<400> SEQUENCE: 26
gcttctgtca tcggtttcag ggtaaaggaa tctgcctttt tccgaaatcc atatgaatat 60
cctccttag 69

<210> SEQ ID NO 27
<211> LENGTH: 21
<212> TYPE: DNA
<213> ORGANISM: Artificial sequence
<220> FEATURE:
<223> OTHER INFORMATION: Primer

<400> SEQUENCE: 27
tagcgtccct ggaaaggtaa c 21

<210> SEQ ID NO 28
<211> LENGTH: 20
<212> TYPE: DNA
<213> ORGANISM: Artificial sequence
<220> FEATURE:
<223> OTHER INFORMATION: Primer

<400> SEQUENCE: 28
tccctcatca tccgtcatag 20

<210> SEQ ID NO 29
<211> LENGTH: 71
<212> TYPE: DNA
<213> ORGANISM: Artificial sequence
<220> FEATURE:
<223> OTHER INFORMATION: Primer

<400> SEQUENCE: 29
cactttccgc tgattcggtg ccagactgaa atcagcctat aggaggaaat ggtgtaggct 60
ggagctgctt c 71

<210> SEQ ID NO 30
<211> LENGTH: 70
<212> TYPE: DNA
<213> ORGANISM: Artificial sequence
<220> FEATURE:
<223> OTHER INFORMATION: Primer

<400> SEQUENCE: 30
gttgccgaca ggttggtgat gattccccca atgctggggg aatgtttttg catatgaata 60
tcctccttag 70

<210> SEQ ID NO 31
<211> LENGTH: 79
<212> TYPE: DNA
<213> ORGANISM: Artificial sequence
<220> FEATURE:
<223> OTHER INFORMATION: Primer

<400> SEQUENCE: 31
ggttgaaaaa taaaaacggc gctaaaaagc gccgtttttt ttgacggtgg taaagccgag 60
tgtaggctgg agctgcttc 79

<210> SEQ ID NO 32
<211> LENGTH: 76
<212> TYPE: DNA
<213> ORGANISM: Artificial sequence
<220> FEATURE:
<223> OTHER INFORMATION: Primer

<400> SEQUENCE: 32
ggtcagggac ttttgtactt cctgtttcga tttagttggc aatttaggta gcaaaccata 60
tgaatatcct ccttag 76

<210> SEQ ID NO 33
<211> LENGTH: 22
<212> TYPE: DNA
<213> ORGANISM: Artificial sequence
<220> FEATURE:
<223> OTHER INFORMATION: Primer

<400> SEQUENCE: 33
ctgccgaaaa tgaaagccag ta 22

<210> SEQ ID NO 34
<211> LENGTH: 22
<212> TYPE: DNA
<213> ORGANISM: Artificial sequence
<220> FEATURE:
<223> OTHER INFORMATION: Primer

<400> SEQUENCE: 34
ggaaagtgca tcaagaacgc aa 22

<210> SEQ ID NO 35
<211> LENGTH: 71
<212> TYPE: DNA
<213> ORGANISM: Artificial sequence
<220> FEATURE:
<223> OTHER INFORMATION: Primer

<400> SEQUENCE: 35
ttgccactca ggtatgatgg gcagaatatt gcctctgccc gccagaaaaa ggtgtaggct 60
ggagctgctt c 71

<210> SEQ ID NO 36
<211> LENGTH: 77
<212> TYPE: DNA
<213> ORGANISM: Artificial sequence
<220> FEATURE:
<223> OTHER INFORMATION: Primer

<400> SEQUENCE: 36
gttcaacatt aactcatcgg atcagttcag taactattgc attagctaac aataaaacat 60
atgaatatcc tccttag 77

<210> SEQ ID NO 37
<211> LENGTH: 21
<212> TYPE: DNA
<213> ORGANISM: Artificial sequence
<220> FEATURE:
<223> OTHER INFORMATION: Primer

<400> SEQUENCE: 37
cggtggaatg agatcttgcg a 21

<210> SEQ ID NO 38
<211> LENGTH: 20
<212> TYPE: DNA
<213> ORGANISM: Artificial sequence
<220> FEATURE:
<223> OTHER INFORMATION: Primer

<400> SEQUENCE: 38
acttgctccc gacacgctca 20

<210> SEQ ID NO 39
<211> LENGTH: 71
<212> TYPE: DNA
<213> ORGANISM: Artificial sequence
<220> FEATURE:
<223> OTHER INFORMATION: Primer

<400> SEQUENCE: 39
ttgccactca ggtatgatgg gcagaatatt gcctctgccc gccagaaaaa gccgcttaca 60
gacaagctgt g 71

<210> SEQ ID NO 40
<211> LENGTH: 77
<212> TYPE: DNA
<213> ORGANISM: Artificial sequence
<220> FEATURE:
<223> OTHER INFORMATION: Primer

<400> SEQUENCE: 40
gttcaacatt aactcatcgg atcagttcag taactattgc attagctaac aataaaaagc 60
catgacccgg gaattac 77

<210> SEQ ID NO 41
<211> LENGTH: 44
<212> TYPE: DNA
<213> ORGANISM: Artificial sequence
<220> FEATURE:
<223> OTHER INFORMATION: Primer

<400> SEQUENCE: 41
ctattgcatt agctaacaat aaaacttttt ctggcgggca gagg 44

<210> SEQ ID NO 42
<211> LENGTH: 48
<212> TYPE: DNA
<213> ORGANISM: Artificial sequence
<220> FEATURE:
<223> OTHER INFORMATION: Primer

<400> SEQUENCE: 42
cctctgcccg ccagaaaaag ttttattgtt agctaatgca atagttac 48

<210> SEQ ID NO 43
<211> LENGTH: 20
<212> TYPE: DNA
<213> ORGANISM: Artificial sequence
<220> FEATURE:
<223> OTHER INFORMATION: Primer

<400> SEQUENCE: 43
gccagcgcga taatcaccag 20

<210> SEQ ID NO 44
<211> LENGTH: 19
<212> TYPE: DNA
<213> ORGANISM: Artificial sequence
<220> FEATURE:
<223> OTHER INFORMATION: Primer

<400> SEQUENCE: 44
tgcgcctgaa tgtggaatc 19

<210> SEQ ID NO 45
<211> LENGTH: 70
<212> TYPE: DNA
<213> ORGANISM: Artificial sequence
<220> FEATURE:
<223> OTHER INFORMATION: Primer

<400> SEQUENCE: 45
ttttgatatc gaaccagacg ctccattcgc ggatgtactc aaggtcgaac gtgtaggctg 60
gagctgcttc 70

<210> SEQ ID NO 46
<211> LENGTH: 70
<212> TYPE: DNA
<213> ORGANISM: Artificial sequence
<220> FEATURE:
<223> OTHER INFORMATION: Primer

<400> SEQUENCE: 46
tctatggtgc aacgcttttc agatatcacc atcatgtttg ccggactatg catatgaata 60
tcctccttag 70

<210> SEQ ID NO 47
<211> LENGTH: 70
<212> TYPE: DNA
<213> ORGANISM: Artificial sequence
<220> FEATURE:
<223> OTHER INFORMATION: Primer

<400> SEQUENCE: 47
tcaatatgcc gctttgttaa cgaaaccttt gaacaccgtc aggaaaacga ttttgatatc 60
gaaccagacg 70

<210> SEQ ID NO 48
<211> LENGTH: 70
<212> TYPE: DNA
<213> ORGANISM: Artificial sequence
<220> FEATURE:
<223> OTHER INFORMATION: Primer

<400> SEQUENCE: 48
tgacaaatct aaaaaagcgc gagcgagcga aaaccaatgc atcgttaatc tctatggtgc 60
aacgcttttc 70

<210> SEQ ID NO 49
<211> LENGTH: 70
<212> TYPE: DNA
<213> ORGANISM: Artificial sequence
<220> FEATURE:
<223> OTHER INFORMATION: Primer

<400> SEQUENCE: 49
cgctttgtta acgaaacctt tgaacaccgt caggaaaacg attttgatat cgaaccagac 60
gctccattcg 70

<210> SEQ ID NO 50
<211> LENGTH: 70
<212> TYPE: DNA
<213> ORGANISM: Artificial sequence
<220> FEATURE:
<223> OTHER INFORMATION: Primer

<400> SEQUENCE: 50
cagtcgtgtc atctgattac ctggcggaaa ttaaactaag agagagctct gtgtaggctg 60
gagctgcttc 70

<210> SEQ ID NO 51
<211> LENGTH: 70
<212> TYPE: DNA
<213> ORGANISM: Artificial sequence
<220> FEATURE:
<223> OTHER INFORMATION: Primer

<400> SEQUENCE: 51
cgaattagcc tgccagccct gtttttatta gtgcattttg cgcgaggtca catatgaata 60
tcctccttag 70

<210> SEQ ID NO 52
<211> LENGTH: 20
<212> TYPE: DNA
<213> ORGANISM: Artificial sequence
<220> FEATURE:
<223> OTHER INFORMATION: Primer

<400> SEQUENCE: 52
agcgcaacag gcatctggtg 20

<210> SEQ ID NO 53
<211> LENGTH: 20
<212> TYPE: DNA
<213> ORGANISM: Artificial sequence
<220> FEATURE:
<223> OTHER INFORMATION: Primer

<400> SEQUENCE: 53
tatatcaggc cagccatccc 20

<210> SEQ ID NO 54
<211> LENGTH: 69
<212> TYPE: DNA
<213> ORGANISM: Artificial sequence
<220> FEATURE:
<223> OTHER INFORMATION: Primer

<400> SEQUENCE: 54
gctgaacttg taggcctgat aagcgcagcg tatcaggcaa tttttataat cttcatttaa 60
atggcgcgc 69

<210> SEQ ID NO 55
<211> LENGTH: 69
<212> TYPE: DNA
<213> ORGANISM: Artificial sequence
<220> FEATURE:
<223> OTHER INFORMATION: Primer

<400> SEQUENCE: 55
gcgcaacgca attaatgtga gttagctcac tcattaggca ccccaggctt cgcctacctg 60
tgacggaag 69

<210> SEQ ID NO 56
<211> LENGTH: 70
<212> TYPE: DNA
<213> ORGANISM: Artificial sequence
<220> FEATURE:
<223> OTHER INFORMATION: Primer

<400> SEQUENCE: 56
gcgcaacgca attaatgtga gttagctcac tcattaggca ccccaggctt gtgtaggctg 60
gagctgcttc 70

<210> SEQ ID NO 57
<211> LENGTH: 70
<212> TYPE: DNA
<213> ORGANISM: Artificial sequence
<220> FEATURE:
<223> OTHER INFORMATION: Primer

<400> SEQUENCE: 57
gctgaacttg taggcctgat aagcgcagcg tatcaggcaa tttttataat cttaagcgac 60
ttcattcacc 70

<210> SEQ ID NO 58
<211> LENGTH: 68
<212> TYPE: DNA
<213> ORGANISM: Artificial sequence
<220> FEATURE:
<223> OTHER INFORMATION: Primer

<400> SEQUENCE: 58
cgacgcttgt tcctgcgctt tgttcatgcc ggatgcggct aatgtagatc gctgaacttg 60
taggcctg 68

<210> SEQ ID NO 59
<211> LENGTH: 69
<212> TYPE: DNA
<213> ORGANISM: Artificial sequence
<220> FEATURE:
<223> OTHER INFORMATION: Primer

<400> SEQUENCE: 59
cattaatgca gctggcacga caggtttccc gactggaaag cgggcagtga gcgcaacgca 60
attaatgtg 69

<210> SEQ ID NO 60
<211> LENGTH: 69
<212> TYPE: DNA
<213> ORGANISM: Artificial sequence
<220> FEATURE:
<223> OTHER INFORMATION: Primer

<400> SEQUENCE: 60
gacttccggc aacagatttc attttgcatt ccaaagttca gaggtagtcg tgtaggctgg 60
agctgcttc 69

<210> SEQ ID NO 61
<211> LENGTH: 69
<212> TYPE: DNA
<213> ORGANISM: Artificial sequence
<220> FEATURE:
<223> OTHER INFORMATION: Primer

<400> SEQUENCE: 61
gcttctgtca tcggtttcag ggtaaaggaa tctgcctttt tccgaaatca agcttgcatg 60
cctgcatcc 69

<210> SEQ ID NO 62
<211> LENGTH: 20
<212> TYPE: DNA
<213> ORGANISM: Artificial sequence
<220> FEATURE:
<223> OTHER INFORMATION: Primer

<400> SEQUENCE: 62
agaggctatt cggctatgac 20

<210> SEQ ID NO 63
<211> LENGTH: 20
<212> TYPE: DNA
<213> ORGANISM: Artificial sequence
<220> FEATURE:
<223> OTHER INFORMATION: Primer

<400> SEQUENCE: 63
cgccatgttg gaatgggagg 20

<210> SEQ ID NO 64
<211> LENGTH: 70
<212> TYPE: DNA
<213> ORGANISM: Artificial sequence
<220> FEATURE:

<223> OTHER INFORMATION: Primer

<400> SEQUENCE: 64
tgattgttat actatttgca cattcgttgg atcacttcga tgtgcaagaa gacttccggc 60
aacagatttc 70

<210> SEQ ID NO 65
<211> LENGTH: 70
<212> TYPE: DNA
<213> ORGANISM: Artificial sequence
<220> FEATURE:
<223> OTHER INFORMATION: Primer

<400> SEQUENCE: 65
aattgcagaa ttcatgtagg cctgataagc gaagcgcatc aggcattttt gcttctgtca 60
tcggtttcag 70

<210> SEQ ID NO 66
<211> LENGTH: 19
<212> TYPE: DNA
<213> ORGANISM: Artificial sequence
<220> FEATURE:
<223> OTHER INFORMATION: Primer

<400> SEQUENCE: 66
taccgccatt tggcctgac 19

<210> SEQ ID NO 67
<211> LENGTH: 20
<212> TYPE: DNA
<213> ORGANISM: Artificial sequence
<220> FEATURE:
<223> OTHER INFORMATION: Primer

<400> SEQUENCE: 67
aaagtgcgct ttgtccatgc 20

<210> SEQ ID NO 68
<211> LENGTH: 70
<212> TYPE: DNA
<213> ORGANISM: Artificial sequence
<220> FEATURE:
<223> OTHER INFORMATION: Primer

<400> SEQUENCE: 68
atcggcattg cccagaaggg gccgtttatg ttgccagaca gcgctactga gtgtaggctg 60
gagctgcttc 70

<210> SEQ ID NO 69
<211> LENGTH: 70
<212> TYPE: DNA
<213> ORGANISM: Artificial sequence
<220> FEATURE:
<223> OTHER INFORMATION: Primer

<400> SEQUENCE: 69
attcgagcag atgatttact aaaaaagttt aacattatca ggagagcatt aagcttgcat 60
gcctgcatcc 70

<210> SEQ ID NO 70
<211> LENGTH: 68
<212> TYPE: DNA
<213> ORGANISM: Artificial sequence
<220> FEATURE:
<223> OTHER INFORMATION: Primer

<400> SEQUENCE: 70
aagccgttat agtgcctcag tttaaggatc ggtcaactaa tccttaactg atcggcattg 60
cccagaag 68

<210> SEQ ID NO 71
<211> LENGTH: 77
<212> TYPE: DNA
<213> ORGANISM: Artificial sequence
<220> FEATURE:
<223> OTHER INFORMATION: Primer

<400> SEQUENCE: 71
ttgattttca taggttaagc aaatcatcac cgcactgact atactctcgt attcgagcag 60
atgatttact aaaaaag 77

<210> SEQ ID NO 72
<211> LENGTH: 20
<212> TYPE: DNA
<213> ORGANISM: Artificial sequence
<220> FEATURE:
<223> OTHER INFORMATION: Primer

<400> SEQUENCE: 72
gcgtcaggca gtgttgtatc 20

<210> SEQ ID NO 73
<211> LENGTH: 20
<212> TYPE: DNA
<213> ORGANISM: Artificial sequence
<220> FEATURE:
<223> OTHER INFORMATION: Primer

<400> SEQUENCE: 73
ctggaagtga cgcattagag 20

<210> SEQ ID NO 74
<211> LENGTH: 22
<212> TYPE: DNA
<213> ORGANISM: Artificial sequence
<220> FEATURE:
<223> OTHER INFORMATION: Primer

<400> SEQUENCE: 74
tgtcattact tacacatccc gc 22

<210> SEQ ID NO 75
<211> LENGTH: 22
<212> TYPE: DNA
<213> ORGANISM: Artificial sequence
<220> FEATURE:
<223> OTHER INFORMATION: Primer

<400> SEQUENCE: 75
gcattcaata cgggtattgt gg 22

<210> SEQ ID NO 76
<211> LENGTH: 70
<212> TYPE: DNA
<213> ORGANISM: Artificial sequence
<220> FEATURE:
<223> OTHER INFORMATION: Primer

<400> SEQUENCE: 76
cattggggat tatctgaatc agctcccctg gaatgcaggg gagcggcaag gtgtaggctg 60
gagctgcttc 70

<210> SEQ ID NO 77
<211> LENGTH: 70
<212> TYPE: DNA
<213> ORGANISM: Artificial sequence
<220> FEATURE:
<223> OTHER INFORMATION: Primer

<400> SEQUENCE: 77
tatttttagt agcttaaatg tgattcaaca tcactggaga aagtcttatg aagcttgcat 60
gcctgcatcc 70

<210> SEQ ID NO 78
<211> LENGTH: 72
<212> TYPE: DNA
<213> ORGANISM: Artificial sequence
<220> FEATURE:
<223> OTHER INFORMATION: Primer

<400> SEQUENCE: 78
caattacagt ttctgactca ggactatttt aagaatagag gatgaaaggt cattggggat 60
tatctgaatc ag 72

<210> SEQ ID NO 79
<211> LENGTH: 80
<212> TYPE: DNA
<213> ORGANISM: Artificial sequence
<220> FEATURE:
<223> OTHER INFORMATION: Primer

<400> SEQUENCE: 79
gaatttttca atatcgccat agctttcaat taaatttgaa attttgtaaa atatttttag 60
tagcttaaat gtgattcaac 80

<210> SEQ ID NO 80
<211> LENGTH: 20
<212> TYPE: DNA
<213> ORGANISM: Artificial sequence
<220> FEATURE:
<223> OTHER INFORMATION: Primer

<400> SEQUENCE: 80
ttcaccgcta aagcggttac 20

<210> SEQ ID NO 81
<211> LENGTH: 20
<212> TYPE: DNA
<213> ORGANISM: Artificial sequence
<220> FEATURE:
<223> OTHER INFORMATION: Primer

<400> SEQUENCE: 81
cgcgtaatgc gtgggctttc 20

<210> SEQ ID NO 82
<211> LENGTH: 21
<212> TYPE: DNA
<213> ORGANISM: Artificial sequence
<220> FEATURE:
<223> OTHER INFORMATION: Primer

<400> SEQUENCE: 82
ccggcatatg gtataatagg g 21

<210> SEQ ID NO 83
<211> LENGTH: 18
<212> TYPE: DNA
<213> ORGANISM: Artificial sequence
<220> FEATURE:
<223> OTHER INFORMATION: Primer

<400> SEQUENCE: 83
acggcttgct ggccatca 18

<210> SEQ ID NO 84
<211> LENGTH: 68
<212> TYPE: DNA
<213> ORGANISM: Artificial sequence
<220> FEATURE:
<223> OTHER INFORMATION: Primer

<400> SEQUENCE: 84
cgaatataag gtgacattat ggtaattgaa tattggcttt ccaataatgc tacggcccca 60
aggtccaa 68

<210> SEQ ID NO 85
<211> LENGTH: 70
<212> TYPE: DNA
<213> ORGANISM: Artificial sequence
<220> FEATURE:
<223> OTHER INFORMATION: Primer

<400> SEQUENCE: 85
aatattgtca acctaaagaa actcctaaaa accatattga atgacactta ttggcttcag 60
ggatgaggcg 70

<210> SEQ ID NO 86
<211> LENGTH: 20
<212> TYPE: DNA
<213> ORGANISM: Artificial sequence
<220> FEATURE:
<223> OTHER INFORMATION: Primer

<400> SEQUENCE: 86
tcccgactac gtggaccttg 20

<210> SEQ ID NO 87
<211> LENGTH: 90
<212> TYPE: DNA
<213> ORGANISM: Artificial sequence
<220> FEATURE:
<223> OTHER INFORMATION: Primer

<400> SEQUENCE: 87
catatggtat aatagggaaa tttccatggc ggccgctcta gaagaagctt gggatccgtc 60
gacctcggca ttattggaaa gccaatattc 90

<210> SEQ ID NO 88
<211> LENGTH: 86
<212> TYPE: DNA
<213> ORGANISM: Artificial sequence
<220> FEATURE:
<223> OTHER INFORMATION: Primer -continued

```
<400> SEQUENCE: 88

gccgccatgg aaatttccct attataccat atgccggcca agatgtcaag aaacttatag     60

aatgaagtaa gtgtcattca atatgg                                          86


<210> SEQ ID NO 89
<211> LENGTH: 73
<212> TYPE: DNA
<213> ORGANISM: Artificial sequence
<220> FEATURE:
<223> OTHER INFORMATION: Primer

<400> SEQUENCE: 89

aatattgtca acctaaagaa actcctaaaa accatattga atgacactta cttcattcta     60

taagtttctt gac                                                        73


<210> SEQ ID NO 90
<211> LENGTH: 74
<212> TYPE: DNA
<213> ORGANISM: Artificial sequence
<220> FEATURE:
<223> OTHER INFORMATION: Primer

<400> SEQUENCE: 90

cgaatataag gtgacattat ggtaattgaa tattggcttt ccaataatgc cgaggtcgac     60

ggatcccaag cttc                                                       74
```